US009493549B2

(12) United States Patent
Diskin et al.

(10) Patent No.: US 9,493,549 B2
(45) Date of Patent: Nov. 15, 2016

(54) ANTIBODIES DIRECTED TOWARD THE HIV-1 GP120 CD4 BINDING SITE WITH INCREASED POTENCY AND BREADTH

(71) Applicants: CALIFORNIA INSTITUTE OF TECHNOLOGY, Pasadena, CA (US); THE ROCKEFELLER UNIVERSITY, New York, NY (US)

(72) Inventors: Ron Diskin, Pasadena, CA (US); Pamela J. Bjorkman, La Canada, CA (US); Michel Nussenzweig, New York, NY (US); Johannes Scheid, New York, NY (US)

(73) Assignees: THE ROCKEFELLER UNIVERSITY, New York, NY (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 13/714,398

(22) Filed: Dec. 13, 2012

(65) Prior Publication Data
US 2013/0209454 A1 Aug. 15, 2013

Related U.S. Application Data

(63) Continuation-in-part of application No. 13/558,312, filed on Jul. 25, 2012.

(60) Provisional application No. 61/511,425, filed on Jul. 25, 2011, provisional application No. 61/523,244, filed on Aug. 12, 2011, provisional application No. 61/570,173, filed on Dec. 13, 2011.

(51) Int. Cl.
*C07K 16/10* (2006.01)
(52) U.S. Cl.
CPC ........... *C07K 16/10* (2013.01); *C07K 16/1063* (2013.01); *C07K 2317/21* (2013.01); *C07K 2317/34* (2013.01); *C07K 2317/565* (2013.01); *C07K 2317/76* (2013.01); *C07K 2317/92* (2013.01)

(58) Field of Classification Search
CPC .................. C07K 16/1063; C07K 2317/21
See application file for complete search history.

(56) References Cited

U.S. PATENT DOCUMENTS

| 5,229,275 | A | 7/1993 | Goroff |
| 5,545,806 | A | 8/1996 | Lonberg et al. |
| 5,545,807 | A | 8/1996 | Surani et al. |
| 5,567,610 | A | 10/1996 | Borrebaeck et al. |
| 5,569,825 | A | 10/1996 | Lonberg et al. |
| 5,591,669 | A | 1/1997 | Krimpenfort et al. |
| 5,641,870 | A | 6/1997 | Rinderknecht et al. |
| 2009/0053220 | A1 | 2/2009 | Duensing et al. |

FOREIGN PATENT DOCUMENTS

| WO | WO 93/19786 | 10/1993 |
| WO | WO 97/17852 | 5/1997 |
| WO | WO 2011/038290 A2 | 3/2011 |
| WO | WO 2012/158948 A1 | 11/2012 |

OTHER PUBLICATIONS

Xiang, J., et al., 1991, Modification in framework region I results in a decreased affinity of chimeric anti-TAG72 antibody, Mol. Immunol. 28(1/2):141-148.*
Chen, C., et al., 1992, Generation and analysis of random point mutations in an antibody CDR2 sequence: many mutated antibodies lose their ability to bind antigen, J. Exp. Med. 176:855-866.*
Scharf, L., et al., Apr. 2013, Structural basis for HIV-1 gp120 recognition by a germ-line version of a broadly neutralizing antibody, Proc. Natl. Acad. Sci. 110(15):6049-6054.*
International Search Report and Written Opinion for corresponding PCT application No. PCT/US2012/069600, mailed Jun. 21, 2013, 17pp.
Wu, Xueling et al.; " Rational Design of Envelope Identifies Broadly Neutralizing Human Monoclonal Antibodies to HIV-1"; Science; Aug. 13, 2010; vol. 329; No. 5993; pp. 856-861.
Abhinandan, K.R. and Martin, A.C.R. (2008), "Analysis and improvements to Kabat and structurally correct numbering of antibody variable domains," Molecular Immunology, 45: 3832-3839.
Adams Paul D. et al.; "PHENIX; a comprehensive Python-based system for macromolecular structure solution"; Acta Crystallographica Section D; Biological Crystallography, D66; 2010; pp. 213-221.
Akers and Defilippis, 2000, Peptides and Proteins as Parenteral Solutions. In: Pharmaceutical Formulation Development of Peptides and Proteins. Philadelphia, PA: Taylor and Francis; pp. 143-177 (on Order).
Akers, Michael J. et al.; "Formulation Development of Protein Dosage Forms"; Development and Manufacture of Protein Pharmaceuticals; 2002; Pharm. Biotechnol. 14; pp. 47-127.
Brüggemann, Marianne et al.; "Designer Mice: The Production of Human Antibody Repertoires in Transgenic Animals"; Generation of Antibodies by Cell and Gene Immortalization; Year in Immuno.; 1993; vol. 7; pp. 33-40.
Casadevall, Arturo; "Antibodies for defense against biological attack"; Nature Biotechnology; vol. 20; Feb. 2002; p. 114.
Diskin, Ron et al.; "Structure of a clade C HIV-1 gp120 bound to CD4 and CD4-induced antibody reveals anti-CD4 polyreactivity"; Nature Structural & Molecular Biology; vol. 17; No. 5; May 2010; pp. 608-613.
Diskin, Ron et al.; "Increasing the Potency and Breadth of an HIV Antibody by Using Structure-Based Rational Design"; Science; vol. 334; Dec. 2, 2011; pp. 1289-1293.

(Continued)

*Primary Examiner* — Jeffrey Parkin
(74) *Attorney, Agent, or Firm* — Lewis Roca Rothgerber Christie LLP

(57) ABSTRACT

Embodiments of the present invention are directed to compositions and methods for anti-HIV (anti-CD4 binding site) potent VRC01-like (PVL) antibodies targeted to gp120 having an amino acid substitution in the heavy chain at a residue in the anti-CD4 binding site PVL antibody that is equivalent to Phe43 in CD4 and an amino acid substitution in the light chain, these antibodies having improved potency and breadth.

8 Claims, 42 Drawing Sheets
(41 of 42 Drawing Sheet(s) Filed in Color)

(56) References Cited

OTHER PUBLICATIONS

Emsley, Paul et al.; "Coot: model-building tools for molecular graphics"; Research papers; Acta Crystallographica Section D; Biological Crystallography; D60; 2004; pp. 2126-2132.
Igarashi, Tatsuhiko et al.; "Human immunodeficiency virus type 1 neutralizing antibodies accelerate clearance of cell-free virions from blood plasma"; Nature Medicine; vol. 5, No. 2; Feb. 1999; pp, 211-216.
Jakabovits, Aya et al.; "Germ-line transmission and expression of a human-derived yeast artificial chromosome"; Letters to Nature; vol. 362; Mar. 18, 1993; pp. 255-258.
Jakobovits, Aya et al.; "Analysis of homozygous mutant chimeric mice: Deletion of the immunoglobulin heavy-chain joining region blocks B-cell development and antibody production"; Proc. Nati, Acad, Sci, USA; Genetics; vol. 90; Mar. 1993; pp. 2551-2555.
Jones, Peter T. et al.; "Replacing the complementarity-determining regions in a human antibody with those from a mouse"; Nature; vol, 321; May 29, 1986; pp, 522-525.
Kabsch, Wolfgang; "XDS"; Acta Crystallographica Section D; Biological Crystallography; D66; 2010; pp. 125-132.
Keller, Margaret A. et al.; "Passive Immunity in Prevention and Treatment of Infectious Diseases"; Clinical Microbiology Reviews; 2000; vol. 13; No. 4; pp. 602-614.
Klein, Joshua S. et al.; "Examination of the contributions of size and avidity to the neutralization mechanisms of the anti-HIV antibodies b12 and 4E10"; PNAS; vol. 106; No. 18; May 5, 2009; pp. 7385-7390.
Kwong, Peter D. et al.; "Structure of an HIV gp120 envelope glycoprotein in complex with the CD4 receptor and a neutralizing human antibody"; Nature, vol. 393; Jun. 18, 1998; pp. 648-659.
Li Yuxing et al.; "Mechanism Neutralization by the Broadly Neutralizing HIV-1 Monoclonal Antibody VRC0"; Journal of Virology; vol. 85; No, 17; Sep. 2011; pp. 8954-8967.
Madani, Navid et al.; "Small-Molecule CD4 Mimics Interact with a Highly Conserved Pocket on HIV-1 gp120"; Structure; 16(11); Nov. 12, 2008; pp. 1689-1701.
McCoy, Airlie J. et al.; "Phaser crystallographic software"; Journal of Applied Crystallography; vol. 40; pp. 658-674.
McGoff and Scher, 2000, Solution Formulation of Proteins/Peptides: In McNally, E.J., ed. Protein Formulation and Delivery. New York, NY: Marcel Dekker; pp. 139-158 (on Order).
Montefiori, David C.; "Evaluating Neutralizing Antibodies Against HIV, SIV, and SHIV in Luciferase Reporter Gene Assays"; Basic Protocol 1; Detection and Analysis of HIV; Current Protocols in Immunology; Chapter 12; Unit 12.11; 2004; 17pp.
Reichmann, Lutz et al.; "Reshaping human antibodies for therapy"; Nature; vol. 332; Mar. 24, 1988; pp. 323-327.
Sather, D. Noah, et al.; "Broadly Neutralizing Antibodies Developed by an HIV-Positive Elite Neutralizer Exact a Replication Fitness Cost on the Contemporaneous Virus"; Journal of Virology; vol, 86; No. 23; Dec. 2012; pp. 12676-12685.
Scheid, Johannes F. et al.; "Sequence and Structural Convergence of Broad and Potent HIV Antibodies That Mimic CD4 Binding"; Science; vol. 333; Sep. 16, 2011; pp. 1633-1637.
Shibata, Riri et al.; "Neutralizing antibody directed against the HIV-1 envelope glycoprotein can completely block HIV-1/SIV chimeric virus infections of macaque monkeys"; Nature Medicine; vol. 5; No, 2; Feb. 1999; pp. 204-210.
Verhoeyen, Martine et al.; "Reshaping Human Antibodies: Grafting an Antilysozyme Activity"; Science; vol. 239; 1988; pp. 1534-1536.
Walker, Laura M. et al.; "Broad neutralization coverage of HIV by Multiple highly potent antibodies"; Nature; 2011; 6pp.
West, Jr., Anthony P. et al.; "Structural basis for germ-line gene usage of a potent class of antibodies targeting the CD4-binding site of HIV-1 gp120"; PNAS; Jun. 27, 2012; pp. E2083-E2090.
Wu, Xueling et al; "Focused Evolution of HIV-1 Neutralizing Antibodies Revealed by Structures and Deep Sequencing"; Science; vol. 333; Sep. 16, 2011; pp. 1593-1602.
Zhou, Tongqin et al.; "Structural Basis for Broad and Potent Neutralization of HIV-1 by Antibody VRC01"; Science; vol. 329; Aug. 13, 2010; pp. 811-817.
International Search Report and Written Opinion for corresponding PCT Application Nib. PCT/US2012/048209; mailed Feb. 28, 2013; 8pp.

* cited by examiner

FIGURE 2

Data collection and refinement statistics

| | NIH45-46-93TH057 | Fab NIH45-46 |
|---|---|---|
| Data collection | | |
| Wavelength (Å) | 0.953 | 0.953 |
| Space group | P2₁2₁2₁ | P2₁2₁2₁ |
| Cell dimensions | | |
| a, b, c (Å) | 68.1, 70.5, 217.7 | 49.4, 87.4, 186.4 |
| α, β, γ (°) | 90.0, 90.0, 90.0 | 90.0, 90.0, 90.0 |
| Resolution (Å) | 37.05-2.45 (2.51-2.45) | 38.68-2.60 (2.67-2.60) |
| $R_{sym}$ (%) | 7.5 (66.9) | 12.2 (105.6) |
| $R_{mrgd-F}$ (%) | 11.6 (108.1) | 13.1 (78.0) |
| I / σI | 10.8 (1.8) | 12.83 (2.0) |
| Completeness (%) | 98.6 (98.7) | 99.5 (99.9) |
| Multiplicity | 3.7 | 6.6 |
| Reflections | 145342 | 150105 |
| Unique reflections | 39082 | 22795 |
| Refinement | | |
| Resolution (Å) | 37.05-2.45 | 38.68-2.6 |
| No. reflections | 38987 | 22692 |
| $R_{work}$ / $R_{free}$ | 20.7 / 25.6 | 18.4 / 23.8 |
| No. atoms | | |
| Protein | 5989 | 3380 |
| Ligand/ion | 148 | 37 |
| Water | 87 | 125 |
| B-factors | | |
| Protein | 79.9 | 46.0 |
| Ligand/ion | 100.4 | 80.9 |
| Water | 62 | 42.0 |
| Ramachandran | | |
| Favored (%) | 96.12 | 96.49 |
| Allowed (%) | 3.48 | 3.28 |
| Outlier (%) | 0.40 | 0.23 |
| R.m.s. deviations | | |
| Bond lengths (Å) | 0.004 | 0.004 |
| Bond angles (°) | 0.754 | 0.838 |

5% of unique reflections were removed as a test set for the $R_{free}$ calculation.
Values in parentheses are for the highest resolution shell.

CD4-ZM135M.PL10a

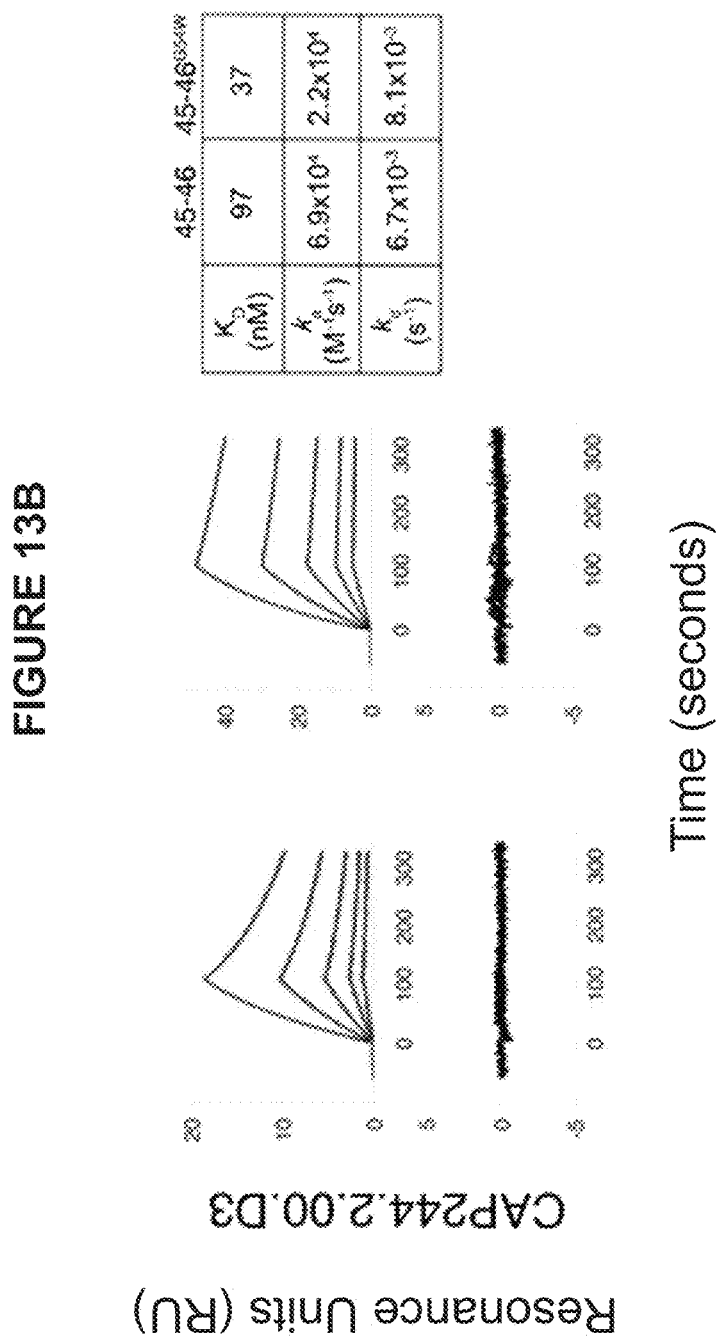

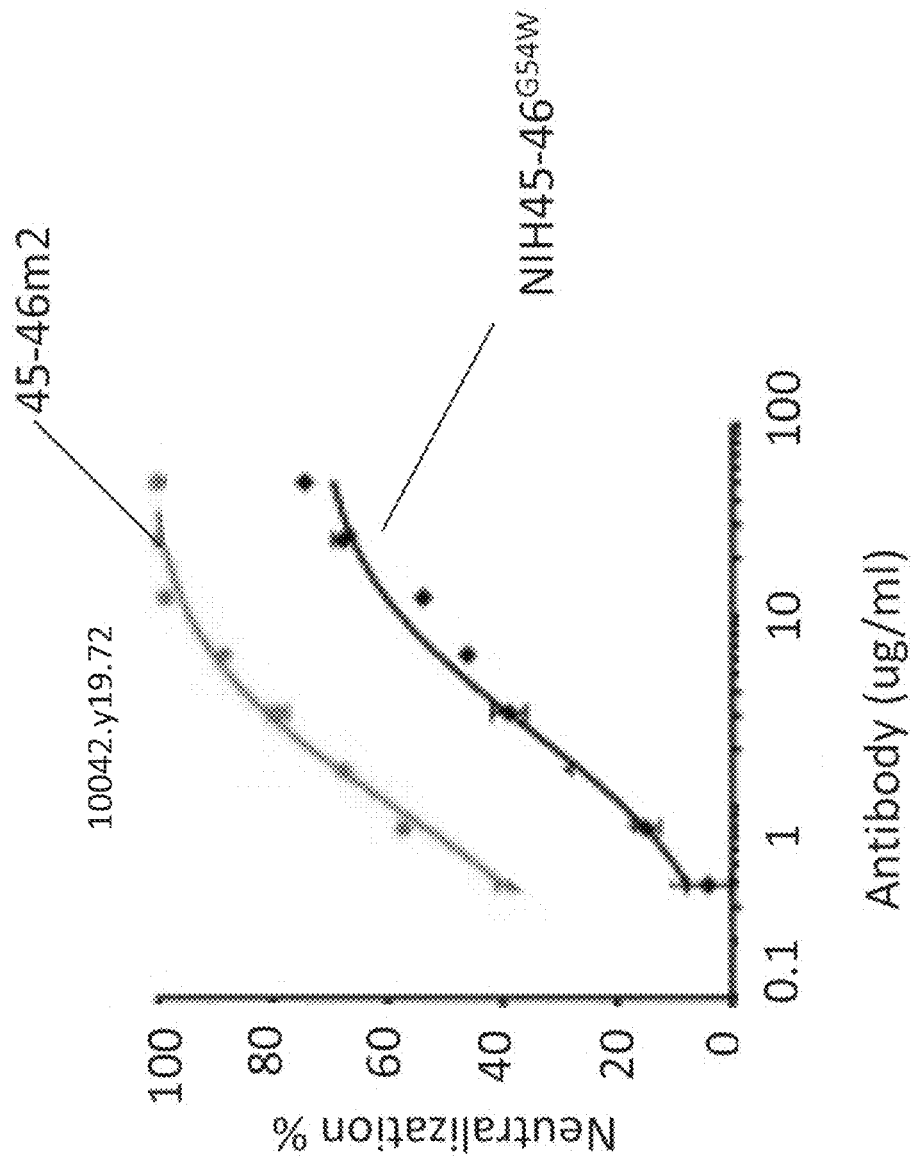

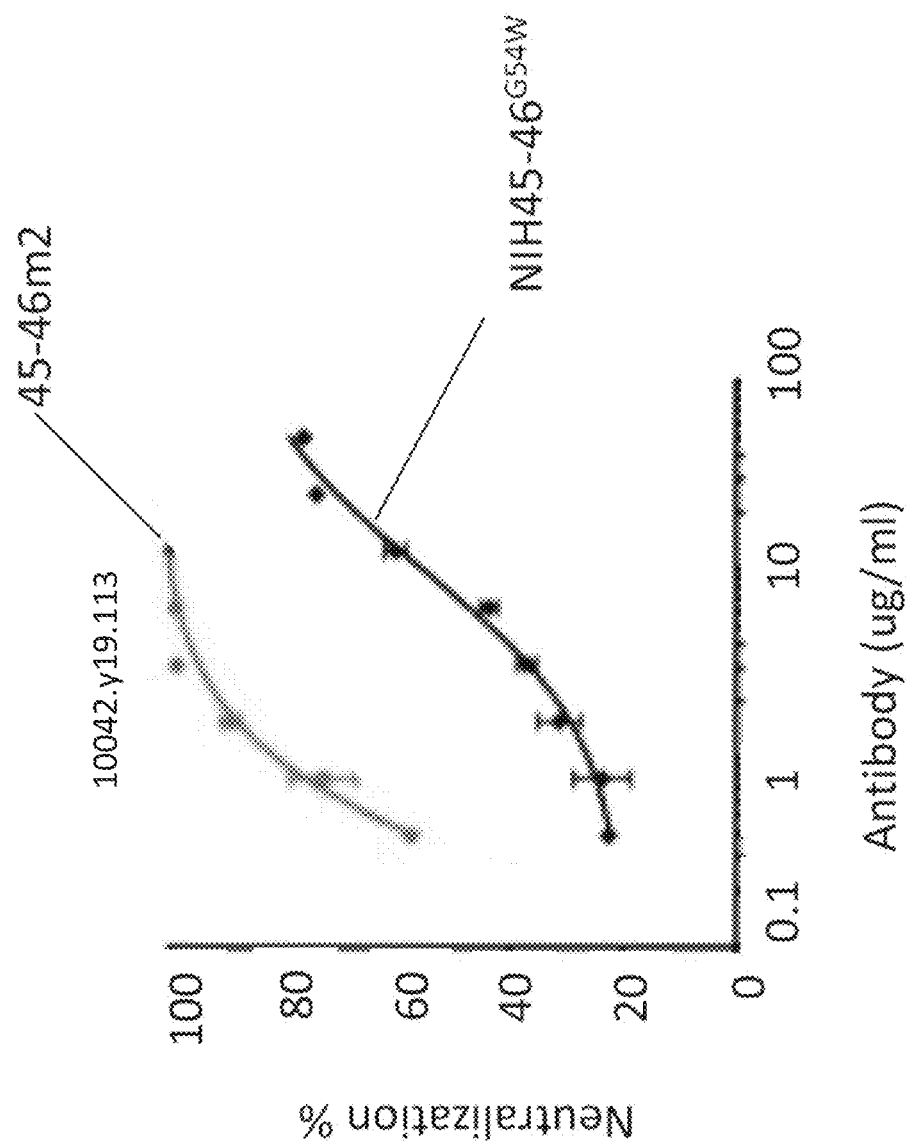

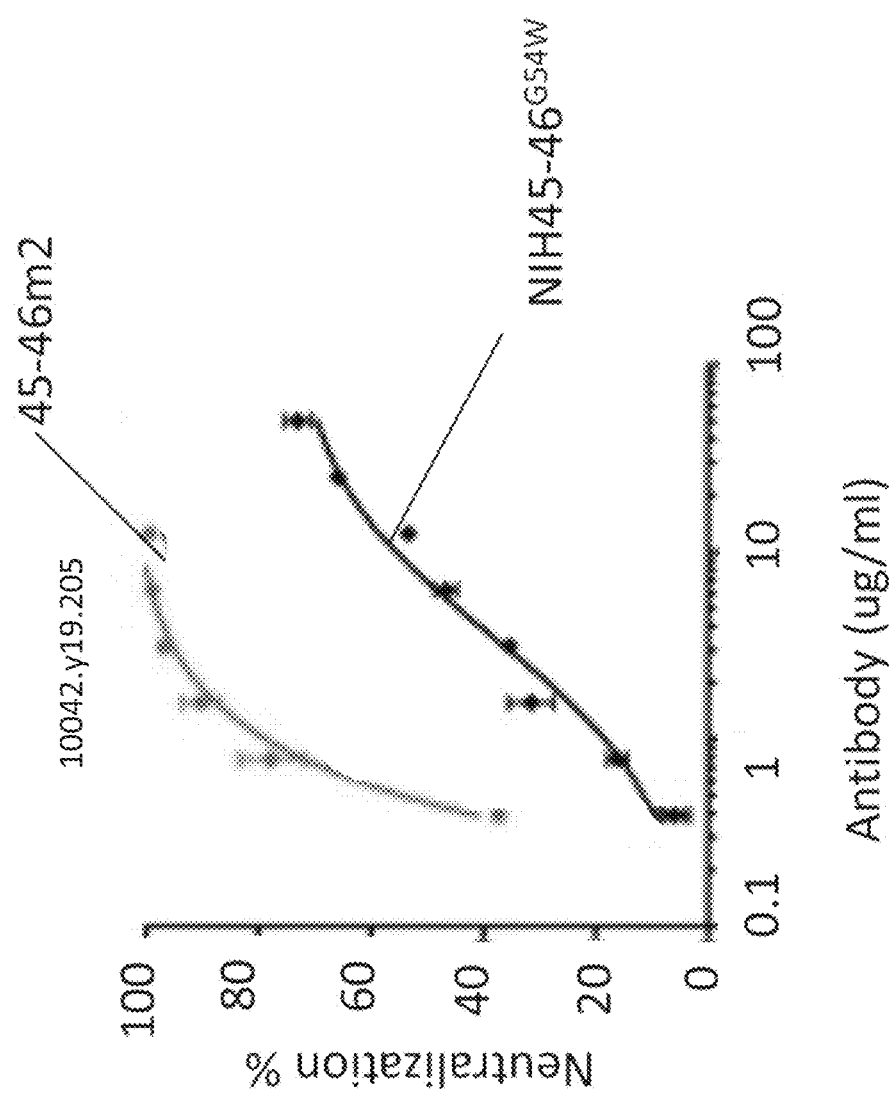

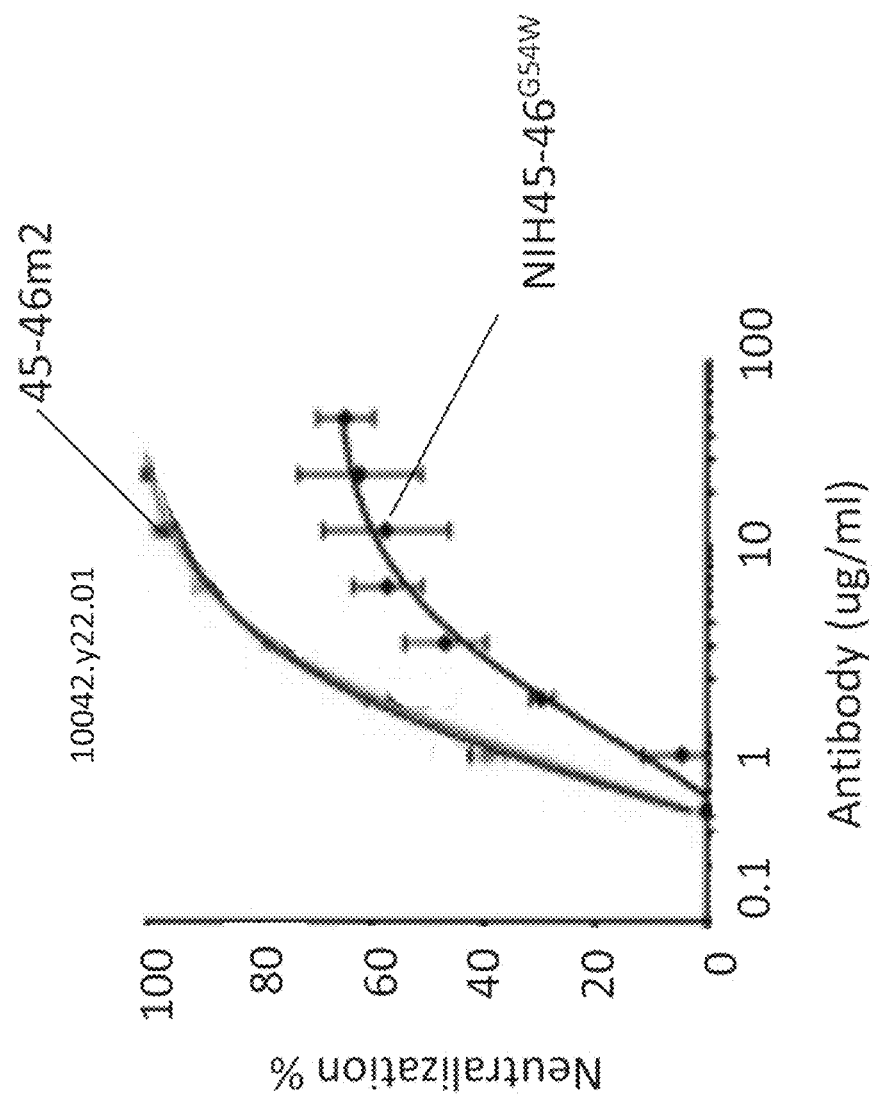

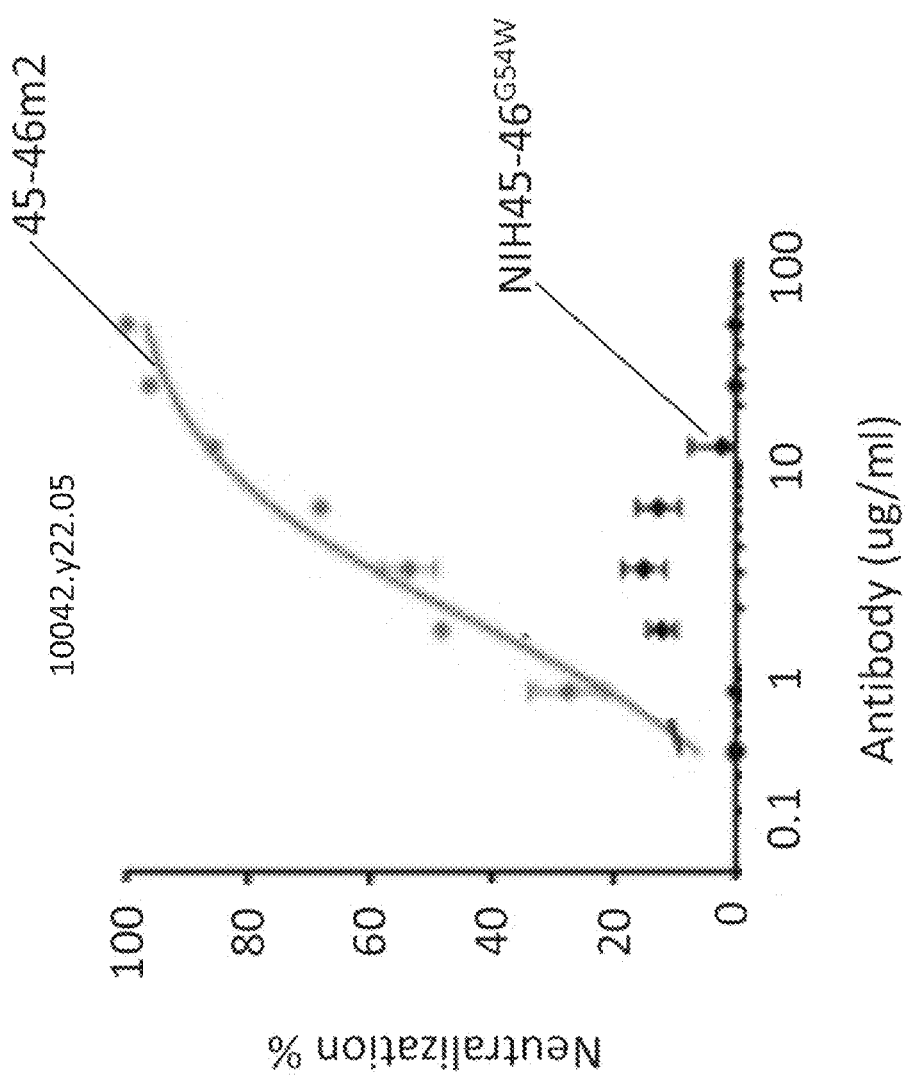

ANTIBODIES DIRECTED TOWARD THE HIV-1 GP120 CD4 BINDING SITE WITH INCREASED POTENCY AND BREADTH

CROSS-REFERENCE TO RELATED APPLICATION(S)

The present application claims priority to and the benefit of U.S. Provisional Application Ser. No. 61/570,173 filed on Dec. 13, 2011, and is continuation in part of U.S. patent application Ser. No. 13/558,312, filed Jul. 25, 2012, the entire contents of both of which are incorporated herein by reference.

STATEMENT REGARDING FEDERALLY SPONSORED RESEARCH OR DEVELOPMENT

This invention was made with government support under P01 A1081677-01, awarded by the National Institutes of Health. The government has certain rights in the invention.

INCORPORATION BY REFERENCE

The present application contains a Sequence Listing which has been submitted in ASCII format via EFS-Web and is hereby incorporated by reference in its entirety. Said ASCII copy, created on Jul. 25, 2012, is named 1358312SEQLISTING.txt, created Jul. 25, 2012 and being 47,972 bytes in size.

TECHNICAL FIELD

This application is directed to a gp120 anti-CD4 binding site (anti-CD4bs) antibody composition that has improved potency and breadth against the human immunodeficiency virus, (HIV) which causes acquired immunodeficiency syndrome (AIDS).

TECHNICAL BACKGROUND

Three decades after the emergence of HIV there is still no vaccine, and AIDS remains a threat to global public health. However, some HIV-infected individuals eventually develop broadly neutralizing antibodies (bNAbs), i.e., antibodies that neutralize a large panel of HIV viruses and that can delay viral rebound in HIV patients. Such antibodies are relevant to vaccine development, as evidenced by the prevention of infection observed after passive transfer to macaques. Antibodies obtained by recent methods target several epitopes on the viral spike gp120 protein. These antibodies show broad and potent activity, and are referred to as highly active agonistic anti-CD4 binding site antibodies (HAADs). HAADS mimic binding of the host receptor CD4 protein by exposing the co-receptor binding site on gp120. Despite isolation from different donors, HAADs are derived from two closely-related Ig $V_H$ genes that share gp120 contact residues (Sheid et al., 2011, *Science*, 333:1633-1637 and Zhou et al.; *Science*, 2010, 329: 811-817).

Structural analysis of gp120 complexed with VR001 (a highly potent and broad HAAD), and gp120 complexed with each of VRC03 and VRC-PG04, (two new CD4bs antibodies sharing the VRC01 germline $V_H$ gene) revealed convergence of gp120 recognition despite low sequence identities (48-57% in $V_H$; 62-65% in $V_L$) (Wu et al; 2011, *Science*, 333:1593-1602). However, sequence differences between these clonally-unrelated anti-CD4 antibodies make it difficult to determine the structural features that yield neutralization potency and breadth to thereby obtain a potent HIV antibody that is effective across many 111V strains.

SUMMARY

In some embodiments of the present invention, a composition includes an isolated anti-CD4 binding site (anti-CD4bs) potent VRC01-like (PVL) antibody having a heavy chain and a light chain. The heavy chain of the anti-CD4bs PVL antibody includes a heavy chain substitution at a position equivalent to Phe43 of a CD4 receptor protein. The heavy chain substitution is selected from hydrophobic amino acids, glycine, histidine, arginine, glutamine, asparagine, lysine, glutamic acid, and aspartic acid. In some embodiments, for example, the heavy chain substitution is tryptophan, tyrosine, phenylalanine, glycine, histidine, arginine, glutamine, or asparagine.

According to some embodiments of the present invention, the anti-CD4bs PVL, antibody also includes a light chain substitution of tyrosine for serine at position 28 of the light chain. The light chain may be selected from SEQ NOs: 1, 3, 5, 7, 9, 11, 13, 15, 17, 19, 21, 23, 25, 27, 29, 31, 33, 35, 37, 39, 41, and 43.

The position equivalent to Phe43 of the CD4 receptor protein may be position 54 of the heavy chain. Also, the heavy chain may be selected from SEQ ID NOs: 2, 4, 6, 8, 10, 12, 14, 16, 18, 20, 22, 24, 26, 28, 30, 32, 34, 36, 38, 40, 42, 44, 45, and 46.

The anti-CD4bs PVL antibody may be selected from VRC01, VRC02, NIH-45-46, 3BNC60, 3BNC117, 3BNC62, 3BNC95, 3BNC176, 12A21, VRC-PG04, VRC-CH30, VRC-CH31, VRC-CH32, VRC-CH33, VRC-CH34, VRC03 heavy chain with VRC01 light chain, gVRC-H5 (d74) heavy chain with VC-PG04 light chain, gVRC-H12 (d74) heavy chain with VRC-PG04 light chain, VRC03, VRC01 heavy chain with VRC03 light chain, 3BNC55, 3BNC91, 3BNC104, 3BNC89, 12A21, and VRC-PC104b. In some embodiments, for example, the anti-CD4bs PVL antibody may be NIH45-46.

According to some embodiments of the present invention, a nucleic acid molecule encodes the heavy chain and the light chain of the anti-CD4bs PVL antibody. The heavy chain of the anti-CD4bs PVL antibody encoded by the nucleic acid molecule includes a heavy chain substitution at a position equivalent to Phe43 of a CD4 receptor protein. The heavy chain substitution is selected from hydrophobic amino acids, glycine, histidine, arginine, glutamine, asparagine, lysine, glutamic acid, and aspartic acid. In some embodiments, for example, the heavy chain substitution is tryptophan, tyrosine, phenylalanine, glycine, histidine, arginine, glutamine, or asparagine.

In some embodiments, the light chain of the anti-CD4bs PVL antibody encoded by the nucleic acid molecule includes a light chain substitution of serine at position 28 of the light chain with tyrosine.

In some embodiments, a vector includes the nucleic acid molecule. In other embodiments, a cell includes the vector.

According to some embodiments of the present invention, a pharmaceutical composition includes the composition including the isolated anti-CD4bs PVL antibody, or a fragment thereof. The pharmaceutical composition further includes a pharmaceutically acceptable carrier. The anti-CD4bs PVL antibody has a heavy chain and a light chain. The heavy chain of the anti-CD4bs PVL antibody includes a heavy chain substitution at a position equivalent to Phe43 of a CD4 receptor protein. The heavy chain substitution is selected from hydrophobic amino acids, glycine, histidine, arginine, glutamine, asparagine, lysine, glutamic acid, and aspartic acid. In some embodiments, for example, the heavy chain substitution is tryptophan, tyrosine, phenylalanine, glycine, histidine, arginine, glutamine, or asparagine. The anti-CD4bs PVL antibody may also include a light chain substitution of tyrosine for serine at position 28 of the light chain.

In some embodiments of the present invention, a method of preventing or treating an HIV infection or an HIV-related disease includes administering a therapeutically effective amount of a composition including the anti-CD4bs PVL antibody having the heavy chain substitution. The anti-CD4bs PVL antibody may further include a light chain substitution of the serine at position 28 of the light chain with tyrosine.

According to other embodiments of the present invention, a method of increasing potency and breadth of an isolated anti-CD4bs PVL antibody having a heavy chain and a light chain includes identifying a target amino acid on the heavy chain that is at a position equivalent to Phe43 of a CD4 receptor protein, and substituting the target amino acid with a heavy chain substitution selected from hydrophobic amino acids, glycine, histidine, arginine, glutamine, asparagine, lysine, glutamic acid and aspartic acid. For example, the heavy chain substitution ma include phenylalanine, tryptophan, tyrosine, glycine, histidine, arginine, glutamine or asparagine. The position equivalent to Phe43 of the CD4 receptor protein may be position 54 of the heavy chain. The method may further include substituting serine at position 28 of the light chain with tyrosine.

BRIEF DESCRIPTION OF THE DRAWINGS

The patent or application file contains at least one drawing executed in color. Copies of this patent or patent application publication with color drawings will be provided by the Office upon request and payment of the necessary fee.

These and other features and advantages of the present invention will be better understood by reference to the following detailed description when considered in conjunction with the accompanying drawings.

FIG. 1A is a superimposition of a structural depiction of NIH45-46 Fab alone (in blue) and of NIH45-46-gp120 complex (in magenta), according to embodiments of the present invention.

FIG. 1B is a structural depiction of NIH45-46-gp120 (93TH053) complex and the binding interface and domains labeled and colored as indicated, with NIH45-46 Fab shown in magenta (heavy chain) and light purple (light chain), and gp120 shown in yellow (inner domain) and grey (outer domain), according to embodiments of the present invention.

FIG. 2 is a table of the data and refinement statistics from the x-ray diffraction data collected from the NIH45-46 Fab crystal structure and the NIH45-46-gp120 (93TH-057) complex as depicted in FIGS. 1A and 1B, according to embodiments of the present invention.

FIG. 3A is a sequence alignment of the heavy chain variable ($V_H$) domains of NIH45-46 (SEQ ID NO: 6) and VRC01 (SEQ ID NO: 2) antibodies, in which the open circles indicate NIH45-46 side chain residues that contact gp120 and closed circles indicate NIH45-46 main-chain, or main-chain and side chain residues that contact gp120, according to embodiments of the present invention.

FIG. 3B is a sequence alignment of the light chain variable ($V_L$) domains of NIH45-46 (SEQ ID NO: 5) and VRC01 (SEQ ID NO: 1) antibodies, in which the open circles indicate NIH45-46 side chain residues that contact gp120 and closed circles indicate NIH45-46 main-chain, or main-chain and side chain residues that contact gp120, according to embodiments of the present invention.

FIG. 4A is a superimposition and comparison of a structural depiction of NIH45-46-gp120 complex (shown in magenta) and a structural depiction of VRC01-gp120 complex (shown in blue), according to embodiments of the present invention.

FIG. 4B is close-up view of the conserved interactions in the gp120 contacts of NIH45-46 and VRC01, with the CD4 binding loop of gp120 labeled and shown in yellow, according to embodiments of the present invention.

FIG. 5 is a depiction of the interactions of NIH45-46-gp120 complex and VRC01-gp120 complex with NIH45-46 shown in magenta, VRC01 in blue, and domains of gp120 shown as follows: outer domain (yellow), bridging sheet (orange), CD4 binding loop (blue), V5 loop and D Loop (green), and inner domain (grey); with the contact region between CDRH3 insertion residues of NIH45-46 and gp120 shown in the close-up box with insertion residues 99a-99b labeled alphabetically, according to embodiments of the present invention.

FIG. 6A is a structural depiction of the binding interface of a NIH45-46-gp120 complex characterized by the direct hydrogen bond (dotted line) between the main-chain atom of $Gly54_{NIH45\text{-}46}$ (magenta) and $Asp368_{gp120}$ (gray) and two water molecules (larger spheres in dotted line), according to aspects of the present invention.

FIG. 6B is a structural depiction of the contact interface of a CD4-gp120 complex, characterized by CD4 (yellow) forming two direct hydrogen bonds (dotted lines) with the CD4-binding loop on gp120, according to embodiments of the present invention.

FIG. 6C is a structural depiction of the contact interface of a VRC03-gp120 complex, characterized by a carbonyl oxygen of $Trp54_{VRC03}$ forming a hydrogen bond with $Asp368_{gp120}$, according to embodiments of the present invention.

FIG. 7 is a structural depiction of the binding interface of a NIH45-46-gp120 complex, as shown by a hydrogen bond network between the main-chain carbonyl oxygen of $Ala281_{gp120}$, $Tyr99d_{NIH45\text{-}46}$ in CDRH-3, and $Lys52_{NIH45\text{-}46}$ in CDRH2, in which yellow dots represent hydrogen bonds, and as shown in the inset box: a sulfate ion (yellow) substitutes for $Ala281_{gp120}$ the unbound NIH45-46, according to embodiments of the present invention.

FIG. 8 is a structural depiction of the binding interface of a NIH45-46-gp120 complex, as shown by the electrostatic interactions between $Asp99c_{NIH45\text{-}46}$ and $Lys97_{gp120}$ (lower left dotted line) and hydrogen bonds between $Asp99c_{NIH45\text{-}46}$-$Tyr97_{NIH45\text{-}46}$ (upper left dotted line) and $Arg99b_{NIH45\text{-}46}$-$Asn99_{gp120}$ (lower right dotted line), according to embodiments of the present invention.

FIG. 9A is a structural depiction of NIH45-46-gp120 complex (with NIH45-46 shown in magenta and gp120 shown in grey) superimposed with a structural depiction of CD4-gp120 complex (with CD4 shown in yellow and gp120 shown in orange), with an arrow and label of Phe43 of CD4, according to embodiments of the present invention.

FIG. 9B is a close-up view of the superimposition of FIG. 9A with the CDRH2 loop of NIH45-46 (magenta) and the CDR2-like loop of CD4 (yellow) interacting with gp120 (grey surface), according to embodiments of the present invention.

FIG. 9C is a structural depiction of a CD4-gp120 (ZM135M.PL10a) complex with the contact interface labeled and colored as in FIG. 1B, and the initial site of CD4 attachment is indicated with the oval, according to embodiments of the present invention.

Figure 11A:
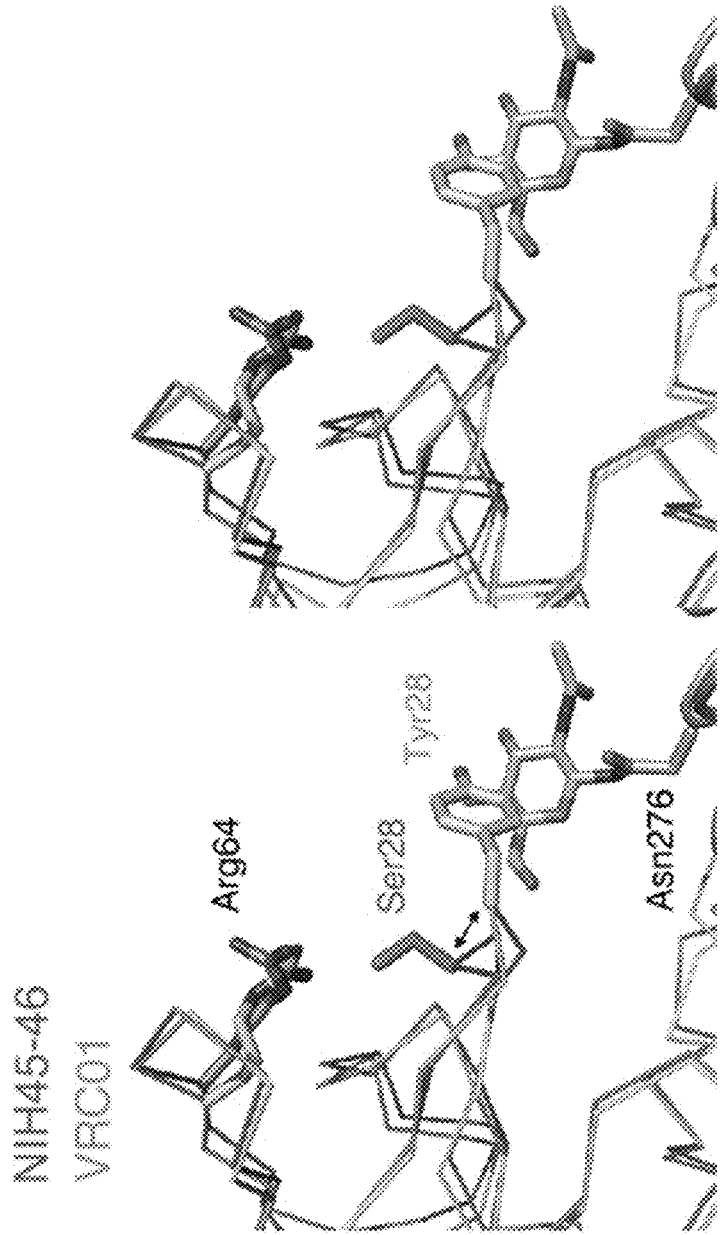

FIG. 11A is a stereo view of a structural depiction of a NIH45-46-gp120 complex superimposed with a VRC01-gp120 complex showing that Tyr28$_{VRC01\ LC}$ interacts with an N-linked carbohydrate attached to Asn276$_{120}$ and the side chain counterpart residue Ser28$_{NIH45-46}$ in the NIH45-46 complex faces away from gp120 to hydrogen bond with Arg64$_{NIH45-46\ LC}$ (the arrowheads point to Cα atoms of residue 28 in each structure), according to embodiments of the present invention.

Figure 11B:
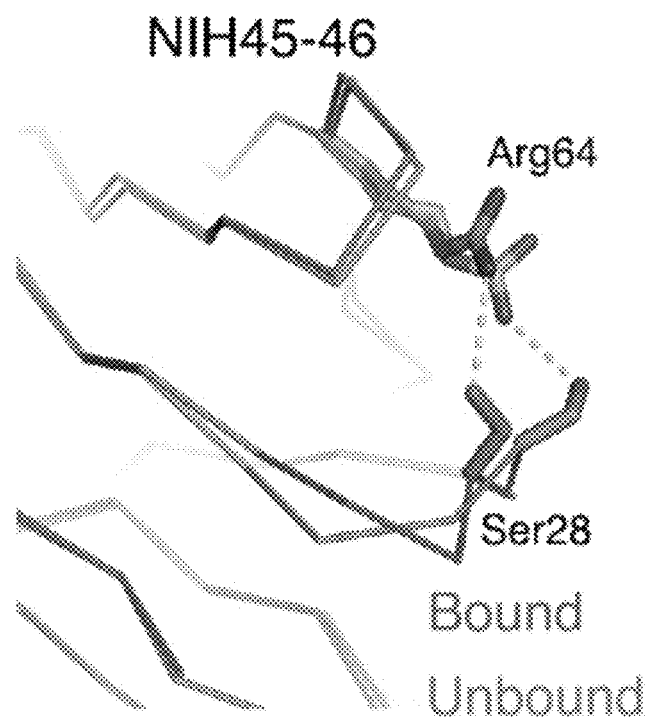

FIG. 11B is a superimposition of NIH45-46LC bound to gp120 (magenta) and unbound (green) showing the hydrogen bonds between Ser28 and Arg64, according to embodiments of the present invention.

Figure 1A:
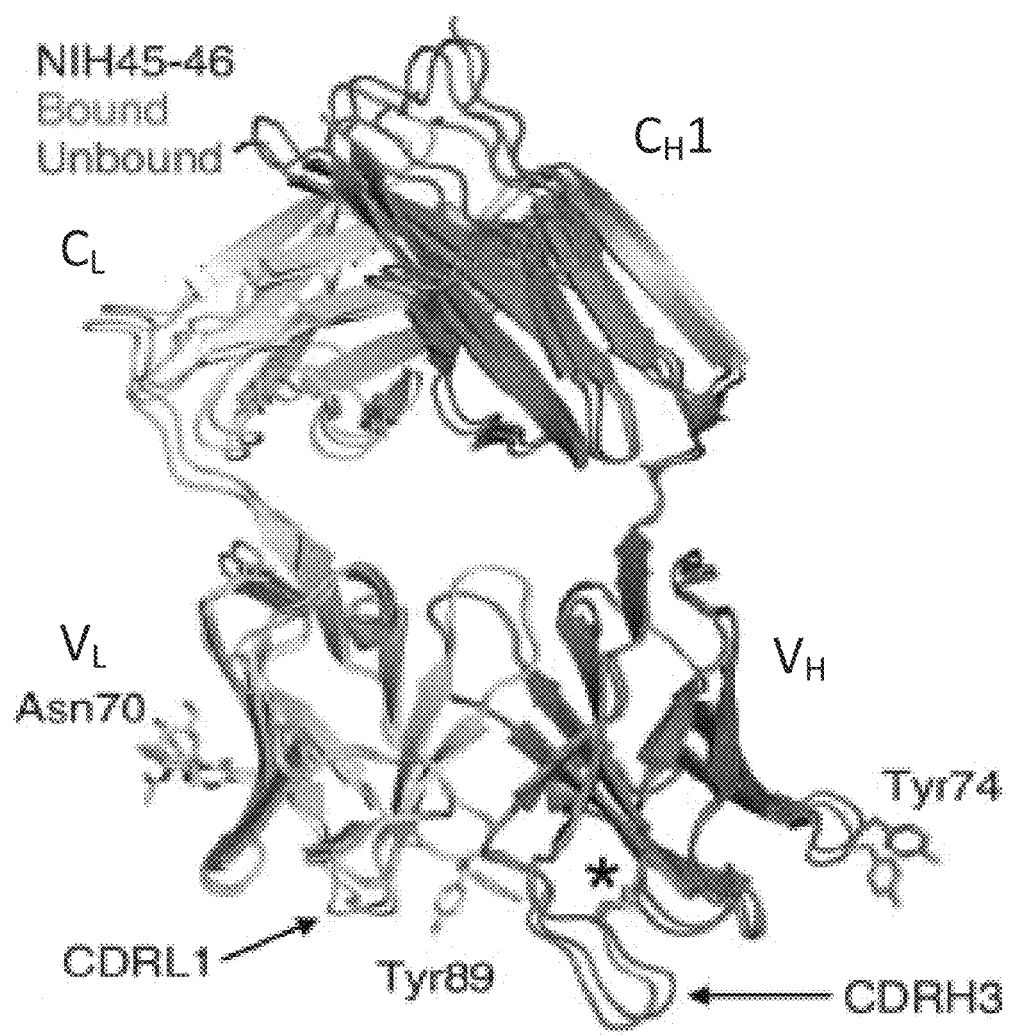
Figure 1B:
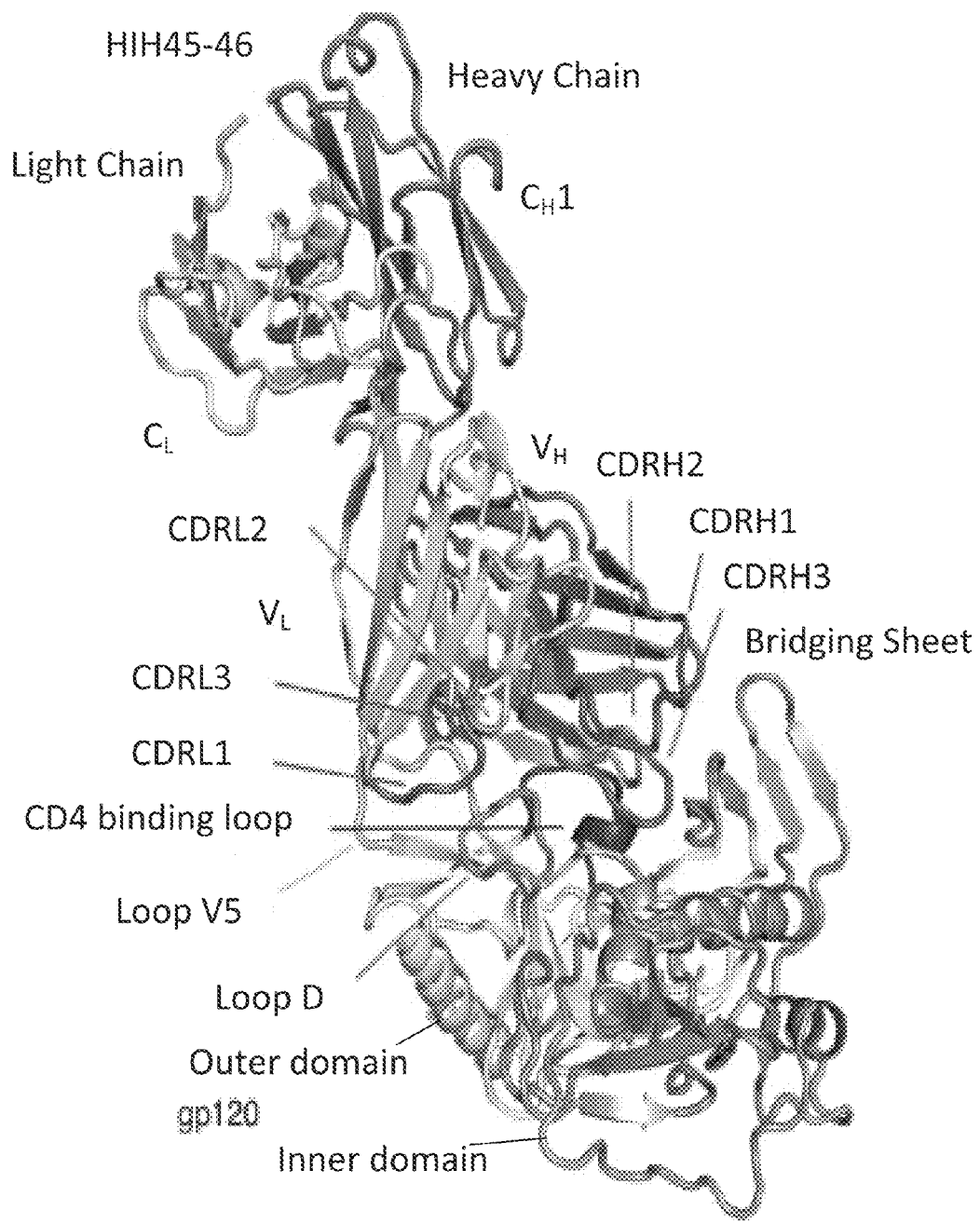
Figure 12:
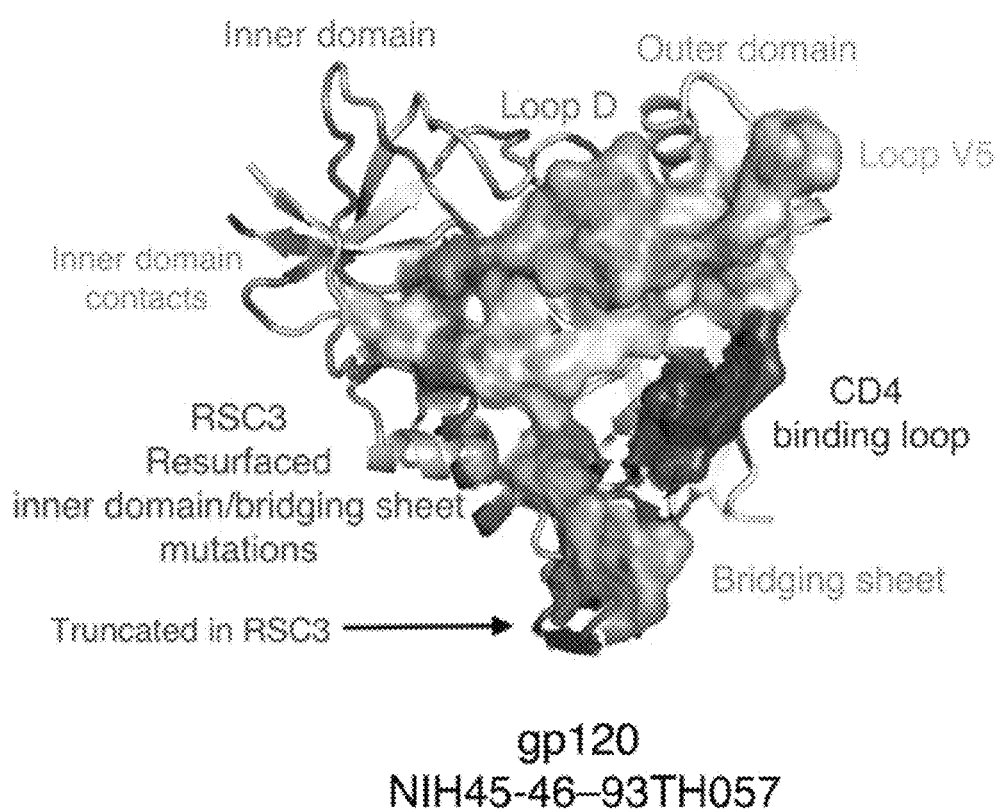

FIG. 12 is a structural depiction of gp12 and highlighted differences in the gp1.20 resurfaced stabilized core 3 (RSC3) variant, in which the NIH45-46 contact surfaces are shown and the RSC3 mutations shown, with labeling and coloring as in FIG. 1B, according to embodiments of the present invention.

Figure 13A:
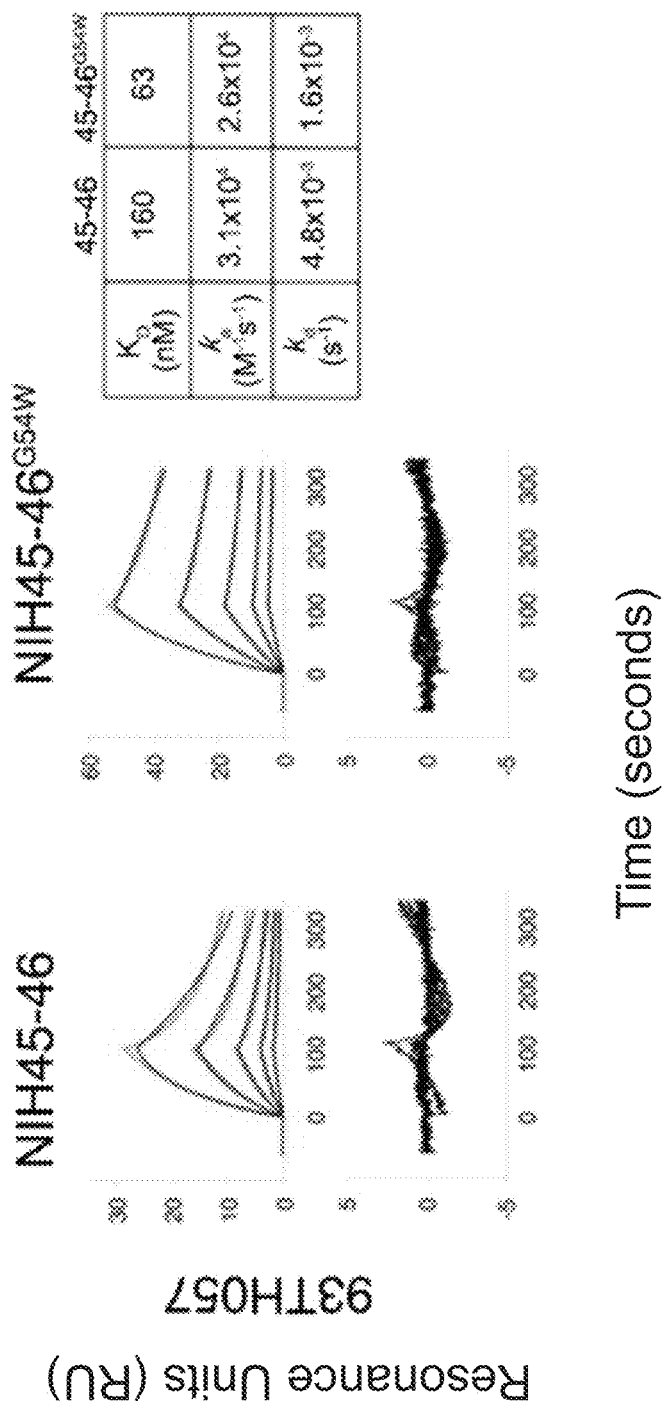

FIG. 13A shows sensorgrams from surface plasmon resonance (SPR) experiments of binding experiments of the 93TH057 gp120 protein with NIH45-46 and NIH45-46$^{G54W}$ Fabs, as indicated, and a table of the $K_D$ values is shown, according to embodiments of the present invention.

FIG. 13B shows sensorgrams from surface plasmon resonance (SPR) experiments of binding experiments of the CAP244.2.00 D3 gp120 protein with NIH45-46 and NIH45-46$^{G54W}$ Fabs, as indicated, and a table of the $K_D$ values is shown, according to embodiments of the present invention.

Figure 13C:
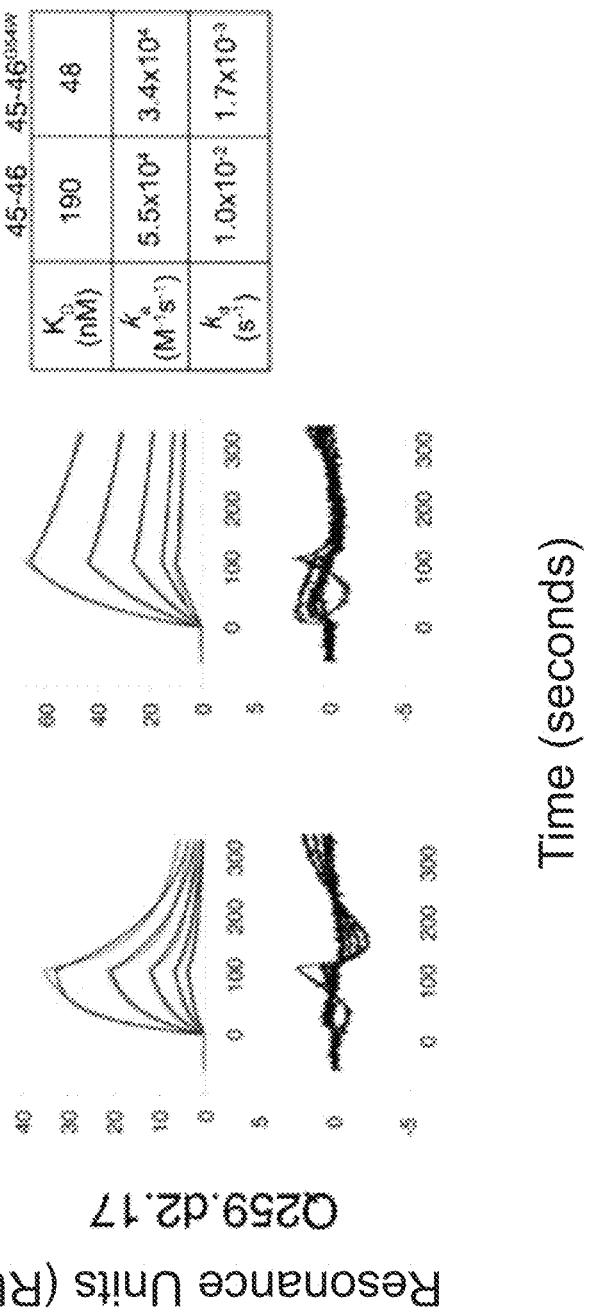

FIG. 13C shows sensorgrams from surface plasmon resonance (SPR) experiments of binding experiments of the Q259.d2.17 gp120 protein with NIH45-46 and NIH45-46$^{G54W}$ Fabs, as indicated, and a table of the $K_D$ values is shown, according to embodiments of the present invention.

Figure 14:
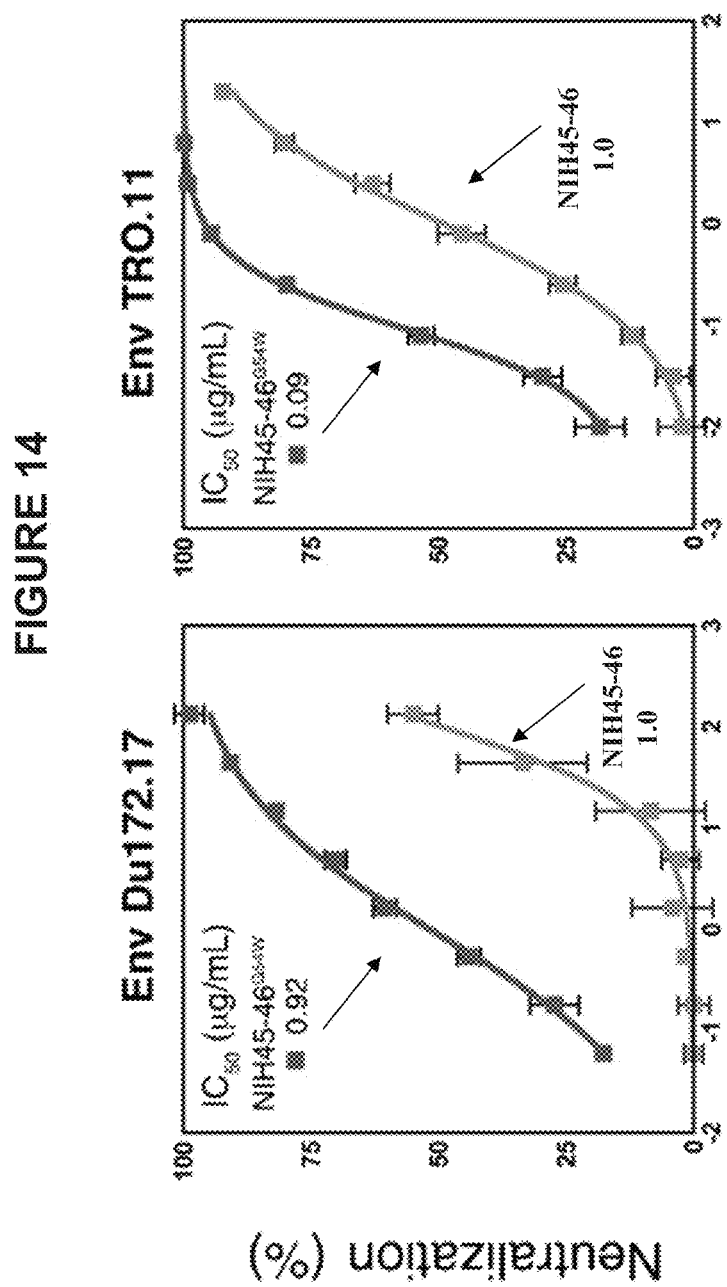

FIG. 14 shows neutralization curves for NIH45-46$^{G54W}$ and NIH45-46 in strains DU172.17 and TRO.11, as indicated, according to embodiments of the present invention.

Figure 15A:
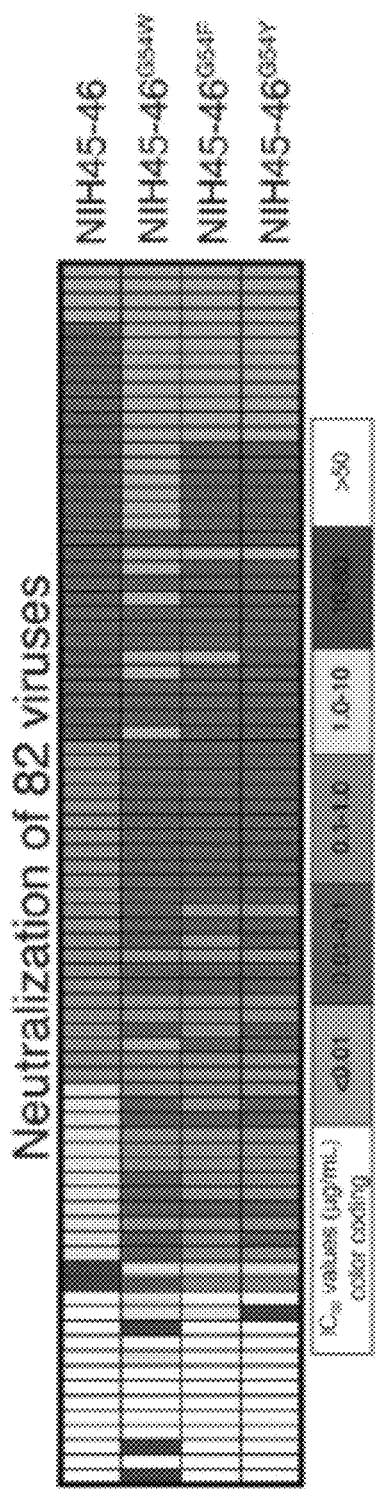

FIG. 15A shows a schematic comparing neutralization potencies of NIH45-46, NIH45-46$^{G54W}$, NIH45-46$^{G54F}$, and NIH45-46$^{G54Y}$, with IC$_{50}$ values for each color-coded as shown, according to embodiments of the present invention.

Figure 15B:
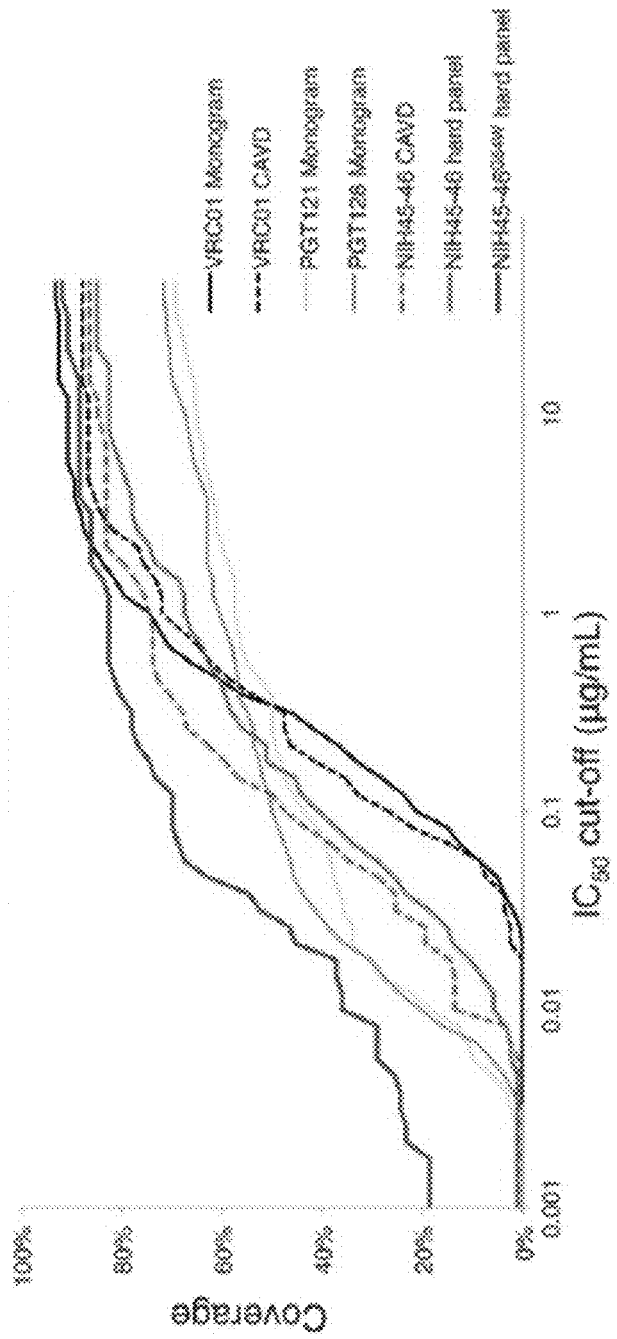

FIG. 15B shows a graphical comparison of neutralization coverage and potency for VRC01. Monogram (Monogram is a panel of 162 viral strains), VRC01 CAVD (CAVD is a panel of 118 viral strains), PGT121 Monogram, PGT128 Monogram, NIH45-46 CAVD, NIH45-46 hard panel (See Tables 7 and 8), and NIH45-46G54W hard panel, according to embodiments of the present invention.

Figure 15C:
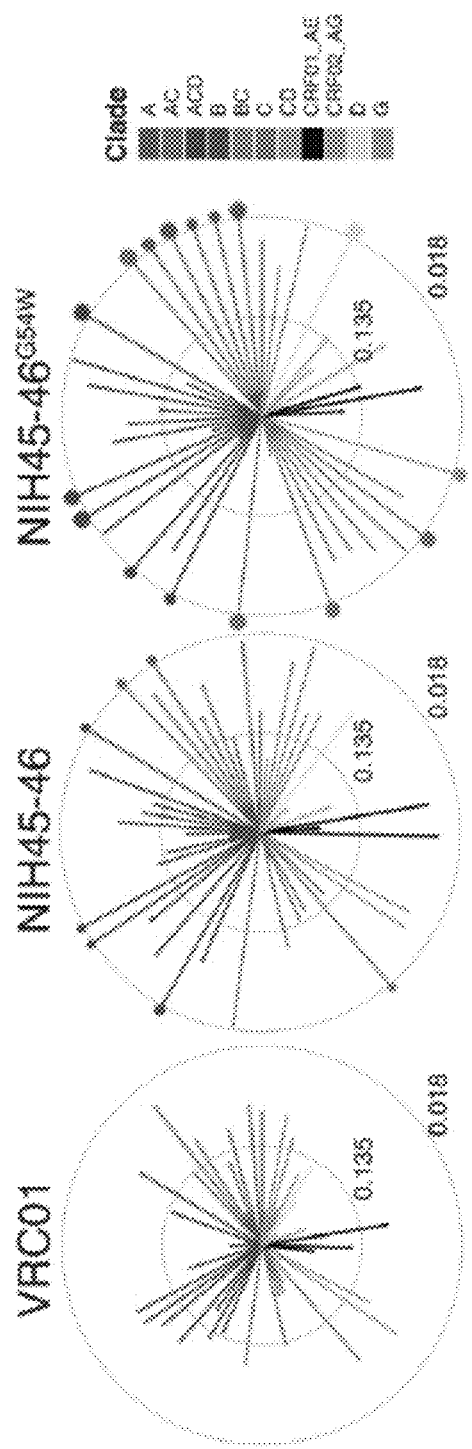

FIG. 15C shows neutralization summary spider graphs comparing IC$_{50}$ values for VRC01, NIH45-46, and NIH45-46$^{G54W}$ for 65 common viruses, in which each color represents a different HIV clade, the length of the lines and size of circles are inversely proportional to the IC$_{50}$ value, the distance between the outer and the inner circle and the distance from the inner circle to the center of a spider graph each span two natural logs in IC$_{50}$ concentration, the dots on the outer circle indicate strains with IC$_{50}$ values less than 0.018 μg/ml whose lines were truncated in the graph, and the size of each dot is inversely proportional to the IC$_{50}$ value, according to embodiments of the present invention.

Figure 16:
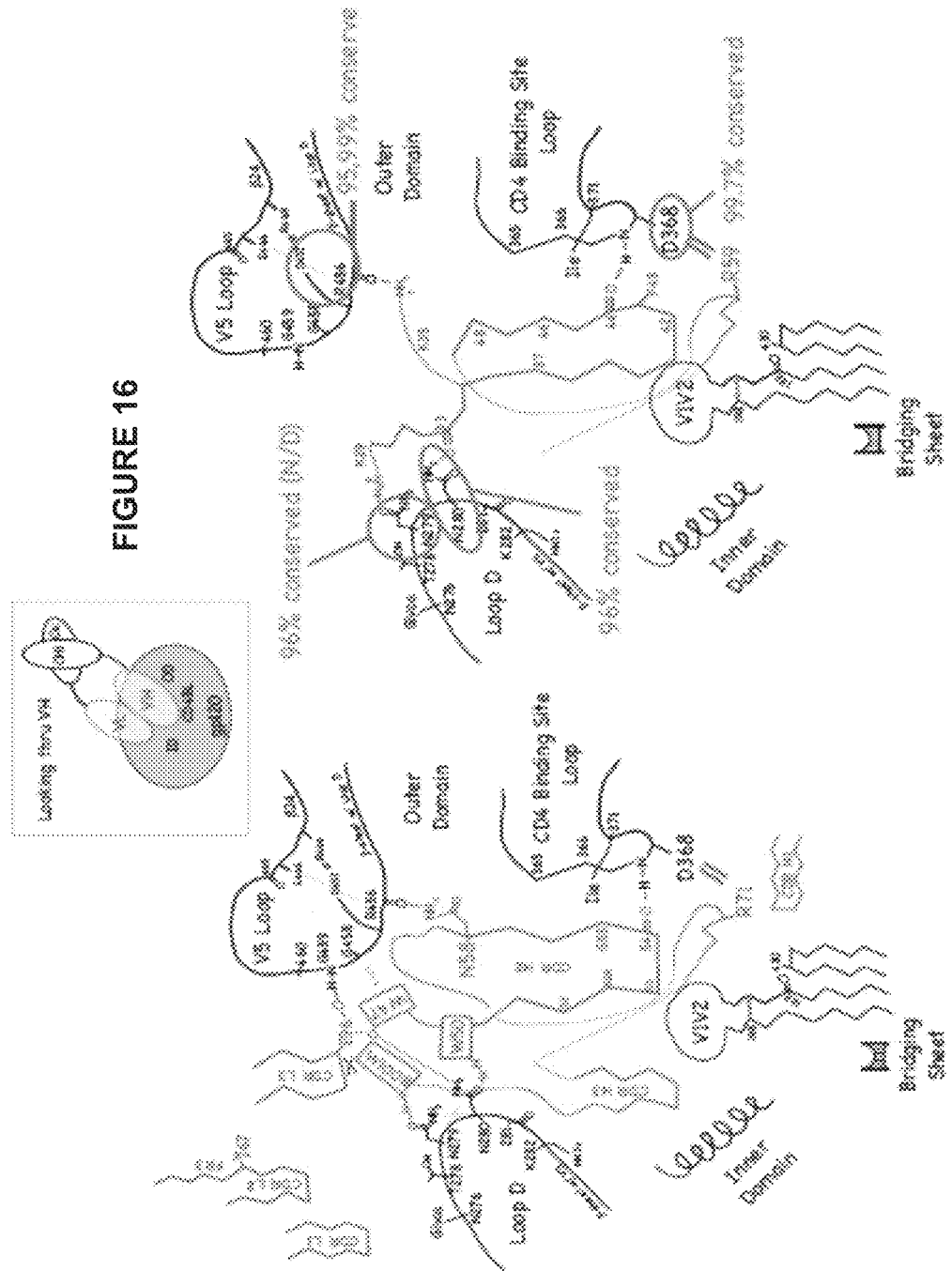

FIG. 16 is a schematic illustration of, on the left: antibody interactions (magenta and blue-gray) made with gp120 (black); and on the right: CD4 (magenta) with gp120 (black), with the viewpoint of the diagram shown in the inset box, according to embodiments of the present invention.

Figure 17:
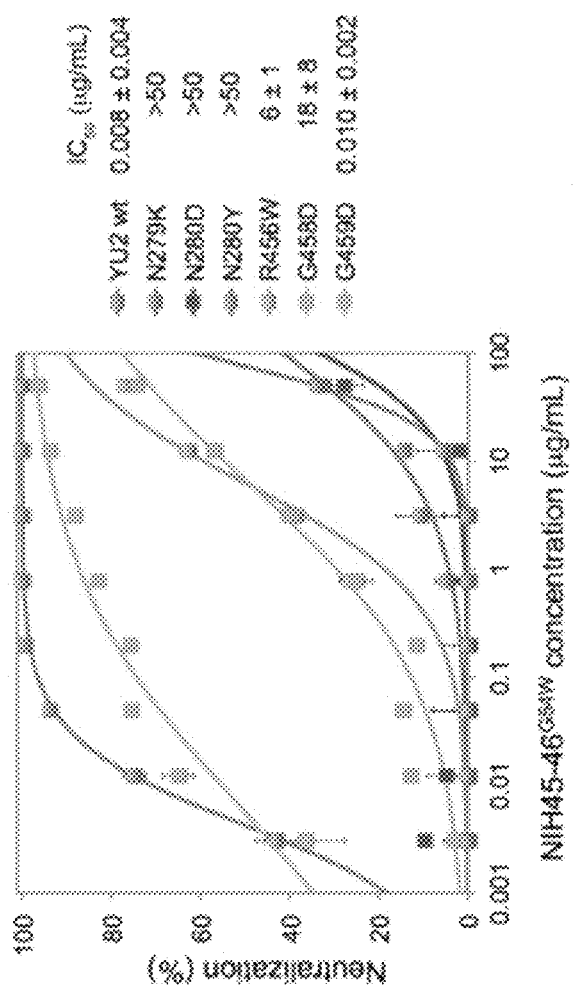

FIG. 17 is a graph of a neutralization assay showing the effects of mutations at critical residues in YU2 gp120 on neutralization by PVL antibody NIH45-46$^{G54W}$ in which the IC$_{50}$ values are the mean of several independent experiments, and the graph shows one experiment, according to embodiments of the present invention.

Figure 18:
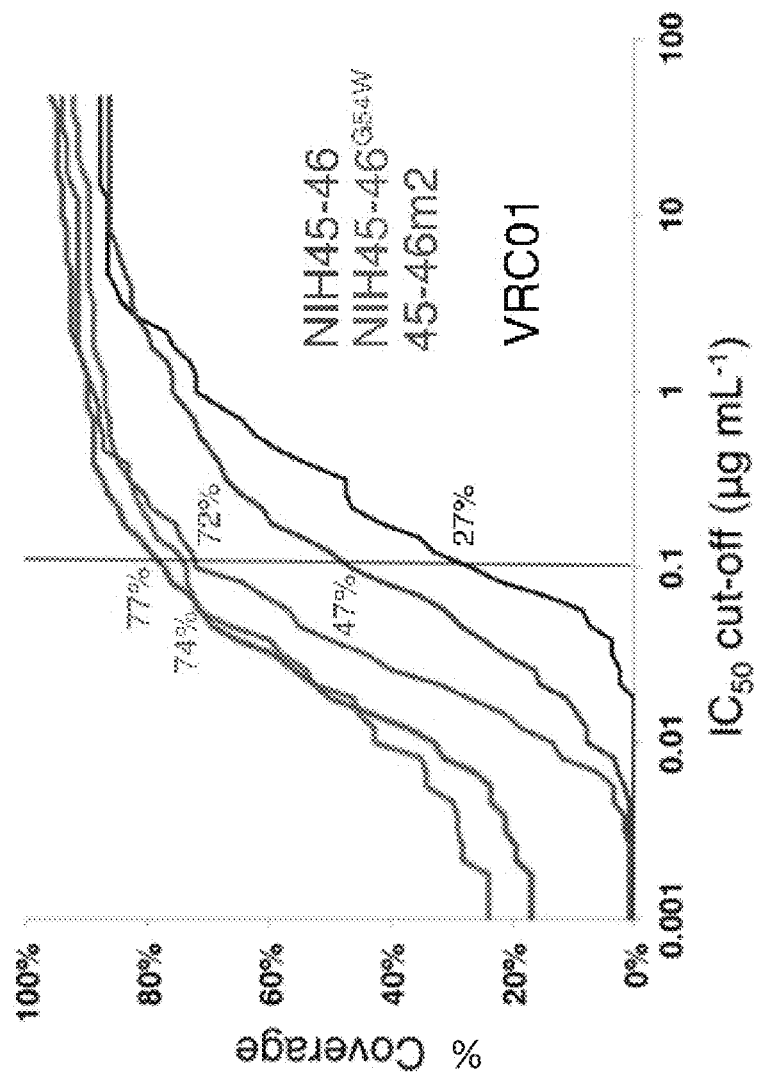

FIG. 18 is a graph of the breadth of neutralization (% COVERAGE) against a cross-clade panel of 118 primary HIV isolates as a function of IC$_{50}$ cut off (ug/ml$^{-1}$), according to embodiments of the present invention.

Figure 19:
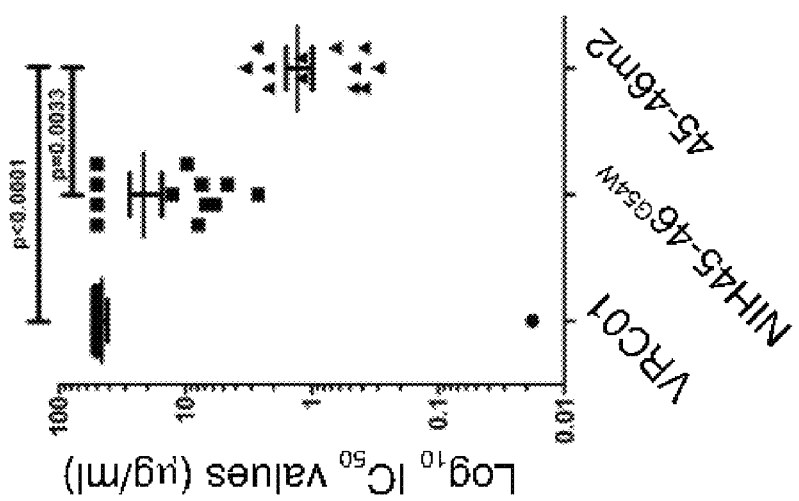

FIG. 19 is a graph showing the neutralization of VC100 clones shown as the log of the IC$_{50}$ values (ug/ml) for each of VRC01 antibody, NIH45-46$^{G54W}$ antibody and 45-46 m2 antibody, according to embodiments of the present invention.

Figure 20E:
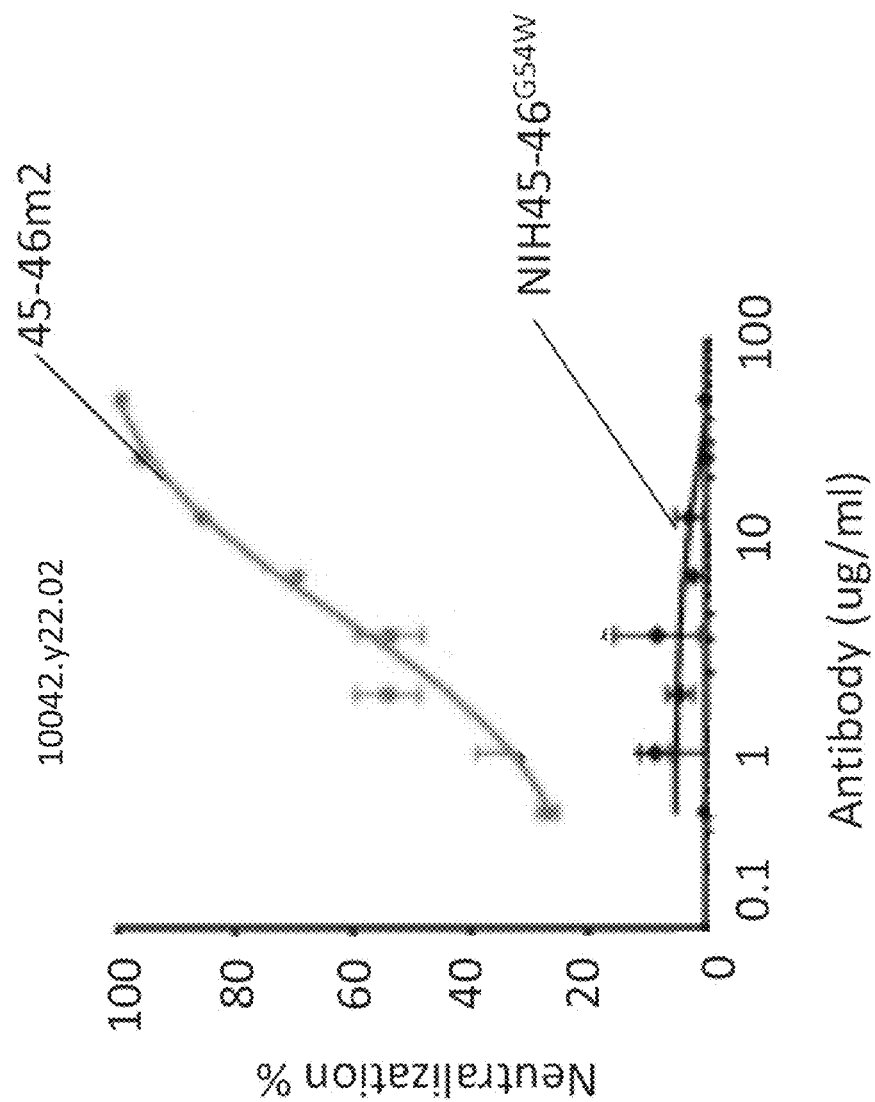
Figure 20F:
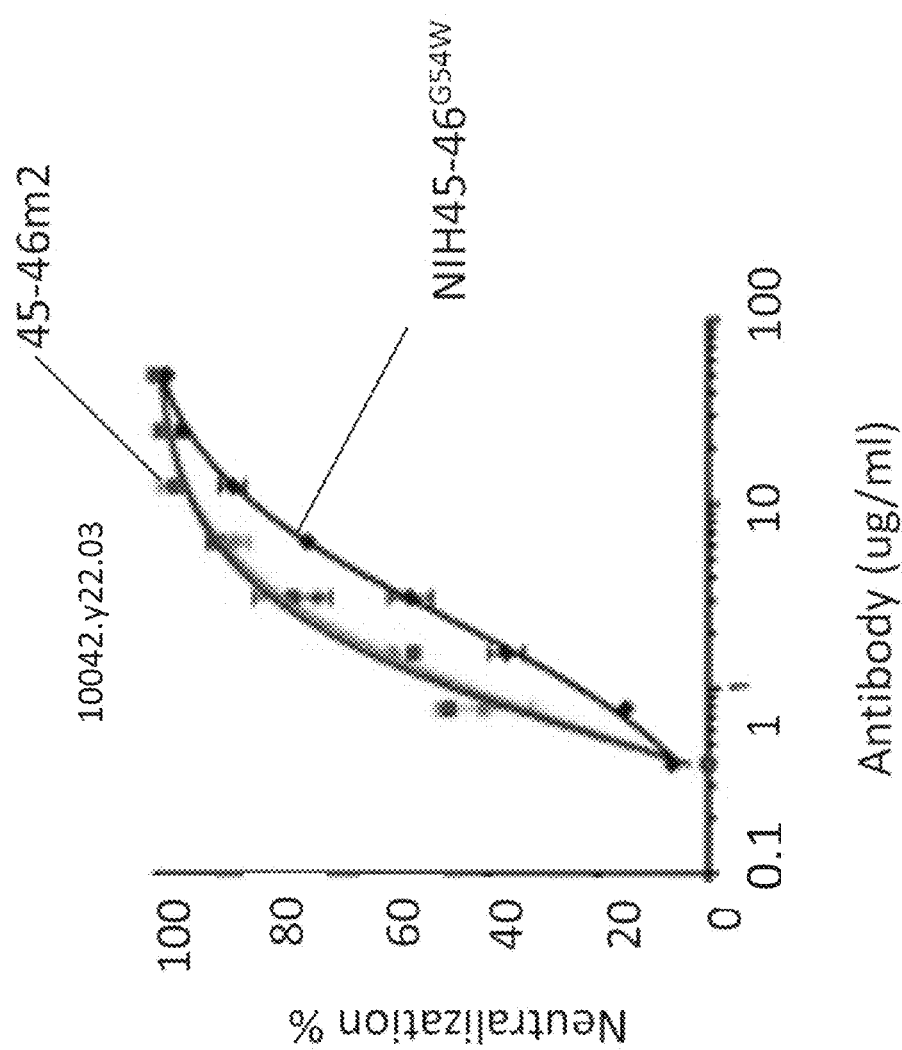
Figure 20H:
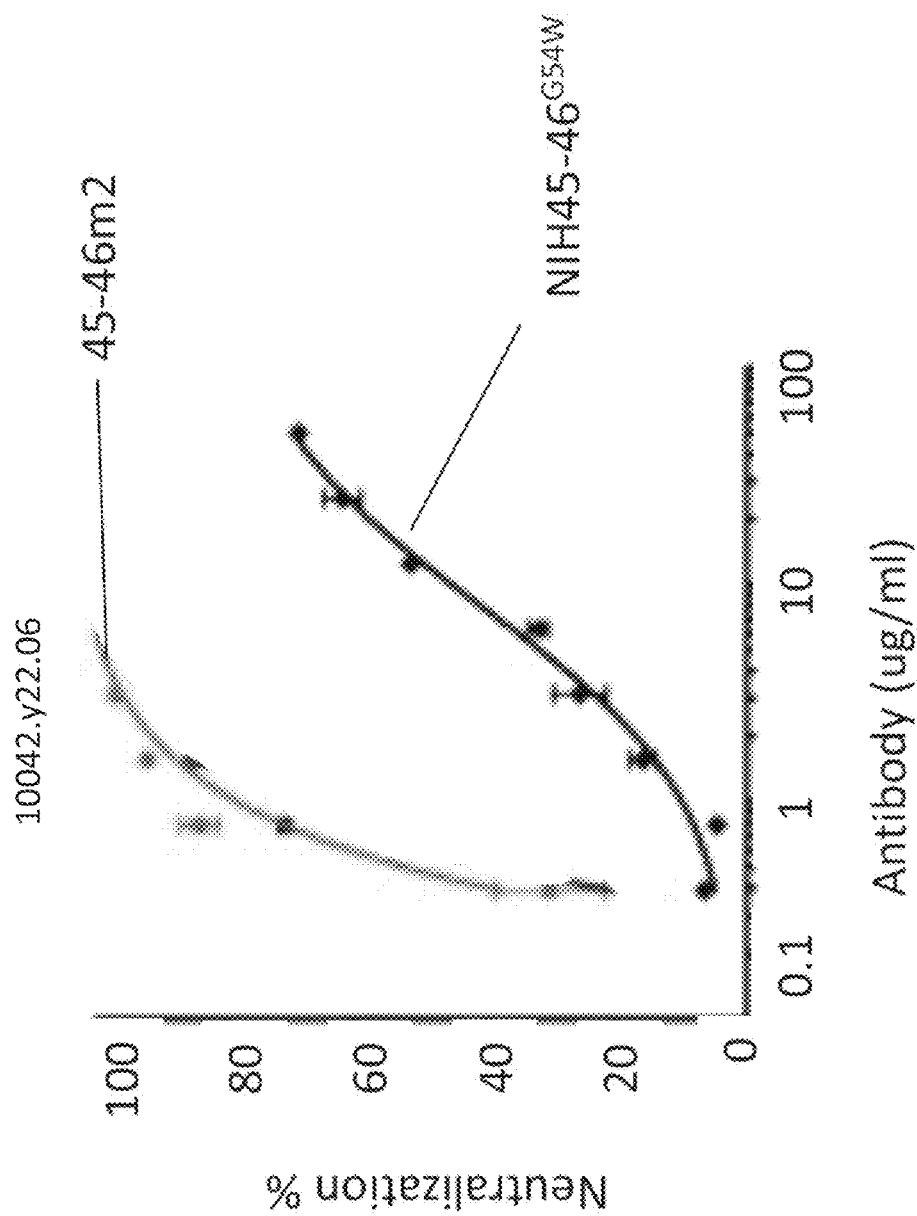
Figure 20I:
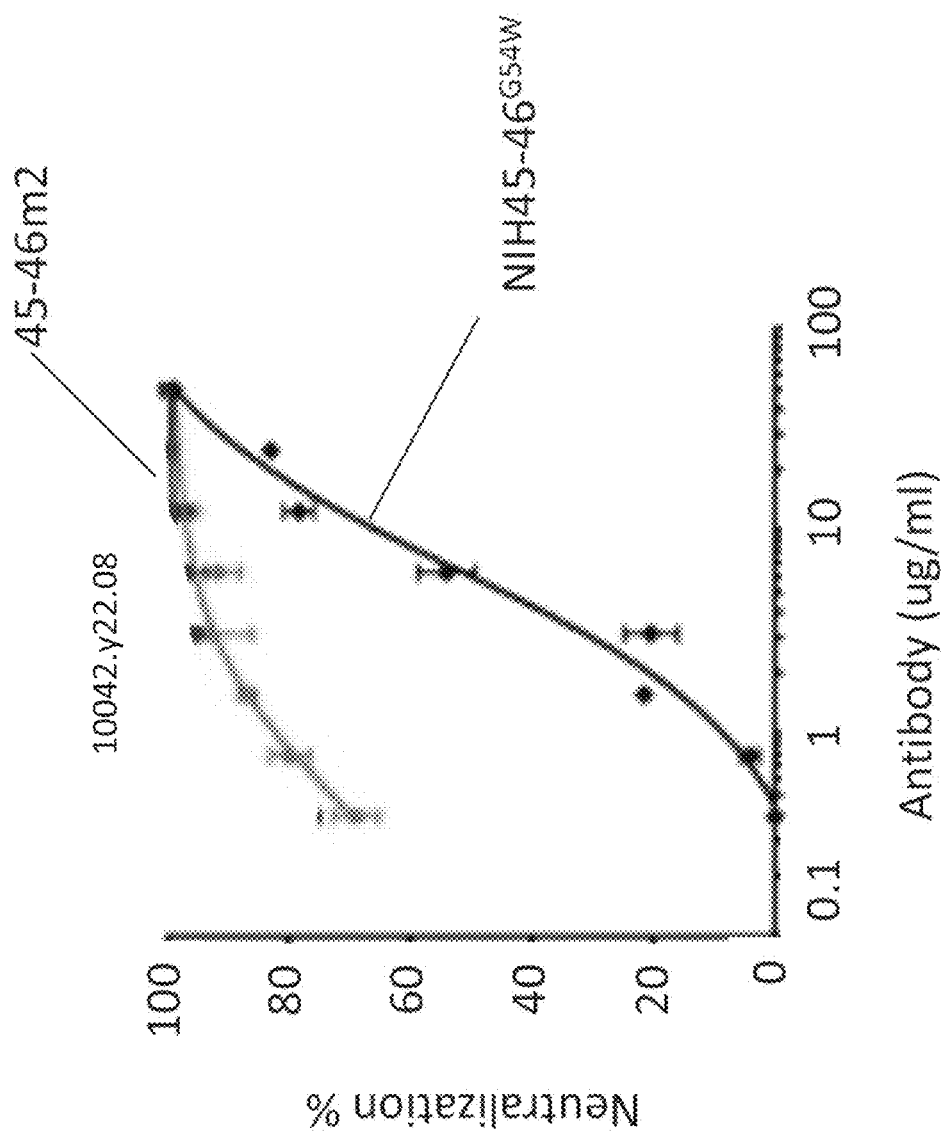

FIGS. 20A-20I are graphs showing the percent (%) neutralization of 10 viral clones from patient VC10042 using NIH45-46$^{G54W}$ antibody and 45-46 m2 antibody, in which FIGS. 20A, 20B, and 20C are from the indicated clones isolated 19 years post-infection, and FIGS. 20D, 20E, 20F, 20G, 20H, 20I are from the indicated clones isolated 22 years post-infection, according to embodiments of the present invention.

DETAILED DESCRIPTION

Aspects of the present invention are directed to anti-CD4 binding site (CD4bs) antibodies. Embodiments of the present invention include anti-CD4bs antibodies which are potent VRC01-like (PVL) antibodies as defined herein. In some embodiments of the present invention, an anti-CD4bs PVL antibody having a substitution at the amino acid position that is equivalent to phenylalanine at position 43 (Phe43) of the host CD4 receptor protein (CD4), in which the substitution is a hydrophobic amino acid, histidine, glycine, arginine, glutamine, asparagine, lysine, glutamic acid, and aspartic acid.

In some embodiments of the present invention, a method for increasing the potency and breadth of a PVL antibody includes identifying a target amino acid at the position on the heavy chain of the PVL antibody that is equivalent to Phe43 on CD4, and substituting the target amino acid with a hydrophobic amino acid, histidine; glycine, arginine, glutamine, asparagine, lysine, glutamic acid; and aspartic acid. For example, in the PVL antibody, NIH45-46; glycine at position 54 (Gly54) is in the Phe43-equivalent position, and substitution of Gly54 in NIH45-46 (Gly54$_{NIH45-46}$) with a hydrophobic amino acid such as tryptophan, results in which has increased potency and breadth compared to NIH45-46. Also, in the PVL antibody, 3BNC60; threonine at position 54 (Thr54) is in the Phe43-equivalent position, and substitution of Thr54 in 3BNC60 with, for example, glycine, histidine; or alanine, results in 3BNC60$_{T54G}$, 3BCN60$_{T54H}$, and 3BNC60$_{T54A}$, respectively, each of which has increased potency and breadth compared to 3BNC60.

In some embodiments, the NIH45-46G54W is further substituted in the light chain at the serine at position 28. The substitution of the serine at position 28 can be tryosine (Y), and the substitution is referred to herein, as S28Y or S28Y LC. The resulting double substituted (i.e, double mutant) antibody can be referred to as $NIH45\text{-}46^{G54W(HC)\ S28Y(LC)}$ or as 45-46 m2.

Abbreviations for amino acids are used throughout this disclosure and follow the standard nomenclature known in the art. For example, as would be understood by those of ordinary skill in the art, Alanine is Ala or A; Arginine is Arg or R; Asparagine is Asn or N; Aspartic Acid is Asp or D; Cysteine is Cys or C; Glutamic acid is Glu or F; Glutamine is Gln or Q; Glycine is Gly or G; Histidine is His or H; Isoleucine is Ile or I; Leucine is Leu or L; Lysine is Lys or K; Methionine is Met or M; Phenylalanine is Phe or F; Proline is Pro or P; Serine is Ser or S; Threonine is Thr or T; Tryptophan is Trp or W; Tyrosine is Tyr or Y; and Valine is Val or V.

Hydrophobic amino acids are well known in the art. Hydrophobic amino acids include alanine, isoleucine, leucine, methionine, phenylalanine, tryptophan, tyrosine, and valine. In some embodiments of the present invention, an anti-CD4bs PVL antibody has a hydrophobic amino acid substituted at a position equivalent to Phe43 of the CD4 receptor protein, wherein the hydrophobic amino acid is alanine, isoleucine, leucine, methionine, phenylalanine, tryptophan, tyrosine, or valine. In other embodiments, an anti-CD4bs PVL antibody has a hydrophobic amino acid substituted at the position equivalent to Phe43 of CD4 receptor protein, wherein the hydrophobic amino acid is tryptophan, phenylalanine, or tyrosine.

In addition to the hydrophobic acids, other amino acids that may be substituted at the Phe43-equivalent position of CD4 in the heavy chain of a PVL antibody, include glycine, histidine, arginine, glutamine, asparagine, glutamic acid, aspartic acid, lysine, and serine.

Throughout this disclosure and in embodiments of the present invention, the term "antibody" (Ab) as used herein includes monoclonal antibodies, polyclonal antibodies, multispecific antibodies (for example, bispecific antibodies and polyreactive antibodies), and antibody fragments. Thus, the term "antibody" and "isolated antibody" are used interchangeably herein to refer to an isolated antibody according to embodiments of the present invention. An antibody in any context within this specification is meant to include, but is not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). It is understood in the art that an antibody is a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a tight chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from the NH2 terminus to the COOH terminus as follows: FWR1, CDR1, FWR2, CDR2, FWR3, CDR3, FWR4. The variable regions of the heavy and light chains contain a binding domain that interacts with an antigen while, depending on the isotype, the constant region(s) may mediate the binding of the immunoglobulin to host tissues or factors. CDR1, CDR2, and CDR3 of the light chain are referred to as CDRL1, CDRL2 and CDRL3, respectively. CDR1, CDR2, CDR3 of the heavy chain are referred to as CDRH1, CDRH2, and CDRH3, respectively.

Also included in the definition of "antibody" as used herein are chimeric antibodies, humanized antibodies, and recombinant antibodies, human antibodies generated from a transgenic non-human animal, as well as antibodies selected from libraries using enrichment technologies available to the artisan. The term "variable" refers to the fact that certain segments of the variable (V) domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta sheet configuration, connected by three hypervariable regions, which form loops connecting, and in some cases forming part of, the beta sheet structure. The hypervariable regions in each chain are held together in close proximity by the FRs and, with the hypervariable regions from the other chain, contribute to the formation of the antigen-binding site of antibodies. The term "hypervariable region" as used herein refers to the amino acid residues of an antibody that are responsible for antigen binding. The hypervariable region generally comprises amino acid residues from a "complementarity determining region" ("CDR").

An antibody of the present invention may be a "humanized antibody". A humanized antibody is considered to be a human antibody that has one or more amino acid residues introduced into it from a source that is non-human. These non-human amino acid residues often are referred to as "import" residues, which typically are taken from an "import" variable region. Humanization may be performed following known methods by substituting import hypervariable region sequences for the corresponding sequences of a human antibody. (See, for example, Jones et al., Nature, 321:522-525 20 (1986); Reichmann et al., Nature, 332:323-327 (1988); Verhoeyen et al., Science, 239:1534-1536 (1988)) the entire contents of each are incorporate herein by reference). Accordingly, such "humanized" antibodies are chimeric antibodies in which substantially less than an intact human variable region has been substituted by the corresponding sequence from a non-human species.

An antibody of the present invention includes an "antibody fragment" which includes a portion of an intact antibody, such as the antigen binding or variable region of the intact antibody. Examples of antibody fragments include, but are not limited to, Fab, Fab', F(ab')2, and Fv fragments; diabodies; linear antibodies; single-chain antibody molecules; and multispecific antibodies formed from antibody fragments. (See, for example, U.S. Pat. No. 5,641,870, the entire content of which is incorporated herein by reference).

Throughout this disclosure and in embodiments of the present invention, a "potent VRC01-like" ("PVL") antibody of the present invention is an anti-CD4 binding site antibody that has the following conserved heavy chain (HC) and light chain (LC) residues: $Arg71_{HC}$, $Trp50_{HC}$, $Asn58_{HC}$, $Trp100B_{HC}$, $Glu96_{LC}$, $Trp67_{LC}/Phe67_{LC}$, as well as exactly 5 amino acids in CDRL3 domain (using Kabat numbering). (The Kabat numbering system is described in Abhinandan, K. R. and Martin, A. C. R. (2008), "Analysis and improvements to Kabat and structurally correct numbering of antibody variable domains," *Molecular Immunology*, 45: 3832-3839, the entire contents of which are herein incorporated by reference). A PVL antibody of the present invention is any antibody as defined herein, that has the listed FAT features irrespective of the synthesis or derivation of the antibody, irrespective of the other unrestricted domains of the antibody, and irrespective of whether or not other domains of the antibody are present, so long as the antibody has the signature residues and features.

Throughout the disclosure and in embodiments of the present invention, the terms "Phe43-equivalent position" and "Phe43.sub.CD4 equivalent position" are used interchangeably and refer to an amino acid position within the heavy chain of a PVL antibody that replicates or mimics the binding pocket and interface contributed by Phe43 of the host CD4 receptor when the CD4 receptor protein is complexed with the HIV viral spike protein gp120. As known in the art, assigned amino acid positions of an antibody do not necessarily correspond to the amino acid residue as numbered from the amino-terminus. Following the Kabat antibody residue/position numbering system, the amino acid residue number may be the same as the amino acid position, but is not necessarily so. (See, Abhinandan, K. R. and Martin, A. C. R. (2008) Molecular immunology, 45: 3832-3839). The structure of the antibody peptide determines the position number. The information for determining position number using the Kabat system for each amino acid in a given sequence can be determined using the information found in Abhinandan and Martin, 2008. Using this position numbering system, the Phe43-equivalent position in a PVL antibody heavy chain sequence can be determined, and substituted with a hydrophobic amino acid to create a similar binding pocket as conferred by Phe43 in CD4. Methods for this mutagenesis are well known in the art (e.g. Example 2).

Subsequent heavy chain sequences can be analyzed using the Kabat numbering system to determine the equivalent position to this position 54. Alternatively, the $Phe43_{CD4}$-equivalent position can also be determined by structural analysis such as x-ray crystallography. Any means of determining the $Phe43_{CD4}$-equivalent position may be used so long as the Kabat system is followed as applicable.

For example, the Phe43-equivalent position in NIH45-46 is position 54 as determined by x-ray crystallography and shown herein. The native NIH45-46 heavy chain sequence (SEQ NO: 6) contains a glycine at position 54 (Gly54). The native 3BNC60 heavy chain sequence (SEQ ID NO: 8) contains a threonine at position 54 (Thr54). As such, these PVL antibodies substituted with a hydrophobic amino acid, glycine, histidine, arginine, glutamine, or asparagine at these Phe-43 equivalent positions mimic the desired contact interface between the CD4 receptor protein and the CD4 binding site of gp120 (see, e.g., Example 2).

In some embodiments of the present invention, position 54 (Kabat numbering) of the heavy chain of a PVL antibody has a substituted hydrophobic amino acid. Position 54 is determined by analyzing a heavy chain amino acid sequence of a PVL antibody using the Kabat numbering system.

In some embodiments of the present invention, a hydrophobic amino acid is substituted for the "native" amino acid present at the $Phe43_{CD4}$-equivalent position on the heavy chain of a PVL antibody, where a PVL antibody is an antibody as defined herein having the PVL signature features as described herein, and "native" refers to the amino acid that is present in the PVL antibody prior to substitution. The native amino acid in the heavy chain may also be hydrophobic, and may be substituted with another hydrophobic amino acid, or with glycine, histidine, arginine, glutamine, asparagine, lysine, glutamic acid, and aspartic acid.

In some embodiments of the present invention, non-limiting examples of PVL antibodies include VRC01, VRC02, NIH45-46, 3BNC60, 3BNC117, 3BNC62, 3BNC95, 3BNC176, 12A21, VRC-PG04, VRC-CH30, VRC-CH31, VRC-CH32, VRC-CH33, VRC-CH34, VRC03 heavy chain (HC) with VRC01 light chain (LC), gVRC-H5 (d74)/VRC-PG04LC, and gVRC-H12(d74)/VRC-PG04LC, VRC03, VRC01 heavy chain (HC) with VRC03 light chain (LC), 3BNC55, 3BNC91, 3BNC104, 3BNC89, 12A21, and VRC-PG04b as listed below in Table 1.

TABLE 1

Examples of PVL Antibodies

| Antibody Name | Light Chain SEQ ID NO: | Heavy Chain SEQ ID NO: |
| --- | --- | --- |
| VRC01 | 1 | 2 |
| VRC02 | 3 | 4 |
| NIH-45-46 | 5 | 6 |
| 3BNC60 | 7 | 8 |
| 3BNC117 | 9 | 10 |
| 3BNC62 | 11 | 12 |
| 3BNC95 | 13 | 14 |
| 3BNC176 | 15 | 16 |
| 12A12 | 17 | 18 |
| VRC-PG04 | 19 | 20 |
| VRC-CH30 | 21 | 22 |
| VRC-CH31 | 23 | 24 |
| VRC-CH32 | 25 | 26 |
| VRC-CH33 | 27 | 28 |
| VRC-CH34 | 29 | 30 |
| VRC03 | 31 | 32 |
| 3BNC55 | 33 | 34 |
| 3BNC91 | 35 | 36 |
| 3BNC104 | 37 | 38 |
| 3BNC89 | 39 | 40 |
| 12A21 | 41 | 42 |
| VRC-PG04b | 43 | 44 |
| VRC03HC-VRC01LC | 1 | 32 |
| VRC01HC/VRC03LC | 31 | 2 |
| gVRC-H5(d74)/ VRC-PG04LC | 19 | 45 |
| gVRC0H12(D74)/ VRC-PG04LC | 19 | 46 |

In some embodiments of the present invention, a PVL antibody has a heavy chain selected from one of the heavy chains listed above in Table 1 (SEQ ID NOs 2, 4, 6, 8, 10, 12, 14, 16, 18, 20, 22, 24, 26, 28, 30, 32, 34, 36, 38, 40, 42, 44, 45, and 46). Any PVL heavy chain may be matched with a PVL light chain so long as the signature PVL residue features are maintained. In some embodiments, any one of the PVL heavy chains of Table 1 is expressed with any one of the PVL light chains of SEQ ID NOs 1, 3, 5, 7, 9, 11, 13, 15, 17, 19, 21, 23, 25, 27, 29, 31, 33, 35, 37, 39, 41, and 43. In other embodiments, any PVL antibody heavy chain can be combined with any PVL antibody light chain.

In embodiments of the present invention, the terms "nucleic acid" and "polynucleotide" are used interchangeably herein to refer to single-stranded or double-stranded RNA, DNA, or mixed polymers. Polynucleotides can include genomic sequences, extra-genomic and plasmid sequences, and smaller engineered gene segments that express, or can be adapted to express polypeptides.

An "isolated nucleic acid" is a nucleic acid that is substantially separated from other genome DNA sequences as well as proteins or complexes such as ribosomes and polymerases, which naturally accompany a native sequence.

In some embodiments of the present invention, nucleic acid molecules encode part or all of the light and heavy chains of the described inventive antibodies, and fragments thereof. Due to redundancy of the genetic code, variants of these sequences will exist that encode the same amino acid sequences.

The present invention also includes isolated nucleic acid molecules encoding the polypeptides of the heavy and the light chain of the PVL antibodies listed in Table 1. In some embodiments, an isolated nucleic acid molecule encodes for any of the PVL heavy chain and light chain polypeptides including those of SEQ ID NOs 2, 4, 6, 8, 10, 12, 14, 16, 18, 20, 22, 24, 26, 28, 30, 32, 34, 36, 38, 40, 42, 44, 45, and 46, and SEQ NOs 1, 3, 5, 7, 9, 11, 13, 15, 17, 19, 21, 23, 25, 27, 29, 31, 33, 35, 37, 39, 41, and 43, respectively, in which the Phe43$_{CD4}$-equivalent amino acid (i.e., the target amino acid) of the heavy chain is substituted with a hydrophobic amino acid.

Embodiments of the present invention also include vectors and host cells including a nucleic acid encoding a PVL antibody of the present invention, as well as recombinant techniques for the production of polypeptide of the invention. Vectors of the invention include those capable of replication in any type of cell or organism, including, for example, plasmids, phage, cosmids, and mini chromosomes. In some embodiments, vectors comprising a polynucleotide 5 of the described invention are vectors suitable for propagation or replication of the polynucleotide, or vectors suitable for expressing a polypeptide of the described invention. Such vectors are known in the art and commercially available.

In embodiments of the present invention, "vector" includes shuttle and expression vectors. Typically, the plasmid construct will include an origin of replication (for example, the ColE1 origin of replication) and a selectable marker (for example, ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells.

In some embodiments of the present invention, in order to express a polypeptide of the invention, the nucleotide sequences encoding the polypeptide, or functional equivalents, may be inserted into an appropriate expression vector, i.e., a vector that contains the necessary elements for the transcription and translation of the inserted coding sequence. Methods well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (2001) Molecular Cloning, A Laboratory Manual, Cold Spring Harbor Press, Plainview, N.Y., the entire contents of which are incorporated herein by reference.

As used herein, the term "cell" can be any cell, including, but not limited to, eukaryotic cells, such as, but not limited to, mammalian cells or human cells.

In some embodiments of the present invention, the antibodies disclosed herein are produced recombinantly using vectors and methods available in the art. (see, e.g. Sambrook et al., 2001, supra). Human antibodies also can be generated by in vitro activated B cells (see, for example, U.S. Pat. Nos. 5,567,610 and 5,229,275). Reagents, cloning vectors, and kits for genetic manipulation are available from commercial vendors such as BioRad, Stratagene, Invitrogen, ClonTech and Sigma-Aldrich Co.

In some embodiments of the present invention, human antibodies are produced in transgenic animals (for example, mice) that are capable of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germline mutant mice results in the production of human antibodies upon antigen challenge. See, for example, Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669; U.S. Pat. No. 5,545,807; and WO 97/17852, the entire contents of all of which are incorporated herein by reference. Such animals can be genetically engineered to produce human antibodies comprising a polypeptide of a PVL antibody of the present invention.

In some embodiments of the present invention, a method includes the preparation and administration of an HIV antibody composition (e.g., a PVL antibody having a hydrophobic amino acid substituted at the Phe43$_{CD4}$-equivalent position of the PVL heavy chain) that is suitable for administration to a human or non-human primate patient having an HIV infection, or at risk of infection, in an amount and according to a schedule sufficient to induce a protective immune response against HIV, or reduction of the HIV virus, in a human.

In some embodiments of the present invention, a vaccine includes at least one antibody as disclosed herein and a pharmaceutically acceptable carrier. In some embodiments of the present invention, the vaccine is a vaccine including at least one PVL antibody as described herein and a pharmaceutically acceptable carrier. The vaccine can include a plurality of the antibodies having the characteristics described herein in any combination and can further include HIV neutralizing antibodies such as a PVL antibody having the $Phe43_{CD4}$-equivalent residue on the heavy chain substituted with a hydrophobic amino acid.

In some embodiments of the present invention, carriers as used herein include pharmaceutically acceptable carriers, excipients or stabilizers that are nontoxic to the cell or mammal being exposed thereto at the dosages and concentrations employed. Often the physiologically acceptable carrier is an aqueous pH buffered solution. Examples of physiologically acceptable carriers include, but are not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to: polyvinylpyrrolidone; amino acids such as, but not limited to: glycine, glutamine, asparagine, arginine or lysine; monosaccharides, disaccharides, and other carbohydrates including, but not limited to: glucose, mannose, or dextrins; chelating agents such as, but not limited to: EDTA (ethylenediaminetetraacetic acid); sugar alcohols such as, but not limited to: mannitol or sorbitol; salt-forming counterions such as, but not limited to: sodium; and/or nonionic surfactants such as, but not limited to TWEEN® (polysorbate); polyethylene glycol (PEG), and PLURONICS® (poloxamers).

In some embodiments of the present invention, the compositions may include a single antibody or a combination of antibodies, which can be the same or different, in order to prophylactically or therapeutically treat the progression of various subtypes of HIV infection after vaccination. Such combinations can be selected according to the desired immunity. When an antibody is administered to an animal or a human, it can be combined with one or more pharmaceutically acceptable carriers, excipients or adjuvants as are known to one of ordinary skilled in the art. The composition can further include broadly neutralizing antibodies known in the art, including, for example, a PVL antibody having the Phe43$_{CD4}$-equivalent residue substituted with a hydrophobic amino acid or glycine, histidine, arginine, glutamine, asparagine, glutamic acid, and aspartic acid, and the serine at position 28 of the light chain substituted with tyrosine (S28Y LC).

In some embodiments of the present invention, an antibody-based pharmaceutical composition includes a therapeutically effective amount of an isolated HIV antibody which provides a prophylactic or therapeutic treatment choice to reduce infection of the HIV virus. The antibody-based pharmaceutical composition of the present invention may be formulated by any number of strategies known in the art (e.g., see McGoff and Scher, 2000, Solution Formulation of Proteins/Peptides: In McNally, E. J., ed. Protein Formulation and Delivery. New York, N.Y.: Marcel Dekker; pp. 139-158; Akers and Defilippis, 2000, Peptides and Proteins as Parenteral Solutions. In: Pharmaceutical Formulation Development of Peptides and Proteins. Philadelphia, Pa.: Taylor and Francis; pp. 145-177; Akers, et al., 2002, Pharm. Biotechnol. 14:47-127, the entire contents of all of which are incorporated herein by reference).

In some embodiments of the present invention, a method for treating a mammal infected with a virus infection, such as, for example, HIV, comprising administering to said mammal a pharmaceutical composition comprising an antibody composition as disclosed herein. According to some embodiments, the method for treating a mammal infected with HIV includes administering to said mammal a pharmaceutical composition that includes an antibody as disclosed herein, or a fragment thereof. The compositions of embodiments of the present invention may include more than one antibody having the characteristics disclosed herein. For example, a plurality or pool of PVL antibodies, each antibody having the Phe43$_{CD4}$-equivalent residue substituted with a hydrophobic amino acid.

In some embodiments of the present invention, in vivo treatment of human and non-human patients includes administering or providing a pharmaceutical formulation including an antibody according to embodiments of the present invention. When used for in vivo therapy, the antibodies of the invention are administered to the patient in therapeutically effective amounts (i.e., amounts that eliminate or reduce the patient's viral burden). The antibodies are administered to a human patient, in accord with known methods, such as intravenous administration, for example, as a bolus or by continuous infusion over a period of time, by intramuscular, intraperitoneal, intracerobrospinal, subcutaneous, intra-articular, intrasynovial, intrathecal, oral topical, or inhalation routes. The antibodies can be administered parenterally, when possible, at the target cell site, or intravenously. In some embodiments, a PVL antibody composition as described herein is administered by intravenous or subcutaneous administration.

In some embodiments of the present invention, a therapeutically effective amount of an antibody is administered to a patient. In some embodiments, the amount of antibody administered is in the range of about 0.1 mg/kg to about 50 mg/kg of patient body weight. Depending on the type and severity of the infection, about 0.1 mg/kg to about 50 mg/kg body weight (for example, about 0.1-15 mg/kg/dose) of antibody is an 5 initial candidate dosage for administration to the patient, whether, for example, by one or more separate administrations, or by continuous infusion. The progress of this therapy is readily monitored by conventional methods and assays and based on criteria known to the physician or other persons of skill in the art. The above parameters for assessing successful treatment and improvement in the disease are readily measurable by routine procedures familiar to a physician.

In some embodiments of the present invention, passive immunization using a PVL antibody as disclosed herein, is used as an effective and safe strategy for the prevention and treatment of HIV disease. (See, for example, Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference).

The following Examples are presented for illustrative purposes only, and do not limit the scope or content of the present application.

EXAMPLES

Reference is made to Riskin et al., 2011, *Science*. 334: 12989-1293; and West et al., 2012, *PNAS*, (doi: 10.1073/pnas.1208984109), the entire contents of both of which are incorporated herein by reference.

Example 1

Structural Comparisons of NIH45-46 and VRC01

Figure 3A:
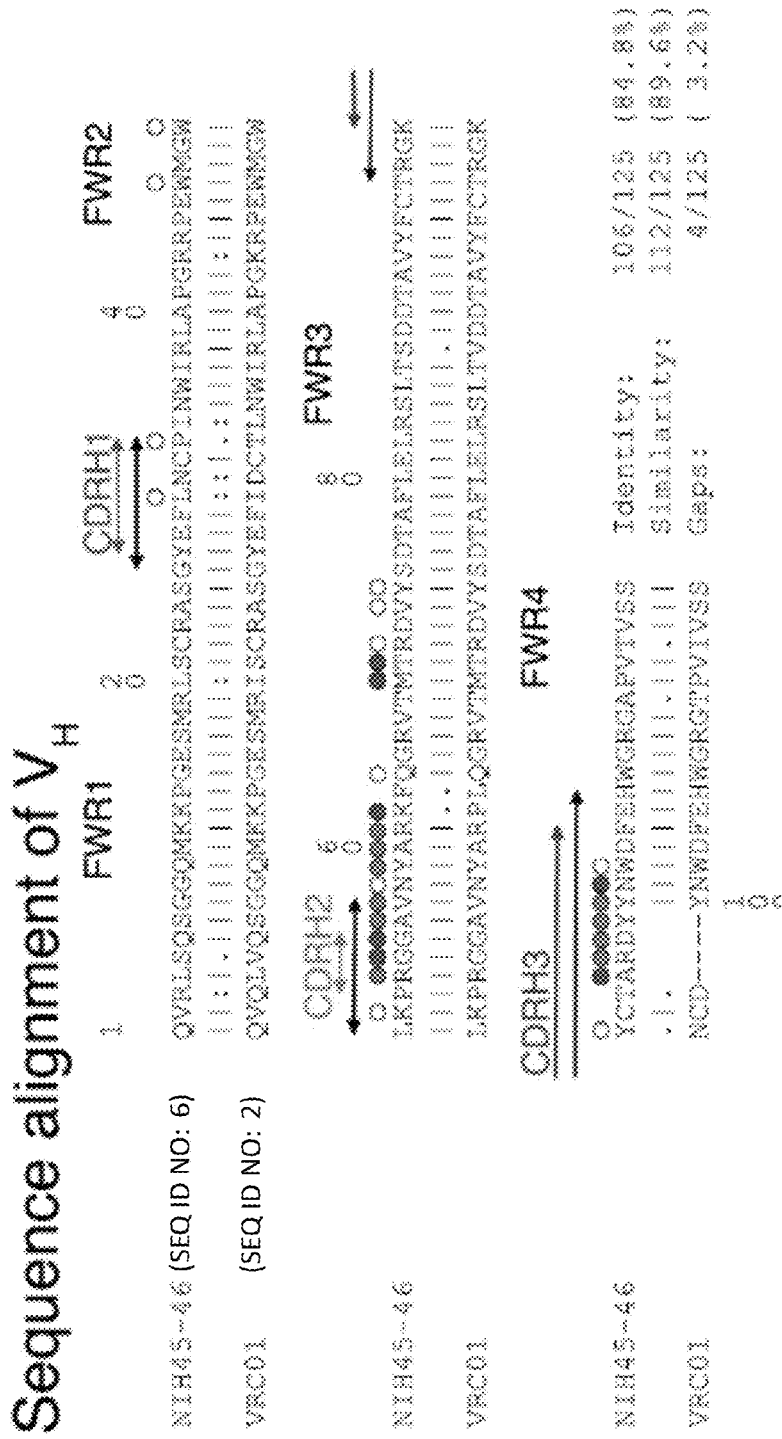
Figure 3B:
Figure 4A:
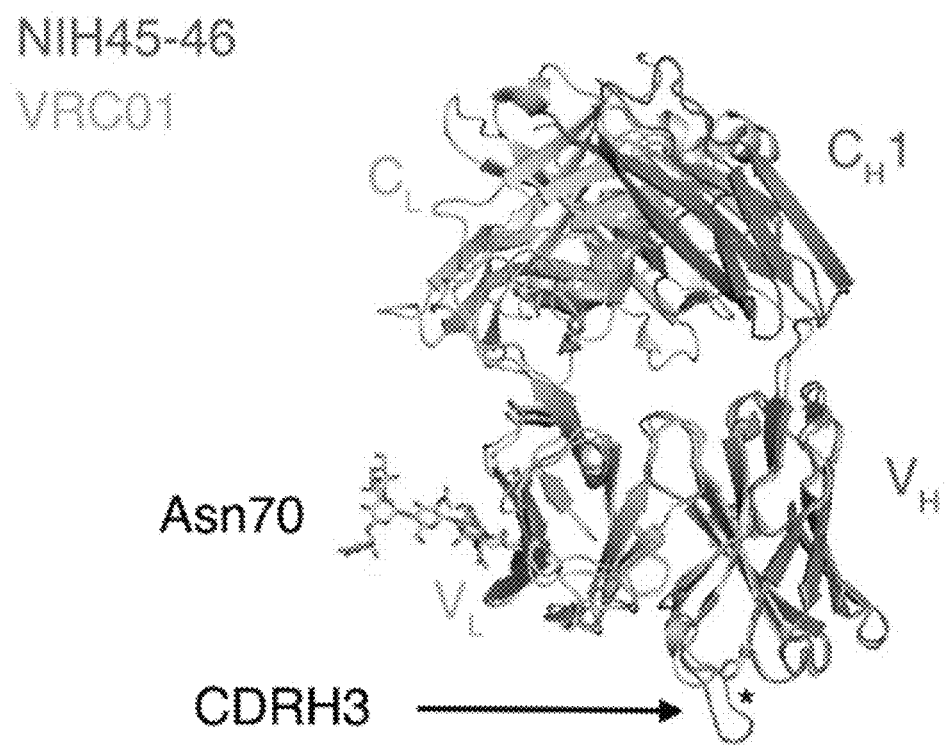
Figure 4B:
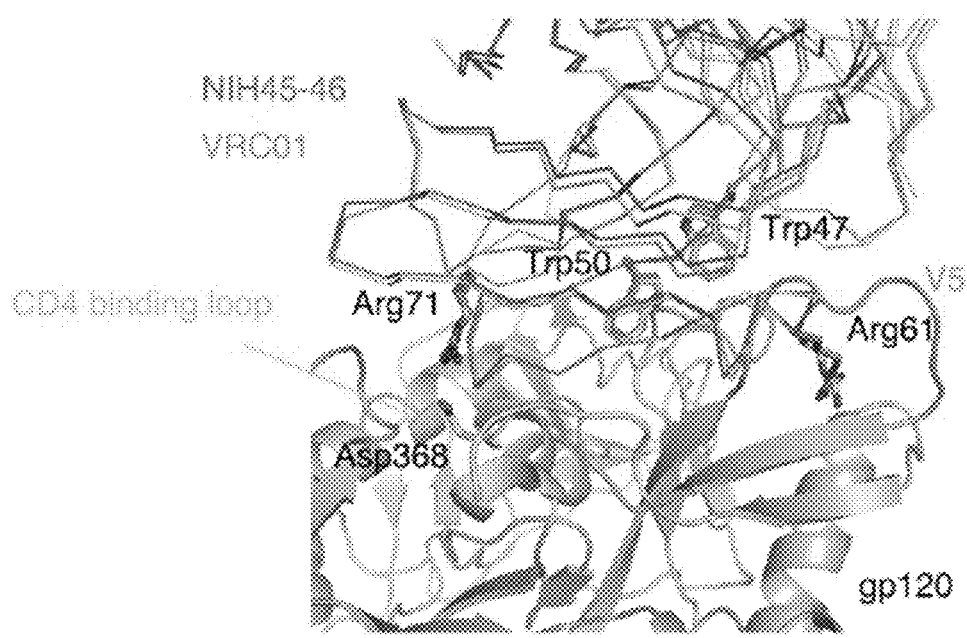

To determine structural correlates of high potency and breadth in HAADs, structures of NIH45-46 alone and bound to the Glade A/E 93TH057 gp120 core were solved (FIGS. 1A, 1B and 2). NIH45-46 is a more potent clonal variant of VRC01 that was isolated from the same donor using a YU2 trimer (Sheid et al., 2011, supra), instead of a resurfaced gp120 core (RSC3) as a bait. Comparisons of NIH45-46 Fab in its free versus gp120-bound states demonstrate that gp120 binding does not require major conformational changes (FIG. 1A). However, gp120 binding induced minor conformational in CDRL1, CDRH3, and in heavy chain framework region 3 (FWR3). As predicted by high sequence identity (85% in $V_H$; 96% in $V_L$) (FIGS. 3A and 3B), NIH45-46 resembles VRC01 (FIGS. 4A and 4B). However, relative to VRC01, NIH45-46 includes a four-residue insertion within CDRH3 (FIG. 5) that was acquired by somatic hypermutation. (See, Sheid et al., 2011, Science, 333:1633-1637, the entire contents of which are incorporated herein by reference).

Figure 5:
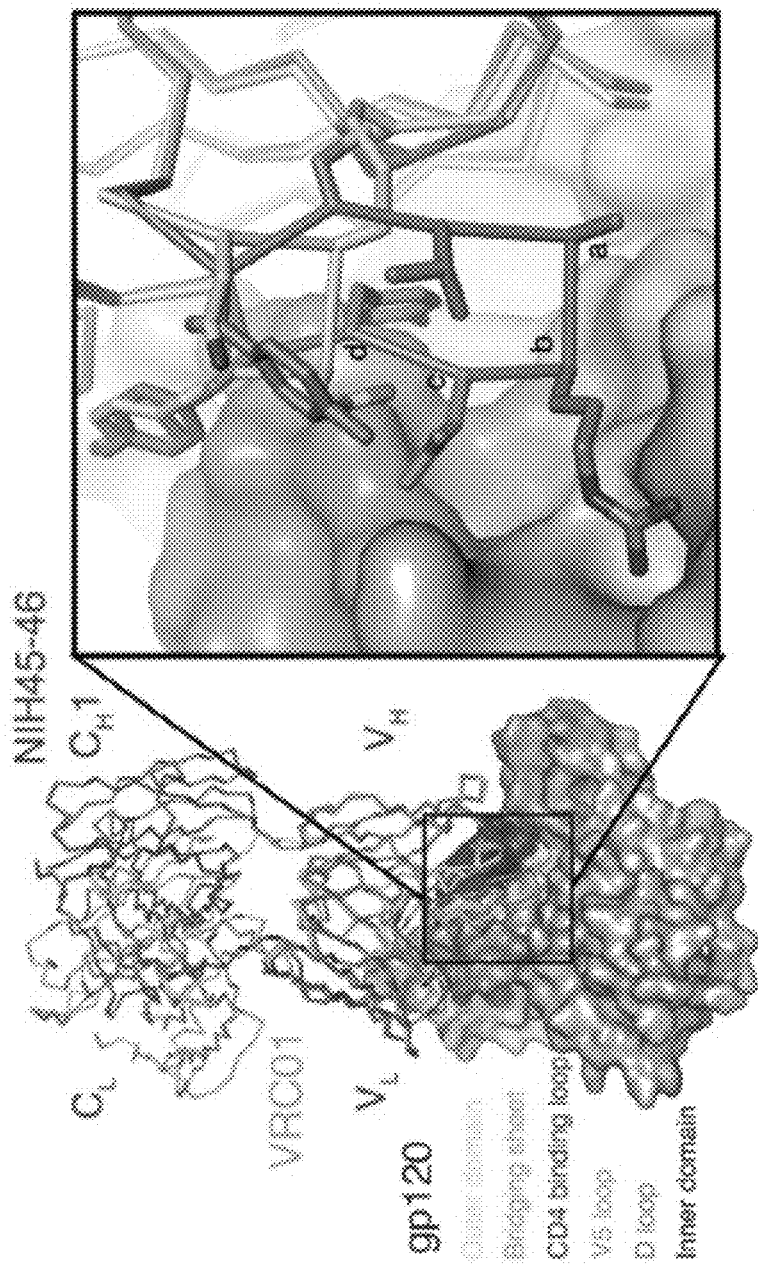
Figure 6A:
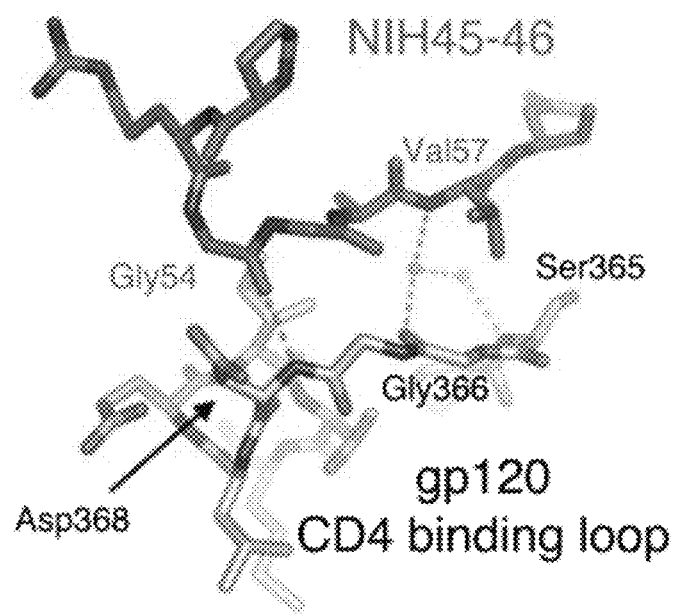
Figure 6B:
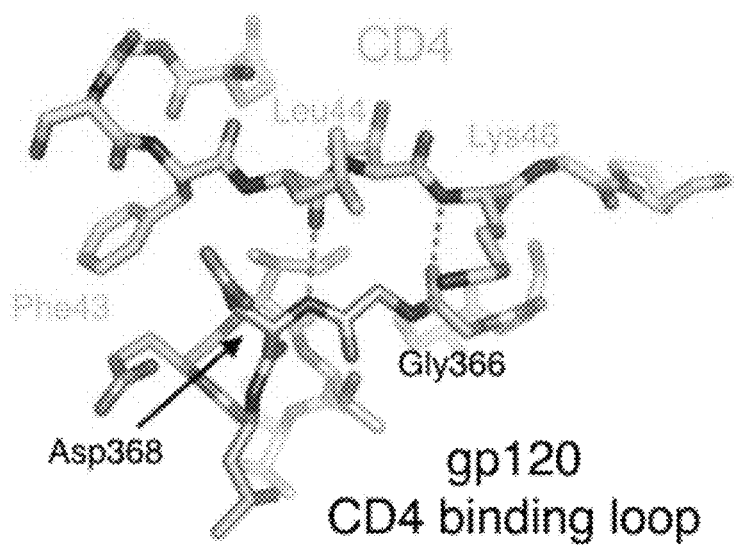
Figure 6C:
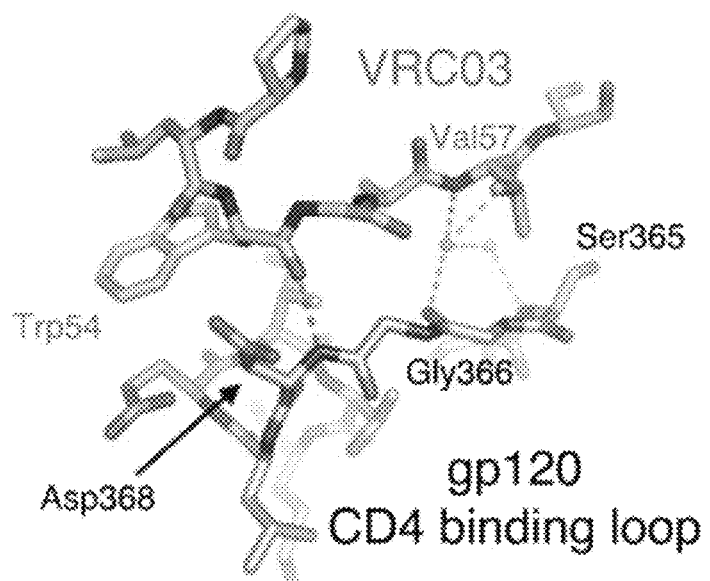
Figure 9A:
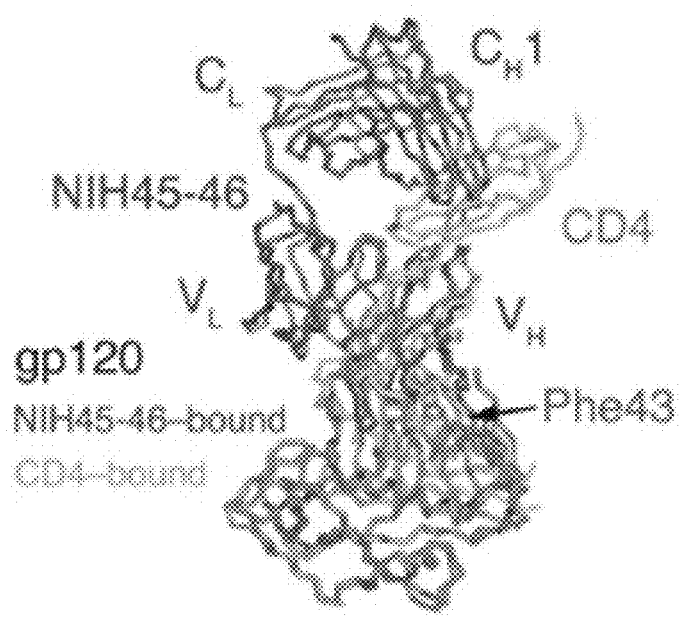
FIG. 9D is a structural depiction of a NIH45-46-gp120 (93TH057) complex with the contact interface labeled and colored as in FIG. 1B, and the corresponding Phe43$_{CD4}$ cavity as shown in FIG. 9B is indicated by the asterisk, according to embodiments of the present invention.
FIG. 9E is a structural depiction of a VRC01-gp120 (93TH057) complex with the contact interface labeled and colored as in FIG. 1B, according to embodiments of the present invention.
Figure 9B:
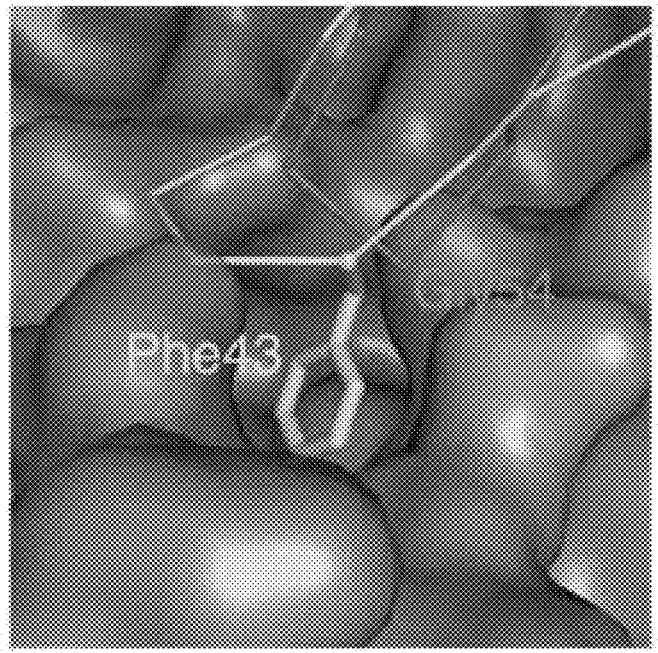

The crystal structure of the NIH45-46-93TH057 gp120 complex verified that NIH45-46 targets the CD4bs on gp120 (FIGS. 1B and 5). The primary binding surface is the outer domain, including the CD4 binding loop (FIG. 6A), loop D and loop V5, but CDRH3$_{NIH45-46}$ reaches toward the gp120 inner domain (FIG. 1B, 6A-6C). Important interactions in the VRC01-93TH057 structure are conserved in NIH45-46 (FIG. 4B); e.g., residues C-terminal to CDRH12 of VRC01 and NIH45-46 mimic the interaction of main-chain atoms in the C" β-strand of CD4 domain, which hydrogen bond with the CD4-binding loop of gp120 (FIGS. 6A, 6B and 6C). In both NIH45-46 and VRC01, hydrogen bonds between CDRH2 and gp120 are water-mediated (except for the Gly54$_{NIH45-46}$/Gly54$_{VRC01}$ carbonyl oxygen-Asp368$_{gp120}$ backbone nitrogen H-bond (FIGS. 6A, 6B and 6C)), and Arg71$_{VRC01}$/Arg71$_{NIH45-46}$ preserves the Arg59$_{CD4}$ interaction with Asp368$_{gp120}$. However, the Phe43$_{CD4}$ interaction with a hydrophobic pocket between α-helix 3$_{gp120}$ (CD4 binding loop) and β-strand 21$_{gp120}$ (bridging sheet) (FIGS. 9A and 9B) is not mimicked by either antibody. Differences between VRC01 and NIH45-46 include the conformation of heavy chain residue Tyr74, a FWR3 residue that was substituted during somatic hypermutation (Sheid et al., 2011, supra), and a tyrosine to serine substitution in CDRL1 (FIGS. 10A, 10B, 11A, and 11B).

A notable difference between VPC01 and NIH45-46 is the four-residue insertion (residues 99a-99d) in CDRH3. Three inserted residues contribute to binding to gp120-inset), consistent with deletion of the insertion resulting in about 10-fold reduced neutralization potencies (Tables 2 and 3, below).

TABLE 2

In vitro neutralization IC$_{50}$ values (µg/mL)

| Virus | Clade | NIH45-46 WT | NIH45-46 Y99dA | NIH45-46 Δ99a-99d |
|---|---|---|---|---|
| AC10.0.29 | B | 0.9 | 4.4 | 13 |
| TRO.11 | B | 1.9 | >50 | >50 |
| SC422661.8 | B | 0.05 | 0.08 | 1.4 |
| QH0692.42 | B | 0.7 | 2.1 | 3.7 |
| ZM214M.PL15.11 | C | 0.3 | 1.1 | 2.2 |
| CAP45.2.00.G3 | C | >50 | >50 | >50 |
| T257-31 | CRF02 (A/G) | 0.5 | 2.4 | 7.0 |

TABLE 3

| | CDRH3 sequence |
|---|---|
| NIH45-46 WT | FCTRGKYCTARDYYNWDFEHWGRGAP |
| NIH45-46 Y99dA | FCTRGKYCTARDAYNWDFEHWGRGAP |
| NIH45-46 Δ99a-99d | FCTRGKYCT----YNWDFEHWGRGAP |

First, the Tyr99d$_{NIH45-46}$ sidechain hydrogen bonds with the loop D Ala281$_{gp120}$ carbonyl oxygen 7), a main-chain atom, thus preventing escape through mutation. Indeed, NIH45-46-sensitive strains accommodate different sidechains at position 281$_{gp120}$ (Table 4, below).

TABLE 4

Comparison of in vitro neutralization for viral strains with differences at 281$_{gp120}$

| Strain | gp120 sequence surrounding residue 281 | Residue 281$_{gp120}$ | IC$_{50}$* µg/mL |
|---|---|---|---|
| Du156.12 | QLLLNGSLAEEEIIIKSENLTDNIKTIIVQLNQSIGINCTRPNNNTRKSV | I | 0.01 |
| ZM197M.PB7 | QLLLNGSLAEEEIIIRSENLTDNTKTIIVHLNESVEIECVRPNNNTRKSV | T | 0.14 |
| ZM214M.PL15 | QLLLNGSLAEKEIMIRSENLTNNAKTIIVQLTEAVNITCMRPGNNTRRSV | A | 0.05 |
| ZM249M.PL1 | QLLLNGSLAEKEIIIRSENITDNVKIIIVHLNESVEINCTRPNNNTRKSI | V | 0.02 |
| ZM53M.PB12 | QLLLNGSTAEEDIIIRSENLTNNAKTIIVHLNESIEIECTRPGNNTRKSI | A | 0.65 |
| ZM109F.PB4 | QLLLNGSLAEEEIVIRSENLTDNAKTIIVHLNKSVEIECIRPGNNTRKSI | A | 0.22 |
| ZM135M.PL10a | QLLLNGSLSEEGIIIRSKNLTDNTKTIIVHLNESVAIVCTRPNNNTRKSI | T | 0.36 |

Figure 7:
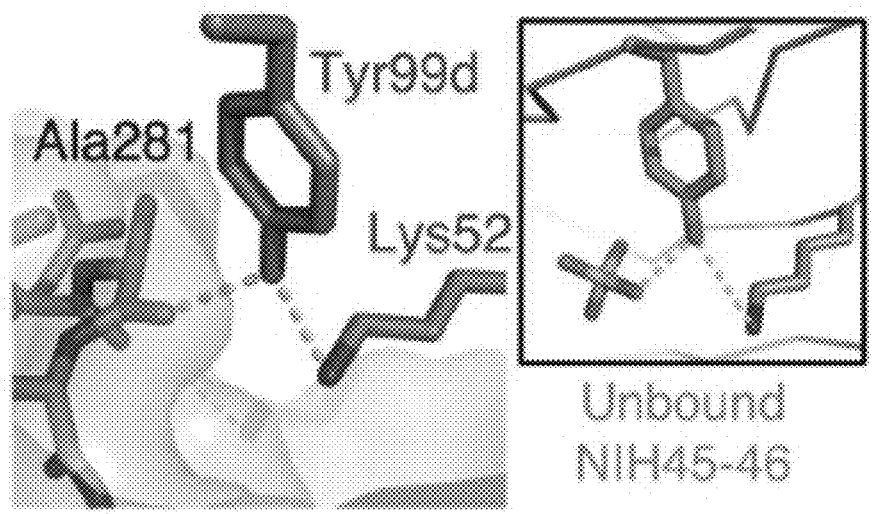
Figure 8:
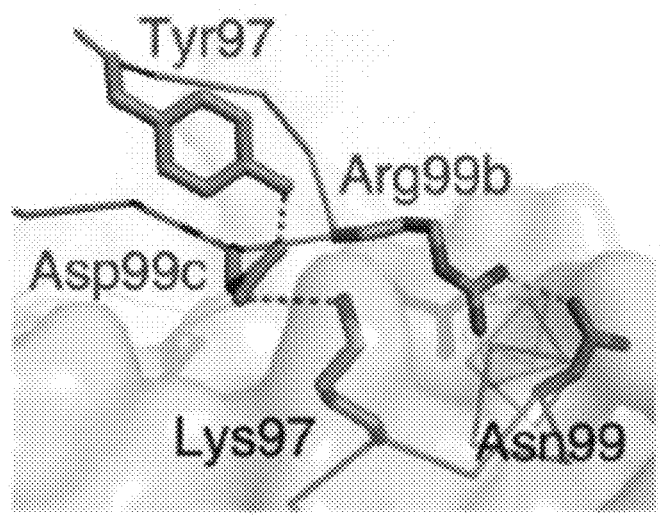
Figure 9C:
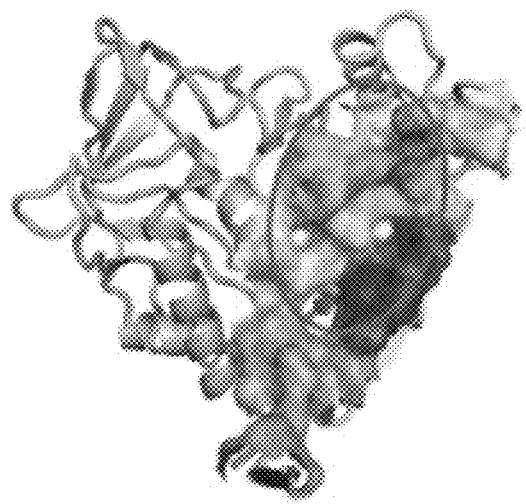

The importance of Tyr99d$_{NIH45-46}$ for potency is demonstrated by alanine substitution (NIH45-46 Y99dA), which reduces the neutralization potency of NIH45-46 to values intermediate between wild-type NIH45-46 and the deletion mutant (Table 2), Second, Asp99c$_{NIH45-46}$ interacts electrostatically with Lys97$_{gp120}$ at the base of α-helix 1$_{gp120}$, and third, Arg99b$_{NIH45-46}$ hydrogen bonds with Asn99$_{gp120}$ (FIG. 8). The conformation of the insertion is stabilized by two intramolecular hydrogen bonds. In one, the Tyr99d$_{NIH45-46}$ sidechain hydrogen bonds with the amino group of Lys52$_{NIH45-46}$ within CDRH2 (FIG. 7), also seen in the unbound structure of NIH45-46 (FIG. 7-inset), thus the Tyr99d$_{NIH45-46}$ hydroxyl is poised for interacting with Ala281$_{gp120}$. A second hydrogen bond between Tyr97$_{NIH45-46}$ and Asp99c$_{NIH45-46}$ in the gp120-bound Fab positions the negatively-charged aspartic acid for interaction with Lys97$_{gp120}$ (FIG. 8). The region of gp120 with which CDRH3$_{NIH45-46}$ interacts was not included in the previously-defined vulnerable site of initial CD4 attachment on the gp120 outer domain (FIG. 9C). Thus, gp120 residues that contact CDRH3$_{NIH45-46}$ residues required for potent neutralization (Table 2), e.g., Lys97$_{gp120}$, were mutated in RSC3 (FIG. 12), the resurfaced gp120 used for isolating bNAbs and as a candidate HIV immunogen.

Figure 9D:
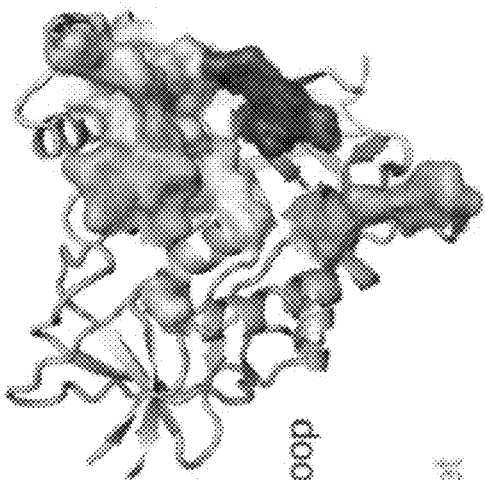
Figure 9E:
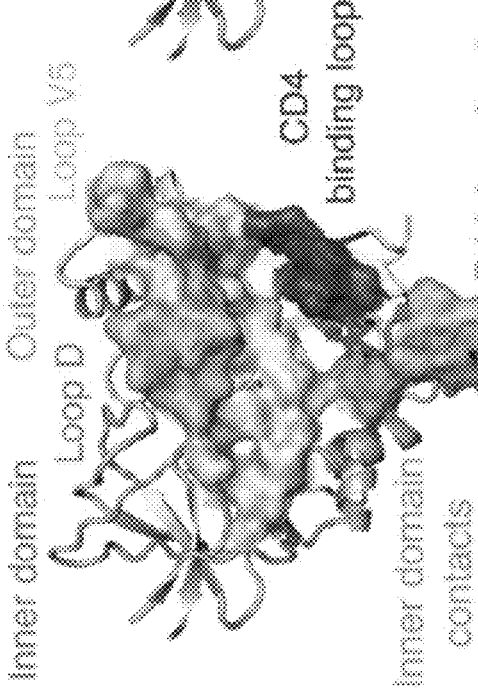
Figure 10A:
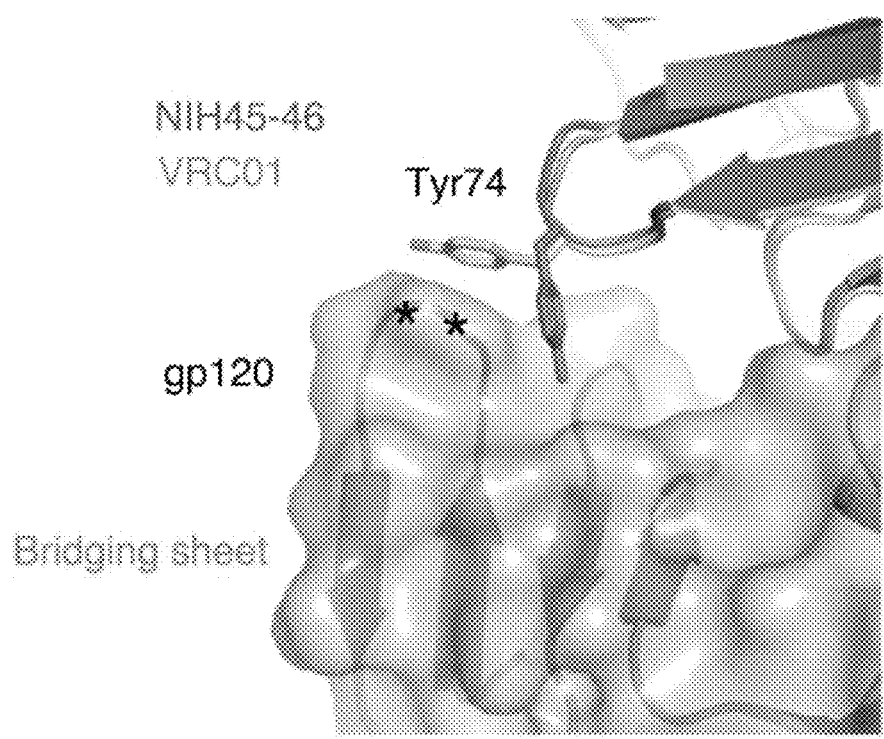
FIG. 10A is a structural depiction of a NIH45-46-gp120 complex superimposed with a VRC01-gp120 complex, in which the Tyr74 shows different interactions with gp120, and the gp120 bridging sheet is depicted with the broad arrows in gp120 and the asterisks indicate a recombinant Gly$_2$ linker, according to embodiments of the present invention.
Figure 10B:
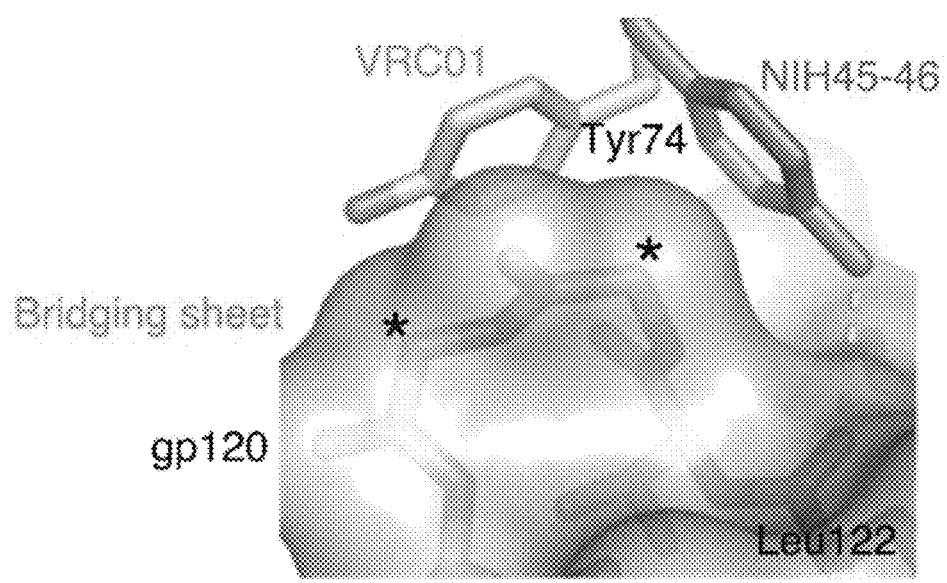
FIG. 10B is a close-up view of the structural depiction of FIG. 10A showing the hydrogen bond between Tyr74$_{NIH45-46}$ and the main-chain carbonyl oxygen of Leu122$_{gp120}$, according to embodiments of the present invention.

The insertion in CDRH3 contributes to a higher total buried surface area between the NIH45-46 heavy chain and gp120 compared with VRC01. (Table 5, below). The extra contacts with gp120 created by the CDRH3 insertion allow the NIH45-46 footprint on gp120 to more closely resemble the CD4 footprint on gp120 than does the VRC01 footprint (FIGS. 9C, 9D, and 9E, and Tables 5A and 5B, below).

TABLE 5A

| | Buried Surface Area (Å²) | | | | | | | | |
|---|---|---|---|---|---|---|---|---|---|
| | FWR1 | CDR1 | FWR2 | CDR2 | FWR3 | CDR3 | Total Fab | Interface on gp120 | CDR2 + FWR3$_{56\text{-}65}$* |
| NIH45-46 HC | 0 | 35 | 51 | 181 | 551 | 326 | 1144 | 1097 | 576 |
| VRC01 HC | 0 | 20 | 98 | 136 | 521 | 117 | 892 | 882 | 545 |
| NIH45-46 LC | 35 | 8 | 0 | 0 | 0 | 159 | 203 | 192 | 0 |
| VRC01 LC | 36 | 114 | 0 | 0 | 0 | 165 | 314 | 367 | 0 |

*Residues that correspond to the CDR2 region as defined in Zhou et al., Science, 2010, 329: 811-817.

TABLE 5B

| | Inner domain & bridging sheet | Loop D + NAG | β-15/α-3 + NAG | V5 | β-24 | Outer domain exit loop | Total gp120 | Interface on Fab or CD45 |
|---|---|---|---|---|---|---|---|---|
| NIH45-46 | 328 | 335 | 222 | 292 | 81 | 35 | 1290 | 1346 |
| VRC01 | 157 | 433 | 208 | 328 | 43 | 57 | 1225 | 1206 |
| CD4 | 400 | 136 | 263 | 155 | 14 | 97 | 973 | 1059 |

The observation that NIH45-46 shows more extensive contacts relative to VRC01 with the inner domain and bridging sheet of gp120 (FIGS. 9D and 9E), yet exhibits higher potency and breadth (Sheid et al., 2001, supra), is inconsistent with the suggestion that increased contact area with regions outside of the outer domain of gp120 correlate with decreased neutralization potency and/or breadth (Zhou et al., 2010 supra; and Wu et al, 2011, Science, 333:1593-1602). Indeed, the Observed CDRH3 contacts with the inner domain imply that the crystallographically-observed conformation of this region, whether pre-existing or induced, actively played a role in the affinity maturation events that resulted in the four-residue insertion with CDRH3.

Example 2

Hydrophobic Amino Acid Substitution at Position 54 of NIH45-46

Although NIH45-46 increases its contacts with the inner domain/bridging sheet area of gp120, like VRC01, it lacks a critical CD4 contact to a hydrophobic pocket at the boundary between the gp120 bridging sheet and outer domain made by burying Phe43$_{CD4}$. This residue alone accounts for 23% of the interatomic contacts between CIA and gp120, serving as a "linchpin" that welds CD4 to gp120 (Kwong et al., 1998, Nature, 393:648-659). On gp120, the Phe43 binding cavity is a binding site of small-molecule CD4 mimics (Madani et al., 2008, Structure, 16:1689-1701), and a desirable target for compounds to disrupt CD4-gp120 interactions (Kwong et al., 1998, supra), yet it remains unfilled in the 93TH057 complexes with VRC01 (Zhou et al., 2010, supra) and NIH45-46. In a superimposition of a CD4-gp120 structure and NIH45-46-gp120 (FIG. 9B), the Cα atom of heavy chain residue Gly54$_{NIH45\text{-}46}$ is only about 1.4 Å from the Phe43$_{CD4}$ Cα, suggesting that this important interaction might be mimicked by substituting Gly54$_{NIH45\text{-}46}$ with a large hydrophobic residue. Indeed, residue 54 of VRC03 is a tryptophan, and Trp54$_{VRC03}$ is accommodated within gp120's Phe43 binding cavity to mimic Phe43$_{CD4}$, while still maintaining its main-chain hydrogen bond with Asp368$_{gp120}$ (PDB 3SE8) (FIGS. 6A-6C). If increasing contacts with the inner domain/bridging sheet enhances antibody activity, as suggested by analysis of the NIH45-46-gp120 structure, then substituting Gly54$_{NIH45\text{-}46}$ with a large hydrophobic residue should increase the potency and breadth of NIH45-46.

A series of NIH45-46 mutants were constructed to test the possibility that a hydrophobic sidechain at position 54 in NIH45-46 would improve activity. First it was verified that substitutions at residue 54 did not interfere with antigen binding by assessing the ability of one mutant, NIH45-46$^{G54W}$, to bind core gp120s. Surface plasmon resonance (SPR) binding analyses demonstrated that NIH45-46$^{G54W}$ Fab bound core gp120s with slightly higher affinities than did NIH45-46 Fab, with differences largely due to slower dissociation rates (FIGS. 13A, 13B, and 13C). Next mutant IgGs were evaluated in neutralization assays using a panel of six viruses chosen to include NIH45-46-sensitive and resistant strains (Table 6, below).

TABLE 6

| | | NIH45-46 IC$_{50}$ (µg/mL) | | | | | | |
|---|---|---|---|---|---|---|---|---|
| Virus | Clade | WT | G54W | G54F | G54Y | G54I | G54M | G54L | G54H |
| SC422661.8 | B | 0.06 | 0.03 | 0.02 | 0.06 | 0.1 | 0.06 | 0.1 | 0.09 |
| AC10.0.29 | B | 0.9 | 0.2 | 0.3 | 0.4 | 8.6 | 1.5 | 1.7 | 0.6 |
| TRO.11 | B | 1.0 | 0.09 | 0.08 | 0.1 | 10 | 0.3 | 0.3 | 0.2 |
| Du172.17 | C | >50 | 0.9 | 16 | >50 | >50 | >50 | >50 | >50 |
| CAP210.2.00.E8 | C | >50 | 41 | >50 | >50 | >50 | >50 | >50 | >50 |
| CAP45.2.00.G3 | C | >50 | 6.6 | >50 | 45 | >50 | >50 | >50 | >50 |

NIH45-46$^{G54W}$ and NIH45-46$^{G54F}$ showed increased potencies and NIH45-46$^{G54W}$ increased breadth by neutralizing three strains that are resistant to >50 μg/mL of NIH45-46. The apparent increase in breadth is likely due to increased potency as evidenced by the extrapolated IC$_{50}$ for NIH45-46 against strain DU172.17 (FIG. 14).

An additional 82 viruses were tested including 13 NIH45-46-resistant, 14 weakly-neutralized, and 55 sensitive strains representing all clades, of which 12 are transmitted founder viruses (FIG. 15A, and Tables 7 and 8, below).

TABLE 7

In vitro neutralization IC$_{50}$ values (μg/mL) in the "hard panel" of viruses

| | | | NIH45-46 IC$_{50}$ (μg/mL) | | | |
|---|---|---|---|---|---|---|
| Virus | Clade | Category | WT | G54W | G54F | G54Y |
| 6545.v4.cl | AC | R | >50 | 18.92 | >50 | >50 |
| 6540.v4.cl | AC | R | >50 | >50 | >50 | >50 |
| CAP45.2.00.G3 | C | R | >50 | 32.25 | >50 | >50 |
| Du422.1 | C | R | >50 | >50 | >50 | >50 |
| CAP210.2.00.E8 | C | R | >50 | >50 | >50 | >50 |
| 3817.v2.c59 | CD | R | >50 | >50 | >50 | >50 |
| 89-F1_2_25 | CD | R | >50 | >50 | >50 | >50 |
| 620345.c01 | CRF01_AE | R | >50 | >50 | >50 | >50 |
| T250-4 | CRF02_AG | R | >50 | 1.33 | >50 | >50 |
| T278-50 | CRF02_AG | R | >50 | >50 | >50 | >50 |
| 211-9 | CRF02_AG | R | >50 | 16.41 | >50 | >50 |
| 3016.v5.c45 | D | R | >50 | 1.47 | 5.82 | 17.89 |
| Du172.17 | C | R | >50 | 3.65 | >50 | >50 |
| 3718.v3.c11 | A | P | 19.61 | 0.01 | 0.32 | 0.30 |
| 703357.C02 | CRF01_AE | P | 19.17 | 3.43 | 7.91 | 5.60 |
| CNE20 | BC | P | 7.83 | 0.04 | 0.53 | 0.33 |
| CNE21 | BC | P | 6.01 | 0.03 | 0.12 | 0.07 |
| HIV-16845-2.22 | C | P | 5.00 | 0.45 | 0.59 | 0.59 |
| C2101.c01 | CRF01_AE | P | 4.24 | 0.04 | 0.11 | 0.09 |
| ZM247v1(Rev-) | C | P, T/F | 2.94 | 0.32 | 0.28 | 0.42 |
| ZM233M.PB6 | C | P | 2.50 | 0.02 | 0.22 | 0.16 |
| C1080.c03 | CRF01_AE | P | 2.48 | 0.20 | 0.36 | 0.29 |
| THRO4156.18 | B | P | 1.91 | 0.54 | 0.89 | 0.66 |
| 3103.v3.c10 | ACD | P | 1.770 | 0.200 | 0.370 | 0.300 |
| 231966.c02 | D | P | 1.640 | 0.020 | 0.060 | 0.060 |
| TRO.11 | B | P | 1.610 | 0.040 | 0.110 | 0.080 |
| T251-18 | CRF02_AG | P | 1.350 | 0.260 | 0.410 | 0.350 |
| Ce1176_A3 | C | S, T/F | 0.930 | 0.160 | 0.240 | 0.210 |
| QH0692.42 | B | S | 0.720 | 0.370 | 0.560 | 0.520 |
| T255-34 | CRF02_AG | S | 0.710 | <0.001 | 0.030 | 0.040 |
| ZM135M.PL10a | C | S | 0.590 | 0.040 | 0.130 | 0.090 |
| AC10.0.29 | B | S | 0.560 | 0.130 | 0.240 | 0.190 |
| T257-31 | CRF02_AG | S | 0.490 | 0.130 | 0.170 | 0.180 |
| CNE58 | BC | S | 0.430 | 0.020 | 0.040 | 0.040 |
| Ce0393_C3 | C | S, T/F | 0.334 | 0.013 | 0.040 | 0.036 |
| R1166.c01 | CRF01_AE | S | 0.310 | 0.130 | 0.400 | 0.240 |
| CNE30 | BC | S | 0.309 | 0.052 | 0.100 | 0.099 |
| CNE17 | BC | S | 0.261 | 0.036 | 0.075 | 0.073 |
| X2131_C1_B5 | G | S | 0.230 | 0.050 | 0.100 | 0.100 |
| 928-28 | CRF02_AG | S | 0.230 | 0.060 | 0.110 | 0.120 |
| 6535.3 | B | S | 0.230 | 0.030 | 0.070 | 0.080 |
| ZM53M.PB12 | C | S | 0.175 | 0.040 | 0.080 | 0.060 |
| ZM214M.PL15 | C | S | 0.170 | 0.030 | 0.090 | 0.060 |
| Ce703010054_2A2 | C | S, T/F | 0.159 | 0.027 | 0.020 | 0.022 |
| ZM197M.PB7 | C | S | 0.150 | 0.040 | 0.090 | 0.070 |
| CAAN5342.A2 | B | S | 0.150 | 0.070 | 0.100 | 0.100 |
| Q23.17 | A | S | 0.140 | 0.010 | 0.030 | 0.020 |
| PVO.4 | B | S | 0.120 | 0.050 | 0.070 | 0.060 |
| 1054_07_TC4_1499 | B | S, T/F | 0.113 | 0.040 | 0.076 | 0.064 |
| Ce2010_F5 | C | S, T/F | 0.101 | 0.038 | 0.046 | 0.049 |
| ZM109F.PB4 | C | S | 0.095 | 0.002 | 0.022 | 0.026 |
| 1056_10_TA11_1826 | B | S, T/F | 0.094 | 0.024 | 0.064 | 0.044 |
| 0330.v4.c3 | A | S | 0.090 | 0.030 | 0.040 | 0.030 |
| P1981_C5_3 | G | S | 0.080 | 0.020 | 0.030 | 0.040 |
| Q461.e2 | A | S | 0.076 | 0.009 | 0.030 | 0.023 |
| P0402_c2_11 | G | S | 0.073 | 0.003 | 0.008 | 0.012 |
| SC422661.8 | B | S | 0.060 | 0.020 | 0.040 | 0.040 |
| 62357_14_D3_4589 | B | S | 0.060 | 0.020 | 0.040 | 0.030 |
| WITO4160.33 | B | S | 0.060 | 0.010 | 0.020 | 0.030 |
| Ce2060_G9 | C | S, T/F | 0.058 | 0.005 | 0.022 | 0.021 |
| Ce0682_E4 | C | S, T/F | 0.054 | 0.010 | 0.011 | 0.017 |
| 231965.c01 | D | S | 0.051 | <0.001 | 0.022 | 0.025 |
| Q259.d2.17 | A | S | 0.043 | <0.001 | 0.009 | 0.009 |
| TROJO4551.58 | B | S | 0.040 | 0.010 | 0.030 | 0.030 |
| 6811.v7.c18 | CD | S | 0.035 | <0.001 | 0.017 | 0.011 |

TABLE 7-continued

In vitro neutralization IC$_{50}$ values (µg/mL) in the "hard panel" of viruses

| | | | NIH45-46 IC$_{50}$ (µg/mL) | | | |
|---|---|---|---|---|---|---|
| Virus | Clade | Category | WT | G54W | G54F | G54Y |
| R2184.c04 | CRF01_AE | S | 0.034 | 0.005 | 0.015 | 0.015 |
| 6480.v4.c25 | CD | S | 0.032 | 0.004 | 0.014 | 0.018 |
| X1254

TABLE 8-continued

In vitro neutralization $IC_{80}$ values (μg/mL) in the "hard pane"l of viruses

| | | | | NIH45-46 $IC_{80}$ (μg/mL) | | |
|---|---|---|---|---|---|---|
| Virus | Cade | Category | WT | G54W | G54F | G54Y |
| 6535.3 | B | S | 0.54 | 0.13 | 0.27 | 0.24 |
| Ce703010054_2A2 | C | S, T/F | 0.538 | 0.077 | 0.070 | 0.070 |
| Q23.17 | A | S | 0.50 | 0.03 | 0.07 | 0.06 |
| 1056_10_TA11_1826 | B | S, T/F | 0.447 | 0.160 | 0.283 | 0.189 |
| ZM109F.PB4 | C | S | 0.437 | 0.070 | 0.17 | 0.168 |
| PVO.4 | B | S | 0.41 | 0.16 | 0.25 | 0.18 |
| 1054_07_TC4_1499 | B | S, T/F | 0.404 | 0.165 | 0.283 | 0.236 |
| CAAN5342.A2 | B | S | 0.40 | 0.21 | 0.28 | 0.27 |
| Ce2010_F5 | C | S, T/F | 0.357 | 0.187 | 0.186 | 0.235 |
| 0330.v4.c3 | A | S | 0.3 | 0.11 | 0.13 | 0.09 |
| Q461.e2 | A | S | 0.291 | 0.091 | 0.135 | 0.103 |
| Ce2060_G9 | C | S, T/F | 0.290 | 0.042 | 0.085 | 0.068 |
| WITO4160.33 | B | S | 0.26 | 0.04 | 0.14 | 0.09 |
| P1981_C5_3 | G | S | 0.24 | 0.07 | 0.11 | 0.09 |
| P0402_c2_11 | G | S | 0.214 | 0.023 | 0.047 | 0.049 |
| 1006_11_C3_1601 | B | S, T/F | 0.196 | 0.008 | 0.024 | 0.021 |
| 62357_14_D3_4589 | B | S, T/F | 0.19 | 0.07 | 0.14 | 0.09 |
| Ce0682_E4 | C | S, T/F | 0.155 | 0.039 | 0.056 | 0.065 |
| Q259.d2.17 | A | S | 0.154 | 0.014 | 0.036 | 0.034 |
| SC422661.8 | B | S | 0.13 | 0.07 | 0.10 | 0.09 |
| TRJO4551.58 | B | S | 0.13 | 0.05 | 0.08 | 0.07 |
| R2184.04 | CRF01_AE | S | 0.127 | 0.036 | 0.054 | 0.045 |
| 231965.c01 | D | S | 0.126 | 0.035 | 0.062 | 0.054 |
| 6811.v7.c18 | CD | S | 0.113 | 0.033 | 0.063 | 0.059 |
| X1254_c3 | G | 5 | 0.107 | 0.018 | 0.043 | 0.041 |
| 6480.v4.c25 | CD | S | 0.100 | 0.021 | 0.046 | 0.051 |
| C3347.c11 | CRF01_AE | S | 0.094 | 0.028 | 0.059 | 0.052 |
| 3415.v1.c1 | A | S | 0.086 | 0.023 | 0.029 | 0.037 |
| Q842.d12 | A | S | 0.073 | 0.025 | 0.039 | 0.045 |
| X1193_c1 | G | S | 0.064 | 0.009 | 0.026 | 0.024 |
| Du156.12 | C | S | 0.054 | 0.005 | 0.019 | 0.026 |
| ZM249M.PL1 | C | S | 0.053 | 0.007 | 0.016 | 0.011 |
| 0815.v3.c3 | ACD | S | 0.052 | 0.003 | 0.014 | 0.015 |
| RHPA4259.7 | B | S | 0.047 | 0.007 | 0.020 | 0.020 |
| CNE53 | BC | S | 0.039 | 0.005 | 0.024 | 0.027 |
| REJO4541.67 | B | S | 0.035 | 0.013 | 0.028 | 0.020 |
| 3301.v1.c24 | AC | S | 0.033 | 0.004 | 0.011 | 0.014 |
| Q769.d22 | A | S | 0.033 | 0.009 | 0.023 | 0.024 |
| WEAU_d15_410_787 | B | S, T/F | 0.015 | 0.003 | 0.004 | 0.008 |
| Geometric means | | | 1.231 | 0.225 | 0.437 | 0.393 |

Category R - Resistant S - Sensitive P - Poorly sensitive T/F - Transmitted Founder The above panel of viruses in Tables 7 and 8 (referred to as the "hard panel") is more difficult for NIH45-46$^{G54W}$ to neutralize than a recently-published panel (Sheid et al, 2011, supra) (FIG. 15B). NIH45-46$^{G54W}$ showed increased potency and breadth compared to NIH45-46 and VRC01: geometric mean $IC_{50}$s of 0.04 μg/mL for NIH45-46$^{G54W}$, 0.41 μg/mL for NIH45-46, and 0.92 μg/ml, for VRC01 (calculated for 65 viruses against which VRC01 was previously evaluated (Sheid et al, 2011, supra) (Tables 7 and 8, and FIG. 15C). (Geometric $IC_{50}$s values were calculated without excluding resistant strains by entering values of 50 μg/ml for strains with $IC_{50}$ values greater than 50 μg/ml)

TABLE 9

Sequence correlates of resistance to NIH45-46 Strain

| 620345_c1 | Ser456 (Arg) | Asp459 (Gly) | Lys279 (Asn/Asp) |
|---|---|---|---|
| 89_F1_2_25 | Ser456 (Arg) | Asn458 (Gly) | |
| 6540_v4_c1 | Ser456 (Arg) | Tyr458 (Gly) | Ser280 (Asn) |
| 6545_v4_c1 | Ser456 (Arg) | Tyr458 (Gly) | Ser280 (Asn) |
| Du422.1 | Trp456 (Arg) | | |
| T250_4 | Pro459 (Gly) | | |
| T278_50 | Glu459 (Gly) | Ala279 (Asn/Asp) | |
| Ce1172_H1 | deletion of Gly459 | | |

TABLE 9-continued

Sequence correlates of resistance to NIH45-46 Strain

| X2088_c9 | Val459 (Gly) | | |
|---|---|---|---|
| H086.8 | Asp459 (Gly) | Lys279 (Asn/Asp) | |

As shown in Table 9, above, 10 of 17 NIH45-46-resistant strains (5 of 7 NIH45-46$^{G54W}$-resistant strains) have amino acid variations at NIH45-46-contacting residues that have a fully conserved residue (shown in parenthesis) in all NIH45-46 sensitive strains. These mutations occur in the β23 strand immediately preceding V5 and in loop D. The positions of underlined sites have been shown to be important in resistance to VRC01 as reported in Li et al., 2011, *J. Virol.,* 85:8954-8967.

The largest difference between sensitivity to NIH45-46 and sensitivity to VRC01 was in strain 3016.v5.c45 ($IC_{50}$s of >30 and 0.16 μg/mL, respectively). The most notable residue in 3016.v5.c45 is Tyr282 in loop D. This large residue may alter the conformation of loop D, which is closely contacted by the four-residue insertion in the NIH45-46 CDRH3. The absence of the insertion may permit VRC01 to better accommodate an altered loop D. The next largest NIH45-46/VPC01 difference, for strain C2101.c1 (12.78 vs.

0.36 µg/mL), may similarly relate to the unusual Lys99$_{gp120}$ residue replacing the asparagine that favorably interacts with Arg99b$_{NIH45-46}$ in the NIH45-46-gp120 crystal structure.

From the neutralization assays, it is noted that NIH45-46$^{G54W}$ gained de novo neutralization activity against six NIH45-46 resistant strains, including the only three that were sensitive to VRC01 but resistant to NIH45-46 in the panel tested in Sheid et al, 2011, supra. For some strains that NIH45-46 neutralizes poorly, NIH45-$46^{G54W}$ was significantly more potent (e.g., improvements of >700-fold for T255-34 and 2000-fold for 3718.v3.c11). The enhanced neutralization activity of NIH45-$46^{G54W}$ implies that Trp54 forms a favorable hydrophobic interaction with Phe43 cavity of gp120 as seen in VRC03-gp120 (PDB 3SE8). NIH45-$46^{G54F}$ showed some increased activity (Tables 6, 7 and 8).

Substituting Gly54 with tryptophan adds about 140 $Å^2$ of buried surface area on $V_H$ when complexed with gp120, and is consistent with the reduced dissociation rates observed in surface plasmon resonance (SPR) experiments (FIGS. 13A, 13B, and 13C). By providing a tryptophan in the Phe43 cavity of gp120, NIH45-$46^{G54W}$ may use higher affinities and/or slower dissociation rates to overcome incompatible surface variations that render some viruses less sensitive or resistant to its effects.

Heavy chain residue 54 is not conserved in HAADs; in addition to glycine (NIH45-46 and VRC01), residue 54 can be threonine (3BNC60, 3BNC117, 3BNC115; VRC-PG04), tyrosine (12A12), phenylalanine (12A21), or arginine (1B2530 and 1NC9), as reported in Sheid et al., 2011, supra; and Wu et al., 2011, supra. Tryptophan substitution in some HAADs was tested and shown in Table 10, below.

TABLE10

| In vitro neutralization $IC_{50}$ values (μg/mL) | | | | | | | | | |
|---|---|---|---|---|---|---|---|---|---|
| Virus | Clade | 3BNC60 WT | 3BNC60 T54W | 3BNC117 WT | 3BNC117 T54W | 3BNC55 WT | 3BNC55 T54W | 12A12 WT | 12A12 Y54W |
| SC422661.8 | B | 0.1 | 0.1 | 0.07 | 0.07 | 0.3 | 0.6 | 0.2 | 0.2 |
| AC10.0.29 | B | 13 | 3.1 | 6.5 | 2.8 | >50 | >50 | 0.6 | 0.5 |
| TRO.11 | B | 0.07 | 0.06 | 0.6 | 0.6 | 7.6 | >50 | 0.3 | 0.2 |
| Du172.17 | C | 0.05 | 0.04 | 0.04 | 0.9 | 2 | >50 | 0.2 | 0.1 |
| CAP210.2.00.E8 | C | 4.7 | 5.0 | 11 | 2.8 | >50 | >50 | >50 | >50 |
| CAP45.2.00.G3 | C | 10 | 19 | 16 | 23 | >50 | >50 | 0.4 | 0.2 |

Passive immunization and/or gene therapy to deliver HIV antibodies is increasingly being considered as an option for prevention of HIV infection. To reduce the concentrations and numbers of antibodies required for protection to realistic and affordable levels, highly potent and broadly neutralizing antibodies are the reagents of choice for passive delivery. Although it is difficult to compare the potencies and breadth of antibodies characterized using different virus panels, the natural form of NIH45-46 exhibits superior potency to VRC01 when compared against a panel of 82 Tier 2 and 3 viruses representing all known HIV clades (Sheid et al., 2011, supra). One set of HIV antibodies, the PGT antibodies that recognize the gp120 V3 loop and associated carbohydrates, exhibited median $IC_{50}$s up to 10-fold lower than VRC01 (Walker et at, 2011, *Nature,* 477:466-471, the entire contents of which are incorporated herein by reference), but are less potent and broad than NIH45-$46^{G54W}$ (FIG. 15B, and Table 11, below).

TABLE 11

| Isolate | PGT-121 | PGT-122 | PGT-123 | PGT-125 | PGT-126 | PGT-127 | PGT-128 | PGT-130 | PCT-131 | PGT-135 | PGT-136 | PGT-137 | PGT-141 | PGT-142 | PGT-143 | PGT-144 | PGT-145 | VRC01 | VRC-PG04 | PG9 |
|---|---|---|---|---|---|---|---|---|---|---|---|---|---|---|---|---|---|---|---|---|
| Include >50 (µg.mL) | | | | | | | | | | | | | | | | | | | | |
| Geometric mean | 0.53 | 1.03 | 0.66 | 1.85 | 1.05 | 2.92 | 0.39 | 3.07 | 7.27 | 9.53 | 30.39 | 23.53 | 3.15 | 2.40 | 3.14 | 13.62 | 0.91 | 0.45 | 0.57 | 1.27 |
| Arithmetic mean | 16.63 | 19.39 | 18.29 | 25.81 | 21.75 | 26.19 | 15.31 | 25.39 | 31.06 | 34.91 | 44.02 | 41.22 | 24.62 | 23.30 | 24.62 | 33.76 | 12.83 | 4.41 | 7.92 | 15.89 |
| Median | 0.31 | 2.02 | 0.35 | 34.97 | 1.08 | 42.83 | 0.10 | 22.98 | 50.00 | 50.00 | 50.00 | 50.00 | 16.01 | 9.46 | 13.76 | 50.00 | 0.86 | 0.34 | 0.30 | 0.62 |
| Exclude >50 (µg.mL) | | | | | | | | | | | | | | | | | | | | |
| Geometric mean | 0.07 | 0.13 | 0.08 | 0.09 | 0.08 | 0.17 | 0.06 | 0.24 | 0.41 | 0.32 | 2.25 | 1.68 | 0.33 | 0.24 | 0.34 | 1.58 | 0.30 | 0.32 | 0.30 | 0.36 |
| Arithmetic mean | 2.17 | 3.21 | 2.44 | 3.34 | 2.82 | 2.39 | 1.56 | 3.09 | 2.80 | 3.88 | 12.74 | 10.51 | 3.80 | 2.99 | 4.32 | 6.87 | 2.59 | 1.04 | 1.99 | 4.33 |
| Median | 0.03 | 0.05 | 0.03 | 0.04 | 0.04 | 0.08 | 0.02 | 0.16 | 0.52 | 0.17 | 7.81 | 3.46 | 0.35 | 0.21 | 0.31 | 2.06 | 0.29 | 0.32 | 0.20 | 0.23 |
| % viruses <50 (µg.mL) | 70% | 65% | 67% | 52% | 60% | 50% | 72% | 52% | 40% | 33% | 16% | 22% | 55% | 57% | 56% | 38% | 78% | 92% | 88% | 75% |

Table 11 above shows a comparison of mean and median $IC_{50}$ (μg/mL) values for PGT antibodies and VRC01. A direct comparison between NIH45-46 and the PGT antibodies is not available. However, VRC01 (which was shown in a direct comparison to be less potent than NIH45-46) was directly compared to the PGT antibodies using the same virus panel. (Sheid et al., 2011, supra.) Mean $IC_{50}$ values were calculated using data taken from Sheid et al., 2011, supra. Geometric and arithmetic means were calculated to include data for all viral strains (listed as Include >50, in which case, values reported as $IC_{50}$>50 μg/mL were entered as 50 μg/mL in the calculation) and to exclude viral strains in which the $IC_{50}$ was >50 μg/mL, (listed as Exclude >50, in which case the percent of viral strains with $IC_{50}$s<50 μg/mL is also reported). Mean $IC_{50}$s are compared with the median $IC_{50}$s as reported in Sheid et al., 2011, supra.

Contacts between the antibody light chain and gp120 are mostly conserved between the NIH45-46-93THO57 and VRC01-93TH-057 structures with a notable exception: $Ser28_{NIH45\text{-}46\ LC}$ in CDRL1 replaces a solvent-exposed tyrosine ($Tyr28_{VRC01\ LC}$) that interacts with ordered N-linked carbohydrate attached to $Asn276_{93TH057}$. By contrast, the $Ser28_{NIH45\text{-}46\ LC}$ sidechain does not contact gp120 carbohydrates; instead it faces away from gp120, hydrogen bonding with $Arg64_{NIH45\text{-}46\ LC}$ (FWR3) and creating a 2.7 Å displacement of the main-chain Cα atoms (FIG. 11A). The $Ser28_{NIH45\text{-}46\ LC}$-$Arg64_{NIH45\text{-}46\ LC}$ interaction is maintained in unbound NIH45-46 (FIG. 11B). The position 28 substitution of serine for tyrosine largely accounts for the burial of more surface area in gp120's interaction with the VRC01 versus NIH45-46 light chain (681 Å$^2$ versus 395 Å$^2$ total buried surface area; 314 Å$^2$ versus 203 Å$^2$ buried surface area on the light chain) (Tables 5A, 5B). The larger contact area for the VPC01 light chain may account for the ability of VRC01, but not NIH45-46, to neutralize the Glade C CAP45.2.00.G3 strain, given that the NIH45-46 heavy chain paired with the VRC01 light chain neutralizes this strain, whereas the VRC01 heavy chain paired with the NIH45-46 light chain does not (Table 12). However, the VRC01 light chain did not increase the potency of NIH45-46 against three other viral strains (Table 12), suggesting that the Tyr28 interaction with gp120 carbohydrate is not obligatory.

TABLE 12

In vitro neutralization $IC_{50}$ values (μg/mL)

| Virus | Clade | NIH45-46 | NIH45-46 HC VRC01 LC | VRC01 HC NIH45-46 LC | VRC01 |
|---|---|---|---|---|---|
| AC10.0.29 | B | 0.9 | 1.0 | 4.5 | 0.8 |
| TRO.11 | B | 1.9 | 0.3 | 24 | 0.5 |
| SC422661.8 | B | 0.05 | 0.2 | 0.4 | 0.2 |
| QH0692.42 | B | 0.7 | 0.9 | 1.2 | 0.7 |
| ZM214M.PL15.11 | C | 0.5 | 0.6 | 1.8 | 0.8 |
| CAP45.2.00.G3 | C | >50 | 2.1 | >50 | 1.8 |
| T257-31 | CRF02 (A/G) | 0.5 | 0.6 | 15 | 1.0 |

Example 3

Protein Expression and Purification

Proteins were produced and purified using previously-described methods (Diskin et al., 2010, Nat. Struct. Mol. Biol., 17:608-613, the entire contents of which are incorporated herein by reference). Briefly, NIH45-46 IgG was expressed by transient transfection in HEK293-6E cells. Secreted IgG was purified from cell supernatants using protein A affinity chromatography (GE Healthcare). Fab fragments were prepared by digesting purified IgG with immobilized papain (Pierce) at 10 mg/mL and then separating Fabs from Fc-containing proteins using protein A chromatography and Superdex 200 16/60 size exclusion chromatography. For crystallization trials, the NIH45-46 Fab for crystallization experiments was concentrated to 11 mg/mL in 20 mM Tris pH 8.0, 150 mM sodium chloride, 0.02% sodium azide (TBS). Substitutions in heavy chain residue 54 of NIH45-46, 3BNC55, 12A12, 3BNC117 and 3BNC60 were introduced using a Quikchange II kit (Agilent technologies). Wild type, mutant forms and chain swapped versions of these proteins were expressed as IgGs in HEK293-6E cells and purified by protein A chromatography as described for NIH45-46 IgG. Proteins were stored at a concentration of 1 mg/mL for neutralization assays in either 10 mM sodium citrate pH 3.05, 50 mM sodium chloride, 0.02% sodium azide or in TBS (12A12 and $12A12^{Y54W}$) or in phosphate buffered saline (NIH45-46 mutated/truncated in CDRH3 and NIH45-46/VRC01 heavy and light chain swapped antibodies (Abs)) prior to dilution into neutral pH cell media. For SPR analyses, NIH45-46 and NIH45-46$^{G54W}$ heavy chains were subcloned into the pTT5 (NRC-BRI) expression vector to encode C-terminal 6×-His tagged Fab heavy chains ($V_H$-$C_H$1-6×-His tag), and the heavy chain expression vectors were co-transfected with the appropriate light chain vector into HEK293-6E cells. Supernatants were collected after 7 days, buffer exchanged into TBS and loaded on a Ni$^{2+}$-NTA affinity column (Qiagen). Fabs were eluted using TBS supplemented with 2:50 mM imidazole and further purified by Superdex200 10/300 size exclusion chromatography (GE Healthcare) in TBS.

Genes encoding truncated 93TH053, CAP244.2.00.D3, and Q259.d2.17 gp120 cores including the deletions and modifications described in Zhou et al., 2010, supra (the entire contents of which are incorporated herein by reference), were chemically synthesized (BlueHeron). An extra disulfide bond was introduced into 93TH053 by changing the Val65 and Ser115 codons into cysteines.

The modified core genes were subcloned into the pACgp67b expression vector (BD Biosynthesis) to include a C-terminal 6×-His tag, expressed in baculovirus-infected insect cells, and purified from insect cell supernatants as previously described in Diskin et al., 2010, supra. For crystallization experiments, purified NIH45-46 Fab and 93TH057 gp1.20 were incubated at a 1:1 molar ratio and treated with 40 kV of Endoglycosidase H (New England Biolabs) for 16 hours at 37° C. The complex was purified after the incubation by Superdex 200 10/300 size exclusion chromatography (GE Healthcare) and then concentrated to $OD_{280}$=9.6 in 20 mM Tris pH 8.0, 300 mM sodium chloride, 0.02% sodium azide.

Example 4

Crystallization

Crystallization screening was done by vapor diffusion in sitting drops by a Mosquito® crystallization robot (TTP labs) using 400 nL drops (1:1 protein to reservoir ratio) utilizing commercially available crystallization screens (Hampton. Initial crystallization hits for Fab NIH45-46 and for NIH45-46-93TH057 complex were identified using the PEGRx HT™ (Hampton) screen and then manually optimized. Thin needle-like crystals of Fab NIH45-46 (space group P2₁2₁2₁, a=49.4 Å, b=87.4 Å, c=166.4 Å; one molecule per asymmetric unit) were obtained upon mixing a protein solution at 11 mg/mL with 12% polyethylene glycol 20,000, 0.1 M sodium acetate pH 5.0, 0.1 M sodium/potassium tartrate, 0.02 M ammonium sulfate at 20° C. Crystals were briefly soaked in mother liquor solution supplemented with 15% and then 30% glycerol before flash cooling in liquid nitrogen. Crystals of the NIH45-46-93TH057 complex (space group P2₁2₁2₁, a=69.1 Å, b=70.5 Å, c=217.7 Å; one molecule per asymmetric unit) were Obtained upon mixing a protein solution at $OD_{280}$=9.6 with 12% isopropanol, 10% polyethylene glycol 10,000, 0.1 M sodium citrate pH 5.0 at 20° C. Complex crystals were cryo-cooled by covering the crystallization drops with paraffin oil to prevent evaporation and then adding an excess of 20% isopropanol, 5% glycerol, 10% polyethylene glycol, 0.1 M sodium citrate pH 5.0 to the drops prior to mounting and flash cooling the crystals in liquid nitrogen.

Example 5

Data Collection, Structure Solution and Refinement

X-ray diffraction data were collected at the Stanford Synchrotron Radiation Lightsource (SSRL) beamline 12-2 using a Pilatus 6M pixel detector (Dectris). The data were indexed, integrated and scaled using XDS as described in Kabsch, 2010, *Acta Crystallogr D Biol Crystallogr*, 66:125-132, the entire contents of which are incorporated herein by reference. The Fab NIH45-46 structure was solved by molecular replacement using Phaser as described in McCoy et al., 2007, *J. Appl. Cryst.*, 40:658-674, the entire contents of which are incorporated herein by reference, and the $V_HV_L$ and $C_H1C_L$ domains of the VRC01 Fab (PDB code 3NGB) as separate search models. The model was refined to 2.6 Å resolution using an iterative approach involving refinement using the Phenix crystallography package Adams et al., 2010, *Acta Crystallogr D Biol Crystallogr*, 66:213-221, the entire contents of which are incorporated herein by reference, and manually fitting models into electron density maps using Coot (Emsley et al., 2004, *Acta Crystallogr D Biol Crystallogr*, 60:2126-2132, the entire contents of which are incorporated herein by reference). The final model ($R_{work}$=18.4%; $R_{free}$=23.8%) includes 3380 protein atoms, 125 water molecules and 37 ligand atoms, including N-Acetylglucosamine, glycerol and a sulfate ion (FIG. 2). 96.5%, 3.3% and 0.2% of the residues were in the favored, allowed and disallowed regions, respectively, of the Ramachandran plot. The first glutamine of the NIH45-46 heavy chain was modeled as 5-pyrrolidone-2-carboxylic acid.

A search model fir solving the NIH45-46-93TH057 complex was created by superimposing the refined structure of the NIH45-46 Fab on the VRC01 Fab in the structure of VRC01-93TH057 (PDB code 3NGB). A molecular replacement solution was found as described above using separate search models for the $V_HV_L$ domains of NIH45-46 complexed with 93TH057 and the $C_H1C_L$ domains of NIH45-46. (FIG. 2). The complex structure was refined to 2.45 Å resolution as described for the Fab structure. To reduce model bias, the CDRH3 of NIH45-46 was omitted from the model and then built into electron density maps after a few rounds of refinement. The final model ($R_{work}$=20.7%; $R_{free}$=25.6%) includes 5989 protein atoms, 67 water molecules and 148 atoms of carbohydrates, citrate and chloride ions (FIG. 2). 96.1%, 3.5% and 0.4% of the residues were in the favored, allowed and disallowed regions, respectively, of the Ramachandran plot. Disordered residues that were not included in the model were residues 1-2 of the NIH45-46 light chain, residues 133-136 and 219-221 of the heavy chain, and residues 302-308 (V3 substitution), residues 397-408 (a total of 6 residues from V4) and the 6×-His tag of 93TH057. The first glutamine of the NIH45-46 heavy chain was modeled as 5-pyrrolidone-2-carboxylic acid.

Buried surface areas were calculated using AreaIMol in CCP4 and a 1.4 Å probe. Superimposition calculations were done and molecular representations were generated using PyMol (The PyMOL Molecular Graphics System, Schrödinger, LLC).

Example 6

Surface Plasmon Resonance (SPR) Measurements

The binding of gp120 core proteins to wild-type NIH45-46 Fab and to mutant (NIH45-46$^{G54W}$) Fab was compared using a Biacore T100 instrument (GE Healthcare). Purified NIH45-46 and NIH45-46$^{G54W}$ Fabs were immobilized at coupling densities of 500 resonance units (RU) or 1500 RU on a CM5 sensor chip (Biacore) in 10 mM acetate pH 5.0 using primary amine coupling chemistry as described in the Biacore manual. One of the four flow cells on each sensor chip was mock-coupled using buffer to serve as a blank. Experiments were performed at 25° C. in 20 mM HEPES, 7.0, 150 mM sodium chloride and 0.005% (v/v) surfactant P20, and the sensor chips were regenerated using 10 mM glycine, 2.5. gp120 core proteins were injected in a two-fold dilution series at concentrations ranging from 500 nM to 31.2 nM at a flow rate of 70 µL/min. After subtracting the signal from the mock-coupled flow cell, kinetic data were globally fit to a 1:1 binding model (Biacore evaluation software) to derive on- and off-rate constants, which were used to calculate affinities as $K_D=k_d/k_a$.

Example 7

In Vitro Neutralization Assays

A previously-described pseudovirus neutralization assay was used to compare the neutralization potencies of wild-type and mutant IgGs as previously described in Montefiori, 2005, *Current protocols in immunology*, Edited by John E. Coligan et al., Chapter 12, Unit 12.11, the entire contents of which are incorporated herein by reference. Briefly, pseudoviruses were generated in HEK293T cells by co-transfection of an Env-expressing vector and a replication-incompetent backbone plasmid. Neutralization was assessed by measuring the reduction in luciferase reporter gene expression in the presence of a potential inhibitor following a single round of pseudovirus infection in TZM-bl cells. Antibodies were pre-incubated with 250 infectious viral units in a three or four-fold dilution series for one hour at 37° C. before adding 10,000 TZM-bl cells per well for a two-day incubation. Cells were then lysed and luciferase expression was measured using BrightGlo (Promega) and a Victor3 luminometer (PerkinElmer). Nonlinear regression analysis using the program Prism (GraphPad) was used to calculate the concentrations at which half-maximal inhibition was observed ($IC_{50}$ values) as described in Klein et al., 2009, *PNAS*, 106:7385-7390, the entire contents of which are incorporated herein by reference. Samples were initially screened in duplicates. Reagents that showed enhanced activity were tested again as triplicates. Values for NIH45-46 and NIH45-46$^{G54W}$ in FIG. 14 were obtained from three independent experiments. Similar IC$_{50}$ values were obtained in two independent neutralization experiments using different dilution series.

Example 8

Signature Features of ITT Antibodies

The correlation between neutralization potency and the length of two of the light chain CDR, loops was analyzed in CD4bs antibodies. The relatively small CDRL1 of VRC01, which has a 2-residue deletion relative to its germline precursor, was previously correlated with increased neutralization potency (Zhou et al., 2010, supra). It was noted that sequences of VRC01, NIH45-46, and VRC-PG04 revealed a more striking correlation for the length of CDRL3, which is only 5 residues in these antibodies. Examination of the large Abysis database for human Ab sequences (http://www.bioinf.org.uk/abs/) showed that only about 1% of V$_L$ domains have a CDRL3 length of 5 amino acids, compared with more typical 9-11 residue lengths. Larger CDRL3 loops would place critical side chains at the tip of CDRL3 in different locations, thus not able to interact with gp120 in the same manner. In antibodies with longer CDRL3s, the tip of CDRL3 interacts with Trp47$_{HC}$, a highly conserved residue (found in 63 of 69 germline V$_H$ gene segments) that plays a similar role as Trp102$_{HC}$ in the Abs with 5-residue CDRL3s to stabilize the V$_H$-V$_L$ interface.

V domain alignments revealed the following sequence characteristics of the most potent of the VRC01-like Abs: complete conservation of heavy chain Arg71$_{HC}$, Trp50$_{HC}$, Asn58$_{HC}$, and Trp102$_{HC}$, and light chain Glu90$_{LC}$, Trp65$_{LC}$/Phe65$_{LC}$ and a CDRL3 length of exactly 5 amino acids (residues are numbered here as in the structure of NIH45-46; pdb code 3U7Y). Analysis of the per residue variability of VH1-2*02-derived Abs indicates that the conservation of Trp50$_{HC}$ and Asn58$_{HC}$ is unlikely to be coincidental.

The roles that conserved residues play in the V$_H$ domain structure and in binding to the CD4bs on gp1.20 are shown schematically in FIG. 16 and Table 13, below. The figures are based on interactions present in the gp120 complexes of VRC01, NIH45-46, and VRC-PG04 (Wu et al., 2011, *Science*, 333:1593-1602; Diskin et al., 2011, *Science*, 334: 1289-1293; and Zhou et al., 2010, *Science*, 329:811-817, the entire contents of all of which are incorporated herein by reference.

TABLE 13

PVL Features

| PVL Characteristic feature | Role |
|---|---|
| Trp50$_{HC}$ | H bond with Asn280$_{gp120}$ |
| Asn58$_{HC}$ | H bond with Arg456$_{gp120}$ |
| Arg71$_{HC}$ | H bond/salt bridge with Asp368$_{gp120}$ |
| Trp102*$_{HC}$ | H bond with Asn/Asp279$_{gp120}$ |
| Glu90**$_{LC}$ | H bond with Gly459$_{gp120}$ |
| Trp65***$_{LC}$/Phe65***$_{LC}$ | interaction with Asn276$_{gp120}$ glycan |
| 5-residue CDRL3 | prevent steric clashes, position 89$_{LC}$ & 90$_{LC}$ side chains |

*Position Trp100B;
**Postion Glu96; and
***Trp67/Phe67 using Kabat numbering system.

The side chains of Trp50$_{HC}$, Trp102$_{HC}$, and Trp47$_{HC}$ form an unusual propeller-like arrangement on the surface the V$_H$ domain. (Although Trp47$_{HC}$ participates in the "propeller," it is not considered to be a signature residue of potent CD4bs antibodies because it is commonly found in V$_H$ domains).

The main interactions of the characteristic V$_H$ domain residues with gp120 are as follows: Trp50$_{HC}$: indole N—H hydrogen bonds with the side chain oxygen of Asn280$_{gp120}$; Asn58$_{HC}$: side chain N—H hydrogen bonds with the backbone carbonyl of Arg456$_{gp120}$; Arg71$_{HC}$: side chain hydrogen bonds/salt bridges with the side chain of Asp368$_{gp120}$; and Trp102$_{HC}$: indole N—H hydrogen bonds with the side chain oxygen of Asn/Asp279$_{gp120}$. Trp102$_{HC}$ also buries 85 Å$^2$ of surface area at the V$_H$/V$_L$ interface—contacting residues Tyr89$_{LC}$ and Glu90$_{LC}$.

In the light chains, the side chain of Glu90$_{LC}$ forms a hydrogen bond with the backbone nitrogen of Gly459$_{gp120}$ and/or the side chain of Asn280$_{gp120}$. The conservation of Trp65$_{LC}$/Phe65$_{LC}$ is surprising as this position is distant from gp120 in the available crystal structures.

For those interactions that depend on specific gp120 side chains, the degree of conservation of the relevant gp120 residues is 96.4% for Asn/Asp279$_{gp120}$, 96.4% for Asn280$_{gp120}$, and 99.7% for Asp368$_{gp120}$ (based on the 2010 filtered web alignment of 2869 HIV-1 sequences in the Los Alamos HIV database; http://www.hiv.lanl.gov/). Arg456$_{gp120}$, which is involved in a main-chain hydrogen bond with the sidechain of Asn58$_{HC}$, is also highly conserved (95.0%).

An SPR-based binding assay demonstrated detectable binding of the germline heavy chain/mature light chain IgG to immobilized gp140 trimers. Binding of germline heavy chain IgGs was analyzed with substitutions in the four signature heavy chain residues (W50S, N58S, R71T, and W102S) (again paired with the mature 3BNC60 light chain). The W50S, R71T, and W102S mutants showed little or no gp140 binding, and the N58S mutation diminished binding by about 20-fold, consistent with the corresponding PVL characteristic residues playing key roles in recognition of the HIV-1 envelope spike by the germline PVL B cell receptor.

To examine the importance of the signature PVL residues to their activity, the gp120 sequences of HIV-1 strains resistant to neutralization by NIH45-46 were analyzed. The gp120 residue variants associated with resistance were identified by three criteria: first, they are contact residues with NIH45-46; second, they are absent in NIH45-46-resistant viruses; third, they do not appear in NIH45-46-sensitive viruses. The critical positions identified were 279$_{gp120}$, 280$_{gp120}$, 456$_{gp120}$, 458$_{gp120}$, and 459$_{gp120}$; the common (i.e., sensitive) residues at these positions are Asx, Asn, Arg, Gly, and Gly, respectively, where Asx is Asp or Asn. These sites make significant contacts with the characteristic PVL residues (FIG. 16). Viral stains with variations at these sites are generally neutralized poorly by all PVL antibodies, as expected if substitutions at these positions interfere with common interactions.

To verify the significance of gp120 variations at these positions, point mutants within the gp160 gene of HIV-1 strain YU2 were engineered, created pseudoviruses carrying the mutant gp160s, and determined the neutralization potencies of the PVL NIH45-46$^{G54W}$ (Diskin et al., 2011, supra) (as characterized by IC$_{50}$ values). Mutations at 279$_{gp120}$ and 280$_{120}$ rendered the virus resistant to neutralization by NIH45-46$^{G54W}$, and substitution of 458$_{gp120}$ diminished the neutralization potency by >1500-fold (FIG. 17).

Example 9

Neutralization of NIH45-46 Resistant HIV Strains with 45-46 m2 Antibody

In an effort to increase the breadth of NIH45-46$^{G54W}$, a S28Y substitution was introduced into the light chain of the NIH45-46$^{G54W}$ resulting in NIH45-46$^{G54W(HC), S28Y(LC)}$ (also referred to herein as 45-46 m2). This 45-46 m2 antibody was expressed and evaluated using in vitro neutralization assays against a cross-clade panel of 118 primary HIV isolates including transmitted founder viruses (Tables 14, 15, below

TABLE 14

| | | IC$_{50}$ | | |
|---|---|---|---|---|
| Virus ID | Clade* | NIH45-46 | NIH45-46$^{G54W}$ | 45-46m2 |
| T278-50 | CRF02_AG | >50 | >50 | >50 |
| 89-F1_2_25 | CD | >50 | >50 | >50 |
| 6540.v4.c1 | AC | >50 | >50 | >50 |
| Ce1172_H1 | C (T/F) | >50 | >50 | >50 |
| 620345.c01 | CRF01_AE | >50 | >50 | >50 |
| X2088_c9 | G | >50 | >50 | 44.345 |
| Du422.1 | C | >50 | >50 | 8.473 |
| 3817.v2.c59 | CD | >50 | >50 | 5.138 |
| CAP210.2.00.E8 | C | >50 | >50 | 1.945 |
| CAP45.2.00.G3 | C | >50 | 32.25 | 0.02 |
| 6545.v4.c1 | AC | >50 | 18.92 | 15.21 |
| 211-9 | CRF02_AG | >50 | 16.41 | 0.253 |
| Du172.17 | C | >50 | 3.65 | 0.015 |
| 3016.v5.c45 | D | >50 | 1.47 | 0.006 |
| T250-4 | CRF02_AG | >50 | 1.33 | 1.554 |
| 246F C1G | C (T/F) | >50 | 0.315 | 0.036 |
| CNE20 | BC | 7.83 | 0.04 | 0.001 |
| CNE21 | BC | 6.01 | 0.03 | 0.001 |
| HIV-16845-2.22 | C | 5 | 0.45 | 0.38 |
| C2101.c01 | CRF01_AE | 4.24 | 0.04 | 0.044 |
| ZM247v1(Rev-) | C (T/F) | 2.94 | 0.32 | 0.001 |
| ZM233M.PB6 | C | 2.5 | 0.02 | 0.011 |
| C1080.c03 | CRF01_AE | 2.48 | 0.2 | 0.154 |
| THRO4156.18 | B | 1.91 | 0.54 | 0.685 |
| 3103.v3.c10 | ACD | 1.77 | 0.2 | 0.181 |
| 231966.c02 | D | 1.64 | 0.02 | 0.012 |
| TRO.11 | B | 1.61 | 0.04 | 0.02 |
| T251-18 | CRF02_AG | 1.35 | 0.26 | 0.336 |
| Ce1176_A3 | C (T/F) | 0.93 | 0.16 | 0.172 |
| BJOX010000.06.2 | CRF01_AE (T/F) | 0.87 | 0.769 | 1.382 |
| QH0692.42 | B | 0.72 | 0.37 | 0.216 |
| T255-34 | CRF02_AG | 0.71 | 0.001 | 0.013 |
| ZM135M.PL10a | C | 0.59 | 0.04 | 0.049 |
| AC10.0.29 | B | 0.56 | 0.13 | 0.118 |
| T257-31 | CRF02_AG | 0.49 | 0.13 | 0.126 |
| 6240_08_TA5_4622 | B (T/F) | 0.44 | 0.11 | 0.173 |
| CNE58 | BC | 0.43 | 0.02 | 0.016 |
| Ce0393_C3 | C (T/F) | 0.334 | 0.013 | 0.046 |
| R1166.c01 | CRF01_AE | 0.31 | 0.13 | 0.278 |
| CNE30 | BC | 0.309 | 0.052 | 0.082 |
| 235-47 | CRF02_AG | 0.3 | 0.001 | 0.001 |
| CNE17 | BC | 0.261 | 0.036 | 0.064 |
| BJOX009000.02.4 | CRF01_AE | 0.26 | 0.132 | 0.14 |
| 928-28 | CRF02_AG | 0.23 | 0.06 | 0.045 |
| X2131_C1_B5 | G | 0.23 | 0.05 | 0.031 |
| 9004SS_A3_4 | A (T/F) | 0.18 | 0.054 | 0.046 |
| BJOX025000.01.1 | CRF01_AE (T/F) | 0.18 | 0.014 | 0.031 |
| ZM53M.PB12 | C | 0.175 | 0.04 | 0.091 |
| ZM214M.PL15 | C | 0.17 | 0.03 | 0.036 |
| Ce703010054_2A2 | C (T/F) | 0.159 | 0.027 | 0.016 |
| CAAN5342.A2 | B | 0.15 | 0.07 | 0.078 |
| ZM197M.PB7 | C | 0.15 | 0.04 | 0.074 |
| Ce704809221_1B3 | C (T/F) | 0.15 | 0.007 | 0.101 |
| 7030102001E5(Rev) | C (T/F) | 0.14 | 0.042 | 0.038 |
| 6535.3 | B | 0.14 | 0.03 | 0.015 |
| SC05_8C11_2344 | B (T/F) | 0.14 | 0.021 | 0.07 |
| Q23.17 | A | 0.14 | 0.01 | 0.015 |
| C4118.c09 | CRF01_AE | 0.14 | 0.01 | 0.011 |
| PVO.4 | B | 0.12 | 0.05 | 0.014 |
| 1054_07_TC4_1499 | B (T/F) | 0.113 | 0.04 | 0.104 |
| 191955_A11 | A (T/F) | 0.11 | 0.015 | 0.013 |
| Ce2010_F5 | C (T/F) | 0.101 | 0.038 | 0.03 |
| ZM109F.PB4 | C | 0.095 | 0.002 | 0.013 |
| 1056_10_TA11_1826 | B (T/F) | 0.094 | 0.024 | 0.057 |
| MS208.A1 | A | 0.09 | 0.031 | 0.022 |
| 191821_E6_1 | D (T/F) | 0.09 | 0.013 | 0.05 |
| CNE5 | CRF01_AE | 0.09 | 0.009 | 0.032 |
| 1394C9G1(Rev-) | C (T/F) | 0.09 | 0.001 | 0.012 |
| P1981_C5_3 | G | 0.08 | 0.02 | 0.012 |
| Q461.e2 | A | 0.076 | 0.009 | 0.034 |
| P0402_c2_11 | G | 0.073 | 0.003 | 0.01 |

TABLE 14-continued

| | | IC$_{50}$ | | |
|---|---|---|---|---|
| Virus ID | Clade* | NIH45-46 | NIH45-46$^{G54W}$ | 45-46m2 |
| 6244_13_B5_4576 | B (T/F) | 0.07 | 0.005 | 0.03 |
| CNE19 | BC | 0.07 | 0.002 | 0.022 |
| BJOX028000.10.3 | CRF01_AE (T/F) | 0.07 | 0.001 | 0.001 |
| X1632_S2_B10 | G | 0.07 | Not Tested | 0.001 |
| BJOX015000.11.5 | CRF01_AE (T/F) | 0.06 | 0.048 | 0.039 |
| SC422661.8 | B | 0.06 | 0.02 | 0.024 |
| 62357_14_D3_4589 | B (T/F) | 0.06 | 0.02 | 0.015 |
| WITO4160.33 | B | 0.06 | 0.01 | 0.015 |
| Ce2060_G9 | C (T/F) | 0.058 | 0.005 | 0.014 |
| Ce0682_E4 | C (T/F) | 0.054 | 0.01 | 0.007 |
| 231965.c01 | D | 0.051 | 0.001 | 0.001 |
| 263-8 | CRF02_AG | 0.05 | 0.001 | 0.018 |
| Q259.d2.17 | A | 0.043 | 0.001 | 0.001 |
| Ce1086_B2 | C (T/F) | 0.04 | 0.019 | 0.004 |
| TRJO4551.58 | B | 0.04 | 0.01 | 0.004 |
| 249M B10 | C (T/F) | 0.04 | 0.001 | 0.001 |
| 6811.v7.c18 | CD | 0.035 | 0.001 | 0.026 |
| R2184.c04 | CRF01_AE | 0.034 | 0.005 | 0.008 |
| 6480.v4.c25 | CD | 0.032 | 0.004 | 0.016 |
| X1254_c3 | G | 0.032 | 0.002 | 0.006 |
| Q842.d12 | A | 0.031 | 0.005 | 0.001 |
| CNE52 | BC | 0.03 | 0.01 | 0.004 |
| A07412M1.vrc12 | D | 0.03 | 0.001 | 0.001 |
| 3365.v2.c2 | A | 0.029 | 0.01 | 0.014 |
| C3347.c11 | CRF01_AEB | 0.029 | 0.001 | 0.007 |
| 1006_11_C3_1601 | B (T/F) | 0.027 | 0.001 | 0.009 |
| 3415.v1.c1 | A | 0.022 | 0.001 | 0.013 |
| X1193_c1 | G | 0.021 | 0.001 | 0.008 |
| 6952.v1.c20 | CD | 0.02 | 0.001 | 0.007 |
| Du156.12 | C | 0.02 | 0.001 | 0.003 |
| HIV-16055-2.3 | C | 0.02 | 0.001 | 0.002 |
| 191084 B7-19 | A (T/F) | 0.02 | 0.001 | 0.001 |
| ZM249M.PL1 | C | 0.017 | 0.002 | 0.001 |
| RHPA4259.7 | B | 0.017 | 0.001 | 0.001 |
| REJO4541.67 | B | 0.014 | 0.002 | 0.001 |
| 0815.v3.c3 | ACD | 0.014 | 0.001 | 0.001 |
| HIV-0013095-2.11 | C | 0.01 | 0.005 | 0.002 |
| BF1266.431a | C (T/F) | 0.01 | 0.001 | 0.002 |
| 1012_11_TC21_3257 | B (T/F) | 0.01 | 0.001 | 0.001 |
| Q769.d22 | A | 0.009 | 0.001 | 0.003 |
| 3301.v1.c24 | AC | 0.009 | 0.001 | 0.001 |
| CNE53 | BC | 0.008 | 0.001 | 0.006 |
| 6041.v3.c23 | AC | 0.006 | 0.001 | 0.001 |
| WEAU_d15_410_787 | B (T/F) | 0.005 | 0.001 | 0.008 |
| HIV-001428-2.42 | C | 0.001 | 0.001 | 0.001 |
| 0260.v5.c36 | A | NT | 0.117 | 0.032 |
| CNE8 | CRF01_AE | NT | 0.055 | 0.038 |

Against the panel of viruses listed in Table 14, 45-46 m2 antibody was as potent as NIH45-46$^{G54W}$ (geometric mean IC$_{50}$ values of 0.028 μg/ml and 0.030 μg/ml for 45-46 m2 and NIH45-46$^{G54W}$, respectively), but exhibited increased breadth as shown graphically in FIG. 18, neutralizing up to 96% of strains. Specifically, as shown in FIG. 18, the 45-46 m2 antibody was tested along with NIH45-46 and NIH45-46$^{G54W}$ in neutralization assays against the CAVD strain panel and showed overall improvement across these strains compared to NIH45-46 and NIH45-46$^{G54W}$. The first 28 strains of Table 14 above were either poorly neutralized (IC$_{50}$≥1.0 μg/ml) by NIH45-46 or were NIH45-46-resistant (IC$_{50}$>50 μg/ml). However, the 45-46 m2 antibody showed improved neutralization and had a geometric mean IC$_{50}$ of 0.35 μg/ml compared with geometric means of 1.84 μg/ml for NIH45-46$^{G54W}$ and 14.51 μg/ml for NIH45-46. For Table 14, IC$_{50}$s greater than 50 μg/ml are shown as 50 μg/ml.

As shown in FIGS. 19 and 20A-20I, the neutralizing activity of NIH45-46$^{G54W}$ was compared to the neutralizing activity of 45-46 m2 using viruses from an "elite neutralizer," patient VC10042, who developed unusually broad and potent cross-neutralizing antibody responses, but whose circulating viruses evolved to escape their action. With few exceptions, the viral clones isolated from VC10042 were highly resistant to known bNAbs, especially CD4bs antibodies (Sather, D. N. et al. *J Virol* (2012), the entire contents of which are herein incorporated by reference.) Only 1 viral clone isolated from VC10042 was susceptible to VRC01, but the majority (8 of 12) were moderately susceptible to NIH45-46$^{G54W}$. By contrast, NIH45-46 m2 neutralized all (12 of 12) of the viral clones with up to 10-fold increased potency compared with NIH45-46$^{G54W}$ when evaluated against NIH45-46$^{G54W}$-sensitive clones as shown in the neutralization graph of FIGS. 19 and 20A-20I, and the IC$_{80}$ data in Table 15 below.

TABLE 15

| | | IC$_{80}$ | | |
|---|---|---|---|---|
| Virus ID | Virus ID | NIH45-46 | NIH45-46$^{G54W}$ | 45-46m2 |
| Ce1172_H1 | C (T/F) | >50 | >50 | >50 |
| 620345.c01 | CRF01_AE | >50 | >50 | >50 |
| X2088_c9 | G | >50 | >50 | >50 |
| T278-50 | CRF02_AG | >50 | >50 | >50 |
| 89-F1_2_25 | CD | >50 | >50 | >50 |
| 6540.v4.c1 | AC | >50 | >50 | >50 |
| 6545.v4.c1 | AC | >50 | >50 | >50 |
| Du422.1 | C | >50 | >50 | >50 |
| 3817.v2.c59 | CD | >50 | >50 | >50 |
| CAP210.2.00.E8 | C | >50 | >50 | 9.052 |
| 211-9 | CRF02_AG | >50 | >50 | 0.898 |
| CAP45.2.00.G3 | C | >50 | >50 | 0.089 |
| T250-4 | CRF02_AG | >50 | 44.94 | 38.902 |
| Du172.17 | C | >50 | 42.85 | 0.125 |
| 3016.v5.c45 | D | >50 | 15.37 | 0.037 |
| 246F C1G | C (T/F) | >50 | 2.446 | 0.14 |
| CNE20 | BC | >50 | 0.48 | 0.02 |
| BJOX028000.10.3 | CRF01_AE (T/F) | >50 | 0.002 | 0.006 |
| X1632_S2_B10 | G | >50 | Not Tested | 0.007 |
| CNE21 | BC | 38.07 | 0.16 | 0.047 |
| C2101.c01 | CRF01_AE | 31.37 | 0.17 | 0.169 |
| ZM247v1(Rev-) | C (T/F) | 24.5 | 2.6 | 0.034 |
| HIV-16845-2.22 | C | 22.61 | 2.1 | 1.44 |
| ZM233M.PB6 | C | 14.18 | 0.11 | 0.083 |
| C1080.c03 | CRF01_AE | 11.56 | 0.91 | 0.589 |
| BJOX025000.01.1 | CRF01_AE (T/F) | 10 | 0.135 | 0.211 |
| 231966.c02 | D | 9.64 | 0.11 | 0.076 |
| THRO4156.18 | B | 8.22 | 1.81 | 2.736 |
| TRO.11 | B | 7.49 | 0.13 | 0.079 |
| BJOX010000.06.2 | CRF01_AE (T/F) | 6.37 | 4.499 | 5.037 |
| 3103.v3.c10 | ACD | 6.15 | 0.56 | 0.594 |
| T251-18 | CRF02_AG | 3.68 | 0.92 | 1.426 |
| T255-34 | CRF02_AG | 3.442 | 0.099 | 0.105 |
| Ce1176_A3 | C (T/F) | 3.17 | 0.45 | 0.467 |
| ZM135M.PL10a | C | 2.79 | 0.16 | 0.163 |
| CNE58 | BC | 2.08 | 0.05 | 0.042 |
| AC10.0.29 | B | 1.93 | 0.63 | 0.554 |
| QH0692.42 | B | 1.71 | 1.12 | 0.622 |
| 6240_08_TA5_4622 | B (T/F) | 1.55 | 0.603 | 0.623 |
| 235-47 | CRF02_AG | 1.49 | 0.017 | 0.019 |
| T257-31 | CRF02_AG | 1.38 | 0.45 | 0.471 |
| R1166.c01 | CRF01_AE | 1.21 | 0.51 | 1.01 |
| BJOX009000.02.4 | CRF01_AE | 1.16 | 0.564 | 0.621 |
| CNE30 | BC | 1.067 | 0.196 | 0.239 |
| Ce0393_C3 | C (T/F) | 0.936 | 0.089 | 0.151 |
| C4118.c09 | CRF01_AE | 0.91 | 0.087 | 0.058 |
| X2131_C1_B5 | G | 0.88 | 0.24 | 0.145 |
| Ce704809221_1B3 | C (T/F) | 0.88 | 0.21 | 0.484 |
| CNE17 | BC | 0.734 | 0.127 | 0.254 |
| 9004SS_A3_4 | A (T/F) | 0.65 | 0.28 | 0.138 |
| 928-28 | CRF02_AG | 0.64 | 0.25 | 0.159 |
| 7030102001E5(Rev-) | C (T/F) | 0.63 | 0.228 | 0.229 |
| ZM53M.PB12 | C | 0.61 | 0.16 | 0.257 |
| MS208.A1 | A | 0.6 | 0.17 | 0.089 |
| ZM214M.PL15 | C | 0.59 | 0.15 | 0.258 |
| ZM197M.PB7 | C | 0.55 | 0.18 | 0.274 |
| 6535.3 | B | 0.54 | 0.13 | 0.059 |
| Ce703010054_2A2 | C (T/F) | 0.538 | 0.077 | 0.051 |
| Q23.17 | A | 0.5 | 0.03 | 0.05 |
| 191821_E6_1 | D (T/F) | 0.46 | 0.099 | 0.13 |
| 1056_10_TA11_1826 | B (T/F) | 0.447 | 0.16 | 0.289 |
| ZM109F.PB4 | C | 0.437 | 0.07 | 0.086 |
| 191955_A11 | A (T/F) | 0.43 | 0.076 | 0.046 |
| PVO.4 | B | 0.41 | 0.16 | 0.099 |
| CNE5 | CRF01_AE | 0.41 | 0.116 | 0.137 |
| 1054_07_TC4_1499 | B (T/F) | 0.404 | 0.165 | 0.515 |
| CAAN5342.A2 | B | 0.4 | 0.21 | 0.299 |
| BJOX015000.11.5 | CRF01_AE (T/F) | 0.38 | 0.239 | 0.308 |
| SC05_8C11_2344 | B (T/F) | 0.38 | 0.2 | 0.219 |
| 1394C9G1(Rev-) | C (T/F) | 0.38 | 0.024 | 0.055 |
| CNE19 | BC | 0.37 | 0.028 | 0.102 |
| Ce2010_F5 | C (T/F) | 0.357 | 0.187 | 0.133 |
| Q461.e2 | A | 0.291 | 0.091 | 0.134 |
| Ce2060_G9 | C (T/F) | 0.29 | 0.042 | 0.062 |
| Ce1086_B2 | C (T/F) | 0.28 | 0.091 | 0.042 |
| 6244_13_B5_4576 | B (T/F) | 0.26 | 0.095 | 0.109 |

TABLE 15-continued

| | | IC$_{80}$ | | |
|---|---|---|---|---|
| Virus ID | Virus ID | NIH45-46 | NIH45-46$^{G54W}$ | 45-46m2 |
| WITO4160.33 | B | 0.26 | 0.04 | 0.073 |
| P1981_C5_3 | G | 0.24 | 0.07 | 0.045 |
| P0402_c2_11 | G | 0.214 | 0.023 | 0.042 |
| 1006_11_C3_1601 | B (T/F) | 0.196 | 0.008 | 0.037 |
| 62357_14_D3_4589 | B (T/F) | 0.19 | 0.07 | 0.084 |
| 249M B10 | C (T/F) | 0.17 | 0.019 | 0.017 |
| Ce0682_E4 | C (T/F) | 0.155 | 0.039 | 0.031 |
| Q259.d2.17 | A | 0.154 | 0.014 | 0.011 |
| SC422661.8 | B | 0.13 | 0.07 | 0.09 |
| TRJO4551.58 | B | 0.13 | 0.05 | 0.02 |
| A07412M1.vrc12 | D | 0.13 | 0.042 | 0.064 |
| R2184.c04 | CRF01_AE | 0.127 | 0.036 | 0.039 |
| 231965.c01 | D | 0.126 | 0.035 | 0.035 |
| CNE52 | BC | 0.12 | 0.052 | 0.028 |
| 6811.v7.c18 | CD | 0.113 | 0.033 | 0.11 |
| 3365.v2.c2 | A | 0.11 | 0.056 | 0.049 |
| X1254_c3 | G | 0.107 | 0.018 | 0.03 |
| 263-8 | CRF02_AG | 0.1 | 0.025 | 0.067 |
| 6480.v4.c25 | CD | 0.1 | 0.021 | 0.058 |
| C3347.c11 | CRF01_AE | 0.094 | 0.028 | 0.034 |
| 3415.v1.c1 | A | 0.086 | 0.023 | 0.054 |
| Q842.d12 | A | 0.073 | 0.025 | 0.017 |
| 191084 B7-19 | A (T/F) | 0.07 | 0.026 | 0.016 |
| 6952.v1.c20 | CD | 0.07 | 0.01 | 0.042 |
| X1193_c1 | G | 0.064 | 0.009 | 0.054 |
| HIV-16055-2.3 | C | 0.06 | 0.024 | 0.017 |
| Du156.12 | C | 0.054 | 0.005 | 0.024 |
| ZM249M.PL1 | C | 0.053 | 0.007 | 0.017 |
| 0815.v3.c3 | ACD | 0.052 | 0.003 | 0.004 |
| RHPA4259.7 | B | 0.047 | 0.007 | 0.007 |
| 1012_11_TC21_3257 | B (T/F) | 0.04 | 0.003 | 0.008 |
| 6041.v3.c23 | AC | 0.04 | 0.001 | 0.003 |
| CNE53 | BC | 0.039 | 0.005 | 0.039 |
| REJO4541.67 | B | 0.035 | 0.013 | 0.01 |
| Q769.d22 | A | 0.033 | 0.009 | 0.017 |
| 3301.v1.c24 | AC | 0.033 | 0.004 | 0.006 |
| HIV-0013095-2.11 | C | 0.03 | 0.027 | 0.017 |
| BF1266.431a | C (T/F) | 0.03 | 0.001 | 0.013 |
| WEAU_d15_410_787 | B (T/F) | 0.015 | 0.003 | 0.027 |
| HIV-001428-2.42 | C | 0.01 | 0.001 | 0.002 |
| 0260.v5.c36 | A | Not Tested | 0.399 | 0.084 |
| CNE8 | CRF01_AE | Not Tested | 0.24 | 0.156 |

Example 10

Vector Construction, Protein Expression and Protein Purification

Modifications of NIH45-46 heavy and light chain genes were made using QuikChange Lightning (from Agilent Technologies) and verified by DNA sequencing (from Eton Bioscience). Antibodies were expressed as IgGs using described protocols (Diskin et al., 2010 *Nat. Struct. Mol. Biol.*, 17:608-613, the entire contents of which are incorporated herein by reference), Briefly, secreted IgGs from polyethyleneimine (25 kD, linear; from Polysciences)—mediated, transiently-transfected HEK293-6E cells were captured on a protein A affinity column (from GE Healthcare) and eluted in 100 mM citrate pH 3.0, 150 mM sodium chloride. Antibodies subsequently used in neutralization assays were dialyzed into 10 mM citrate pH 3.0, 150 mM sodium chloride and adjusted to a concentration of 1 mg/ml, Fab fragments for crystallization and binding assays were obtained by digesting IgGs in 20 mM Tris pH 8.0, 150 mM sodium chloride (TBS) with a 1:100 ratio of papain (from Sigma) activated in 50 mM phosphate 7.0, 2 mM ethylenediaminetetraacetic acid, 10 mM cysteine at 37° C. until completion of the cleavage (20 min-60 min). The digested IgGs were then analyzed by SDS-PAGE. The Fc fragment of the IgG was removed by protein A chromatography and Fabs were further purified using Superdex 200 (from GE Healthcare) 10/300 Size Exclusion Chromatography (SEC).

The Glade A/E 93TH057-derived gp120 core (a gp120 construct lacking the V1/V2 and V3 loops) was expressed in insect cells and purified as described in Diskin et al, 2011. Supernatants from baculovirus-infected insect cells were collected, buffer exchanged into TBS and passed through a Ni$^{2+}$-NTA affinity column (from GE Healthcare). gp120 was eluted from the column using TBS plus 250 mM imidazole and purified using Superdex 200 16/60 SEC (from GE Healthcare) in TBS supplemented with 0.02% (w/v) sodium azide.

Example 11

Neutralization Assays

A pseudovirus neutralization assay was used to assess the neutralization potencies of the various antibodies against multiple HIV strains, as described in Montefiori, D.C. *Current protocols in Immunology*, edited by John E. Coligan Chapter 12, Unit 12 11 (2005), the entire contents of which are herein incorporated by reference. In all cases, neutralization was monitored by the reduction of a Tat-induced reporter gene (luciferase) in the presence of a three- or five-fold antibody dilution series (each concentration run in duplicate or triplicate) after a single round of pseudovirus infection in a TZM-bl cell line as described in Montefiori, previously incorporated by reference herein. Antibodies were incubated with 250 viral infectious units at 37° C. for one hour prior to incubation with the reporter cells (10,000 per well) for 48 hours. Luciferase levels were measured from a cell lysate using BrightGlo™ (from Promega) and a Victor3™ luminometer (from PerkinElmer). Data were fit by Prism (from GraphPad) using nonlinear regression to find the concentration at which 50% inhibition occurred (i.e., $IC_{50}$ value).

Example 12

Neutralization Assay of 3BNC50$_{T34X}$ Mutants

The Phe-43 equivalent position in 3BNC50 is threonine at position 54. This threonine was substituted with one of the 19 amino acids listed in Tables 16 and/or 17, and assayed in a neutralization assays against the viral strains including SC422661.8, TRO.11, CAP45.2.00G3, CAP210.2.00E8, Du172.17, and AC10.0.29.

$IC_{50}$ results averaged across the strains are shown below in Table 16. The substitutions shown in Table 16 show an average improvement over all the tested strains. Specifically, even though certain substitutions may show higher $IC_{50}$ values than the wild type for specific strains, the substitutions reported in Table 16 have $IC_{50}$ values averaged over all strains that are lower than the wild type. Table 17 shows the individual $IC_{50}$ values of the listed substitutions for the specific strains.

TABLE 16

| 3BNC60 T54 HCSubstitution | $IC_{50}$ |
|---|---|
| T54G | 0.03 |
| T54H | 0.04 |
| T54A | 0.14 |
| T54Q | 0.14 |
| T54R | 0.17 |
| T54Y | 0.20 |
| T54N | 0.22 |
| T54W | 0.25 |
| T54F | 0.25 |
| WT(T54) | 0.30 |

TABLE 17

$IC_{50}$ data for the indicated 3BNC60 mutants in 6 viral strains.

| 3BNC60 | SC422661.8 | TRO.11 | CAP45.2.00.G3 | CAP210.2.00.E8 | Du172.17 | AC10.0.29 |
|---|---|---|---|---|---|---|
| WT | 0.042 | 0.018 | 43.176 | 10.6 | 1.400 | >50 |
| T54A | 0.027 | 0.003 | >50 | 0.1 | >50 | 2.6 |
| T54E | 0.075 | 0.004 | >50 | >50 | >50 | 2.92 |
| T54G | 0.010 | 0.00030 | >50 | 11.9 | 0.02 | 0.623 |
| T54R | 0.014 | 0.006 | >50 | 5.0 | 2.15 | >50 |
| T54D | 0.556 | 0.036 | >50 | >50 | >50 | >50 |
| T54N | 0.025 | 0.008 | 16.7 | 16.3 | 0.662 | >50 |
| T54Q | 0.038 | 0.006 | 6.66 | 7.4 | 0.243 | 9.04 |
| T54H | 0.003 | 0.011 | 6.64 | 1.6 | 0.055 | >50 |
| T54K | 0.024 | 0.029 | >50 | >50 | >50 | >50 |
| T54S | 0.036 | 0.020 | 41.7 | 14.7 | 0.92 | >50 |
| T54I | 0.054 | 0.027 | >50 | >50 | 21.8 | >50 |
| T54V | 0.039 | 0.024 | >50 | 42.8 | 7.36 | >50 |
| T54L | 0.034 | 0.019 | >50 | 30.7 | 3.59 | >50 |
| T54M | 0.032 | 0.019 | >50 | 25.0 | 1.43 | >50 |
| T54P | 0.143 | 0.048 | >50 | >50 | >50 | >50 |
| T54W | 0.031 | 0.021 | ND | 2.6 | 2.2 | ND |
| T54Y | 0.020 | 0.012 | ND | 2.9 | 2.2 | ND |
| T54F | 0.025 | 0.023 | ND | 3.4 | 2.2 | ND |

As disclosed throughout, a PVL antibody such as NIH45-46, substituted at the Phe43$_{CD4}$-equivalent residue (position 54) with a heavy chain substitution selected from a hydrophobic amino acid, glycine, histidine, arginine, glutamine, asparagine, lysine, glutamic acid, and aspartic acid, has increased potency and breadth in HIV strains. Furthermore, including a second, light chain substitution of serine at position 28 of the light chain with tyrosine yields an even greater increase in potency and breadth in HIV strains.

While the present invention has been illustrated and described with reference to certain exemplary embodiments, those of ordinary skill in the art will understand that various modifications and changes may be made to the described embodiments without departing from the spirit and scope of the present invention, as defined in the following claims.

SEQUENCE LISTING SEQ ID NOS; 1-46

| Antibody Name | Light Chain SEQ ID NO: | | Heavy Chain SEQ ID NO: |
|---|---|---|---|
| VRC01 | 1 | | 2 |
| | EIVILTQSPGTLSLSPGETAIISCRTSQYGSLAWYQQRPGQAPRLVI YSGSTRAAGIP | | QVQLVQSG-- GQMKKPGESMRISCRASG--- |

| | | |
|---|---|---|
| Antibody Name | Light Chain SEQ ID NO: | Heavy Chain SEQ ID NO: |
| | DRFSGSRWGPDYNLTISNLESGDFGVYYCQQYEFFGQGTKVQTQVDIKR | YEFI------DCTLNWIRLAPGKRPEWMG |
| VRC02 | 3<br>EIVLTQSPGTLSLSPGETAIISCRTSQYGSLAWYQQRPGQAPRLVIYSGSTRAAGIPDRFSGSRWGPDYNLTIRNLESGDFGLYYCQQYEFFGQGTKVQVDIKR | 4<br>QVQLVQSGGQMKKPGESMRISCQASGYFFIDCTLNWVRLAPGRRPEWMGWLKPRGGAVNYARPLQGRYTMTRDVYSDTAFLELRSLTADDTAVYYCTRGKNCDYNWDFEHWGRGTPVTVSS |
| NIH-45-46 | 5<br>EIVLTQSPATLSLSPGETAIISCRTSQSGSLAWYQQRPGQAPRLVIYSGSTRAAGIPDRFSGSRWGADYNLSISNLESGDFGVYYCQQYEFFGQGTKVQVDIKRTVA | 6<br>QVRLSQSG--GQMKKPGESMRLSCRASG---YEFL------NCPINWIRLAPGRRPEWMGWLKPRGGAVNY-ARKFQGRVTMTRDVY----SDTAFLELRSLTSDDTAVYFCTRGKYCTARDYYNWDFEHWGRGAPVTVSS |
| 3BNC60 | 7<br>DIQMTQSPSSLSARVGDTVTITCQANGYLNWYQQRRGKAPKLLIYDGSKLERGVPARFSGRRWGQEYNLTINNLQPEDVATYFCQVYEFIVPGTRLDLKRTVA | 8<br>QVHLSQSG--AAVTKPGASVRVSCEASG---YKIS------DHFIHWWRQAPGQGLQWVGWINPKTGQPNN-PRQFQGRVSLTRQASWDFDTYSFYMDLKAVRSDDTAIYFCARQRSDFWDFDVWGSGTQVTVSS |
| 3BNC117 | 9<br>DIQMTQSPSSLSASVGDTVTITCQANGYLNWYQQRRGKAPKLLIYDGSKLERGVPSRFSGRRWGQEYNLTINNLQPEDIATYFCQVYEFVVPGTRLDLKRTVA | 10<br>QVQLLQSG---AAVTKPGASVRVSCEASG---YNIR------DYFIHWWRQAPGQGLQWVGWINPKTGQPNN-PRQFQGRVSLTRHASWDFDTFSFYMDLKALRSDDTAVYFCARQRSDYWDFDVWGSGTQVTVSS |
| 3BNC62 | 11<br>DIQMTQSPSSLSARVGDTVTITCQANGYLNWYQQRRGKAPKLLIYDGSKLETGVPSRFTGRRW-GQEYNLTINNLQPEDIATYFCQVYEFIVPGTR--LDLKRTVA | 12<br>QVRLLQSG--AAVTKPGASVRVSCEASG---YEIR------DYFIHWWRQAPGQGLQWVGWINPKTGQPNN-PRQFQGRVSLTRQASWDFDSYSFYMDLKALRSDDTGVYFCARQRSDYWDFDVWGSGTQVTVSS |
| 3BNC95 | 13<br>DIQMTQSPSSLSASVGDTVTITCQANGYLNWYQQRRGKAPKLLIYDGSKLERGVPSRFSGRRW-GQEYNLTINNLQPEDIATYFCQVYEFIVPGTRLDLKRTVA | 14<br>QVQLLQSG--AAVTKPGASVRVSCEASG---YNIR------DYFIHWWRQAPGQGLQWVGWINPKTGQPNN-PRLFQGRVSLTRHASWDFDTFSFYMDLKAVRSDDTAVYFCARQRSDYWDFDVWGSGTQVTVSS |

-continued

SEQUENCE LISTING SEQ ID NOS: 1-46

| Antibody Name | Light Chain SEQ ID NO: | Heavy Chain SEQ ID NO: |
|---|---|---|
| 3BNC176 | 15<br>DIQMTQSPSSSLSASVGDTVTITCQANGYLNWYQQRRGKAPKLLI<br>YDGSKLERGVP<br>SRFSGRRW-GQEYNLTINNLQAEDIATYFCQVYEFAVPGTR--<br>LDLKRTVA | 16<br>QVQLLQSG--<br>AAVTKPGASVAAVTKPGASVRVSCEASG---<br>YNIR------<br>DYFIHWWRQAPGQGLQWV<br>G<br>WINPKTGQPNN-<br>PRQFQGRVSLTRHASWDFD<br>TFSFYMDLKGLRSDDTAIY<br>FCARQRS<br>DYWDFDVWGSGTQVTVSS |
| 12A12 | 17<br>DIQMTQSPSSLSASVGDRVTITCQAGQGIG-<br>SSLQWYQQKPGKAPKLLVHGASNLHRGVP<br>SRFSGSGF-HTTFSLTISGLQRDDFATYFCAVLEFFGPGTK--<br>VEIKRTVA | 18<br>SQHLVQSG--<br>TQVKKPGASVRISCQASG---<br>YSFT------<br>DYVLHWRQAPGQGLEW<br>MG<br>WIKPVYGARNY-<br>ARRFQGRINFDRDIY----<br>REAIAFMDLSGLRSDDTALY<br>FCARDGSG<br>DDTSWHLDPWGQGTLVIVS<br>A |
| VRC-PG04 | 19<br>EIVLTQSPGTLSLSPGETASLSCTAASYGH---<br>MTWYQKKPGQPPKLLIFATSKRASGIP<br>DRFSGSQF-GKQYTLTITRMEPEDFARYYCQQLEFFGQGTR--<br>LEIRR | 20<br>QVQLVQSG--<br>SGVKKPGASVRVSCWTSE---<br>DIFER------<br>TELIHWRQAPGQGLEWIG<br>WVKTVTGAVNFGSPDFRQ<br>RVSLTRDRD----<br>LFTAHMDIRGLTQGDTATY<br>FCARQKF<br>YTGGQGWYFDLWGRGTLI<br>VVSS |
| VRC-CH30 | 21<br>DIQMTQSPSSLSASLGDRVTITCQASRGIG-<br>KDLNWYQQKPGKAPKLLVSDASILEGGVP<br>SRFSGSGF-HQNFSLTISSLQPEDVATYFCQQYETFGQGTK--VDIK | 22<br>QVQLVQSG--<br>AAVRKPGASVTVSCKFAED<br>DDYSPHWVNPAPEHYIHFL<br>RQAPGQQLEWLA<br>WMNPTNGAVNY-<br>AWQLHGRLTATRDGS----<br>MTTAFLEVRSLRSDDTAVY<br>YCARAQKRG<br>RSEWAYAHWGQGTPVLVS<br>S |
| VRC-CH31 | 23<br>DIQMTQSPSSLSASLGDRVTITCQASRGIG-<br>KDLNWYQQKAGKAPKLLVSDASTLEGGVP<br>SRFSGSGF-HQNFSLTISSLQAEDVATYFCQQYETFGQGTK--VDIK | 24<br>QVQLVQSG--<br>AAVRKPGASVTVSCKFAED<br>DDYSPYWVNPAPEHFIHFL<br>RQAPGQQLEWLA<br>WMNPTNGAVNY-<br>AWYLNGRVTATRDRS----<br>MTTAFLEVKSLRSDDTAVY<br>YCARAQKRG<br>RSEWAYAHWGQGTPVVVS<br>S |
| VRC-CH32 | 25<br>DIQMTQSPSSLSASLGDRVTITRTCQASRGIGKDLNWYQQKPGRAPK<br>LLVSDASILEGGVP<br>TRFSGSGF-HQNFSLTISSLQAEDVATYFCQQYETFGQGTKVDIK | 26<br>QVQLVQSG--<br>AAVRKPGASVTVSCKFAED<br>DDFSPHWVNPAPEHYIHFL<br>RQAPGQQLEWLA<br>WMKPTNGAVNY-<br>AWQLQGRVTVTRDRS----<br>QTTAFLEVKNLRSDDTAVY<br>YCARAQKRG<br>RSEWAYAHWGQGTPVVIS<br>A |

SEQUENCE LISTING SEQ ID NOS: 1-46

| Antibody Name | Light Chain SEQ ID NO: | Heavy Chain SEQ ID NO: |
| --- | --- | --- |
| VRC-CH33 | 27<br>DIQMTQSPSSLSASLGDRVTITCQASRGIG-KDLNWYQQKRGRAPRLLVSDASVLEGGVPSRFSGSGF-HQNFSLTISTLQPEDVATYFCQQYETFGQGTK--VDIK | 28<br>QVQLVQSG--AAVRKPGASISVSCKFADADDYSPHWMNPAPEHYIHFLRQAPGQQLEWLAWMNPTNGAVNY-AWYLNGRVTATRDRS----MTTAFLEVRSLRSDDTAVYYCARAQKRARSEWAYAHWGQGTPVVVSS |
| VRC-CH34 | 29<br>DIQMTQSPSSLSASLGDRVTITCQASRGIG-KDLNWYQQKAGKAPKLLVSDASILEGGVPSRFSGSGF-HQNFSLTISSLQPEDVATYFCQQYETFGQGTK--VDIK | 30<br>QVQLVQSG--AAVRKPGASVTVSCKFAEDDDWSPHWVNPAPEHYIHFLRQAPGQQLEWLAWMNPTNGAVNY-AWQLNGRLIATRDTS----MTTAFLEVKSLRSDDTAVYYCARAQKRGRSEWAYAHWGQGTPVVVSS |
| VRC03<br>for HC,<br>i = QDPD | 31<br>EIVLTQSPGILSLSPGETATLFCKASQGGNA--MTWYQKRRGQVPRLLIYDTSRRASGVPDRFVGSGS-GTDFFLTINKLDREDFAVYYCQQFEFFGLGSE--LEVHR | 32<br>QVQLVQSGAVIKTGPSSVKISCRASGYNFRDYSIHWVRLIPDKGFEWIGWIKPLWGAVSYARQLQGRVSMTRQLSQDPDDPDWGVAYMEFSGLTPADTAEYFCVRRGSCDYCGDFPWQYWGQGTVVVSS |
| 3BNC55 | 33<br>DIQMTQSPSSLSASVGDKVTITCQTSA----GYLNWYQQRRGRAPKLLMYDGSRLVTGVPSRFSGRRW-GTQYNLTIGSLQPEDIATYYCQVYEFFGPGTR--LDLKSTVA | 34<br>QVQLVQSG--TAVKRPGASVRVSCQASG---YTFT------DYFIYWRQAPGQGLEWLGWINPLTSQPSY-PSRFQGRLTLTRDTF----DEMLYMDLRGLRSDDTGIYFCARRHS-DYCDFDIWGSGTQIIVSS |
| 3BNC91 | 35<br>DIQMTQSPSSLSARVGDTVTITCQAN----GYLNWYQQRRGKAPIKLLIYDGSKLERGVPSRFSGRRW-GQEYNLTINNLQPEDIATYFCQVYEFAVPGTR--LDLKRTVA | 36<br>QVQLLQSG--AVVTKPGASVRVSCEASG---YKIR------DYFIHWRQAPGQGLQWVGWINPQTGQPNI-PRPFQGRVTLTRHASWDFDTFSFYMDLKALRSDDTAIYFCARRRSDYCDFDVWGSGTHVTVSS |

SEQUENCE LISTING SEQ ID NOS; 1-46

| Antibody Name | Light Chain SEQ ID NO: | Heavy Chain SEQ ID NO: |
| --- | --- | --- |
| 3BNC104 | 37<br>DIQMTQSPSSLSASIGDRVNITCQASRDTG-SALNWYQQKVGRPPRLLISAVSNLGAGVPSRFSGRRS-GTQSTLTINTLQPEDIATYFCQHYEFFGPGTK--VDIKRTVA | 38<br>EVQLVQSG--SDVRKPGATVTVSCKADEDEDDFTAY-----NYFMHWVRQAPGHGLEWIGWINPRTGQPNH-AKQFQGRVTLTRERS----TSTVFMKLTNLRLDDTAVYFCARPLRGG-DTWHYHSWGRGTSLTVSS |
| 3BNC89 | 39<br>DIQMTQSPSSLSASVGDKVTITCQTSA----GYLNWYQQRRGRAPKLLMYDGSRLVTGVPSRFSGRRW-GTQYNLTIGSLQPEDVATYYCQVYEFFGGTR--LDLKRTVA | 40<br>QVQLVQSG--TAVKRPGASVRVSCQASG---YTFI------DHFIYWWRQAPGQGLEWLGWINPLTSQPSY-PSRFQGRLTLTRDTF----DEMLYMDLRGLRSDDTGIYFCARRHSDYCDFDIWGSGTQIIVSS |
| 12A21 | 41<br>DIQMTQSPSSLSASVGDRYTINCQAGQGIGSSLNWYQKKPGRAPKLLVHGASNLQRGVPSRFSGSGFHTTFTLTISSLQPDDVATYFCAVFQWFGPGTKVDIKRTVAAPSVFIFPPSDEQLK | 42<br>SQHEVQSGTQVKKPGASVRVSCQASGYTFTNYILHWWRQAPGQGLEWMGLIKPVFGAVNYARQFQGRIQLTRDIYREIAFLDLSGLRSDDTAVYYCARDESGDDLKWHLHPWGQGTQVIVSPASTKG |
| VRC-PG04b | 43<br>EIVLTQSPGTLSLSPGETASLSCTAASYGHMTWYQKKPGQPPKLLIFATSKRASGIPDRFSGSQFGKQYTLTITRMEPEDFAGYYCQQVEFFGQGTRLEIR | 44<br>QVQLVQSGSGVKKPGASVRVSCWTSEDIFERTELIHWVRQAPGQGLEWIGWVKTVTGAVNFGSPNFRHRVSLTRDRDLFTAHMDIRGLTQGDTATYFCARQKFERGGQGWYFDLWGRGTLIVVSS |
| VRC03HC-VRC01LC | 1 | 32 |
| VRC01HC/VRC03LC | 31 | 2 |
| gVRC-H5(d74)/VRC-PG04LC | 19 | 45<br>QVQLVQSGGGVKKPGTSASFSCRTSDDIYDNEFFDSAFMHWVRLIPGQRPEWMGWMNPRSGAVNYARQLQPRVSMYRDRDLSTAYMEFKSLTSADTGTYFCARKKRGDGFNLYFDLWGRGSQVTVSSA |

| Antibody Name | Light Chain SEQ ID NO: | Heavy Chain SEQ ID NO: |
|---|---|---|
| gVR0H12(D74)/ VRC-PG04LC | 19 | 46<br>QVQLVQSGSAMKKP<br>GASVRVSCWTSEDIF<br>DTTELIHWVRQAPGQ<br>GLEWIGWVKAVSGA<br>VNYGSLDFRHRVSLT<br>RDRDLSTAHMDIRGL<br>TQDDTATYFCARQK<br>FARGDQGWFFDLWG<br>RGTLIVVSSA |

What is claimed is:

1. A human anti-CD4 binding site (anti-CD4bs) antibody having a heavy chain and a light chain, the heavy chain comprising a substitution at position 54 according to Kabat numbering, the substitution being selected from the group consisting of alanine, isoleucine, leucine, methionine, phenylalanine, tryptophan, tyrosine, valine, histidine, arginine, glutamine, asparagine, lysine, glutamic acid, and aspartic acid, the heavy chain comprising a sequence selected from the group consisting of SEQ ID NOs: 2, 4, 6, 8, 10, 12, 14, 16, 18, 20, 22, 24, 26, 28, 30, 32, 34, 36, 38, 40, 42, 44, 45, and 46; and the light chain comprising a sequence selected from the group consisting of SEQ ID NOs: 1, 3, 5, 7, 9, 11, 13, 15, 17, 19, 21, 23, 25, 27, 29, 31, 33, 35, 37, 39, 41, and 43.

2. The human anti-CD4bs antibody of claim 1, wherein the heavy chain substitution is tryptophan, tyrosine, phenylalanine, histidine, arginine, glutamine, or asparagine.

3. The human anti-CD4bs antibody of claim 1, wherein the human anti-CD4bs antibody is selected from the group consisting of VRC01, VRC02, NIH-45-46, 3BNC60, 3BNC117, 3BNC62, 3BNC95, 3BNC176, 12A21, VRC-PG04, VRC-CH30, VRC-CH31, VRC-CH32, VRC-CH33, VRC-CH34, VRC03 heavy chain with VRC01 light chain, gVRC-H5(d74) heavy chain with VRC-PG04 light chain, gVRC-H12(d74) heavy chain with VRC-PG04 light chain, VRC03, VRC01 heavy chain with VRC03 light chain, 3BNC55, 3BNC91, 3BNC104, 3BNC89, 12A21, and VRC-PG04b.

4. The human anti-CD4bs antibody of claim 3, wherein the heavy chain substitution is phenylalanine, tryptophan, tyrosine, histidine, arginine, glutamine or asparagine.

5. The human anti-CD4bs antibody of claim 1, wherein the human anti-CD4bs antibody is NIH45-46.

6. The human anti-CD4bs antibody of claim 5, wherein the heavy chain substitution is phenylalanine, tryptophan, tyrosine, histidine, arginine, glutamine or asparagine.

7. A pharmaceutical composition comprising the human anti-CD4bs antibody of claim 1 or a fragment thereof, and a pharmaceutically acceptable carrier.

8. The human anti-CD4bs antibody of claim 1, wherein the light chain comprises a substitution of tyrosine at position 28 according to Kabat numbering.

* * * * *

SEQUENCE LISTING

<160> NUMBER OF SEQ ID NOS: 46

<210> SEQ ID NO 1
<211> LENGTH: 104
<212> TYPE: PRT
<213> ORGANISM: Homo sapiens

<400> SEQUENCE: 1

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg
            100

<210> SEQ ID NO 2
<211> LENGTH: 49
<212> TYPE: PRT
<213> ORGANISM: Homo sapiens

<400> SEQUENCE: 2

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly

<210> SEQ ID NO 3
<211> LENGTH: 104
<212> TYPE: PRT
<213> ORGANISM: Homo sapiens

<400> SEQUENCE: 3

```
Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Arg Asn Leu Glu Ser Gly Asp
65                  70                  75                  80

Phe Gly Leu Tyr Tyr Cys Gln Gln Tyr Glu Phe Phe Gly Gln Gly Thr
                85                  90                  95

Lys Val Gln Val Asp Ile Lys Arg
            100
```

<210> SEQ ID NO 4
<211> LENGTH: 121
<212> TYPE: PRT
<213> ORGANISM: Homo sapiens

<400> SEQUENCE: 4

```
Gln Val Gln Leu Val Gln Ser Gly Gly Gln Met Lys Lys Pro Gly Glu
1               5                   10                  15

Ser Met Arg Ile Ser Cys Gln Ala Ser Gly Tyr Glu Phe Ile Asp Cys
            20                  25                  30

Thr Leu Asn Trp Val Arg Leu Ala Pro Gly Arg Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ala Asp Asp Thr Ala Val Tyr Tyr Cys
                85                  90                  95

Thr Arg Gly Lys Asn Cys Asp Tyr Asn Trp Asp Phe Glu His Trp Gly
            100                 105                 110

Arg Gly Thr Pro Val Thr Val Ser Ser
        115                 120
```

<210> SEQ ID NO 5
<211> LENGTH: 107
<212> TYPE: PRT
<213> ORGANISM: Homo sapiens

<400> SEQUENCE: 5

```
Glu Ile Val Leu Thr Gln Ser Pro Ala Thr Leu Ser Leu Ser Pro Gly
1               5                   10                  15

Glu Thr Ala Ile Ile Ser Cys Arg Thr Ser Gln Ser Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Ala Asp Tyr Asn Leu Ser Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95
```

```
Lys Val Gln Val Asp Ile Lys Arg Thr Val Ala
            100                 105

<210> SEQ ID NO 6
<211> LENGTH: 125
<212> TYPE: PRT
<213> ORGANISM: Homo sapiens

<400> SEQUENCE: 6

Gln Val Arg Leu Ser Gln Ser Gly Gly Gln Met Lys Lys Pro Gly Glu
1               5                   10                  15

Ser Met Arg Leu Ser Cys Arg Ala Ser Gly Tyr Glu Phe Leu Asn Cys
            20                  25                  30

Pro Ile Asn Trp Ile Arg Leu Ala Pro Gly Arg Arg Pro Glu Trp Met
        35                  40                  45

Gly Trp Leu Lys Pro Arg Gly Gly Ala Val Asn Tyr Ala Arg Lys Phe
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ser Asp Asp Thr Ala Val Tyr Phe Cys
                85                  90                  95

Thr Arg Gly Lys Tyr Cys Thr Ala Arg Asp Tyr Tyr Asn Trp Asp Phe
            100                 105                 110

Glu His Trp Gly Arg Gly Ala Pro Val Thr Val Ser Ser
        115                 120                 125

<210> SEQ ID NO 7
<211> LENGTH: 103
<212> TYPE: PRT
<213> ORGANISM: Homo sapiens

<400> SEQUENCE: 7

Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ala Arg Phe Ser Gly Arg Arg Trp Gly
    50                  55                  60

Gln Glu Tyr Asn Leu Thr Ile Asn Asn Leu Gln Pro Glu Asp Val Ala
65                  70                  75                  80

Thr Tyr Phe Cys Gln Val Tyr Glu Phe Ile Val Pro Gly Thr Arg Leu
                85                  90                  95

Asp Leu Lys Arg Thr Val Ala
            100

<210> SEQ ID NO 8
<211> LENGTH: 123
<212> TYPE: PRT
<213> ORGANISM: Homo sapiens

<400> SEQUENCE: 8

Gln Val His Leu Ser Gln Ser Gly Ala Ala Val Thr Lys Pro Gly Ala
1               5                   10                  15

Ser Val Arg Val Ser Cys Glu Ala Ser Gly Tyr Lys Ile Ser Asp His
            20                  25                  30

Phe Ile His Trp Trp Arg Gln Ala Pro Gly Gln Gly Leu Gln Trp Val
```

```
                35                  40                  45
Gly Trp Ile Asn Pro Lys Thr Gly Gln Pro Asn Asn Pro Arg Gln Phe
 50                  55                  60

Gln Gly Arg Val Ser Leu Thr Arg Gln Ala Ser Trp Asp Phe Asp Thr
 65                  70                  75                  80

Tyr Ser Phe Tyr Met Asp Leu Lys Ala Val Arg Ser Asp Asp Thr Ala
                 85                  90                  95

Ile Tyr Phe Cys Ala Arg Gln Arg Ser Asp Phe Trp Asp Phe Asp Val
                100                 105                 110

Trp Gly Ser Gly Thr Gln Val Thr Val Ser Ser
            115                 120

<210> SEQ ID NO 9
<211> LENGTH: 103
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
 1               5                  10                  15

Asp Thr Val Thr Ile Thr Cys Gln Ala Asn Gly Tyr Leu Asn Trp Tyr
                 20                  25                  30

Gln Gln Arg Arg Gly Lys Ala Pro Lys Leu Leu Ile Tyr Asp Gly Ser
             35                  40                  45

Lys Leu Glu Arg Gly Val Pro Ser Arg Phe Ser Gly Arg Arg Trp Gly
 50                  55                  60

Gln Glu Tyr Asn Leu Thr Ile Asn Asn Leu Gln Pro Glu Asp Ile Ala
 65                  70                  75                  80

Thr Tyr Phe Cys Gln Val Tyr Glu Phe Val Val Pro Gly Thr Arg Leu
                 85                  90                  95

Asp Leu Lys Arg Thr Val Ala
            100

<210> SEQ ID NO 10
<211> LENGTH: 123
<212> TYPE: PRT
<213> ORGANISM: Homo sapiens

<400> SEQUENCE: 10

Gln Val Gln Leu Leu Gln Ser Gly Ala Ala Val Thr Lys Pro Gly Ala
 1               5                  10                  15

Ser Val Arg Val Ser Cys Glu Ala Ser Gly Tyr Asn Ile Arg Asp Tyr
                 20                  25                  30

Phe Ile His Trp Trp Arg Gln Ala Pro Gly Gln Gly Leu Gln Trp Val
             35                  40                  45

Gly Trp Ile Asn Pro Lys Thr Gly Gln Pro Asn Asn Pro Arg Gln Phe
 50                  55                  60

Gln Gly Arg Val Ser Leu Thr Arg His Ala Ser Trp Asp Phe Asp Thr
 65                  70                  75                  80

Phe Ser Phe Tyr Met Asp Leu Lys Ala Leu Arg Ser Asp Asp Thr Ala
                 85                  90                  95

Val Tyr Phe Cys Ala Arg Gln Arg Ser Asp Tyr Trp Asp Phe Asp Val
                100                 105                 110

Trp Gly Ser Gly Thr Gln Val Thr Val Ser Ser
            115                 120
```

```
<210> SEQ ID NO 11
<211> LENGTH: 103
<212> TYPE: PRT
<213> ORGANISM: Homo sapiens

<400> SEQUENCE: 11

Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Thr Gly Val Pro Ser Arg Phe Thr Gly Arg Arg Trp Gly
50                  55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Ile Val Pro Gly Thr Arg Leu
                85                  90                  95

Asp Leu Lys Arg Thr Val Ala
            100

<210> SEQ ID NO 12
<211> LENGTH: 123
<212> TYPE: PRT
<213> ORGANISM: Homo sapiens

<400> SEQUENCE: 12

Gln Val Arg Leu Leu Gln Ser Gly Ala Ala Val Thr Lys Pro Gly Ala
1               5                   10                  15

Ser Val Arg Val Ser Cys Glu Ala Ser Gly Tyr Glu Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Gln Phe
50                  55                  60

Gln Gly Arg Val Ser Leu Thr Arg Gln Ala Ser Trp Asp Phe Asp Ser
65                  70                  75                  80

Tyr Ser Phe Tyr Met Asp Leu Lys Ala Leu Arg Ser Asp Asp Thr Gly
                85                  90                  95

Val Tyr Phe Cys Ala Arg Gln Arg Ser Asp Tyr Trp Asp Phe Asp Val
                100                 105                 110

Trp Gly Ser Gly Thr Gln Val Thr Val Ser Ser
            115                 120

<210> SEQ ID NO 13
<211> LENGTH: 103
<212> TYPE: PRT
<213> ORGANISM: Homo sapiens

<400> SEQUENCE: 13

Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ser Arg Phe Ser Gly Arg Arg Trp Gly
50                  55                  60
```

```
Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Ile Val Pro Gly Thr Arg Leu
                85                  90                  95

Asp Leu Lys Arg Thr Val Ala
            100

<210> SEQ ID NO 14
<211> LENGTH: 123
<212> TYPE: PRT
<213> ORGANISM: Homo sapiens

<400> SEQUENCE: 14

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Leu Phe
    50                  55                  60

Gln Gly Arg Val Ser Leu Thr Arg His Ala Ser Trp Asp Phe Asp Thr
65                  70                  75                  80

Phe Ser Phe Tyr Met Asp Leu Lys Ala Val Arg Ser Asp Asp Thr Ala
                85                  90                  95

Val Tyr Phe Cys Ala Arg Gln Arg Ser Asp Tyr Trp Asp Phe Asp Val
            100                 105                 110

Trp Gly Ser Gly Thr Gln Val Thr Val Ser Ser
        115                 120

<210> SEQ ID NO 15
<211> LENGTH: 103
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ser Arg Phe Ser Gly Arg Arg Trp Gly
    50                  55                  60

Gln Glu Tyr Asn Leu Thr Ile Asn Asn Leu Gln Ala Glu Asp Ile Ala
65                  70                  75                  80

Thr Tyr Phe Cys Gln Val Tyr Glu Phe Ala Val Pro Gly Thr Arg Leu
                85                  90                  95

Asp Leu Lys Arg Thr Val Ala
            100

<210> SEQ ID NO 16
<211> LENGTH: 123
<212> TYPE: PRT
<213> ORGANISM: Homo sapiens

<400> SEQUENCE: 16
```

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Gln Phe
    50                  55                  60

Gln Gly Arg Val Ser Leu Thr Arg His Ala Ser Trp Asp Phe Asp Thr
65                  70                  75                  80

Phe Ser Phe Tyr Met Asp Leu Lys Gly Leu Arg Ser Asp Asp Thr Ala
                85                  90                  95

Ile Tyr Phe Cys Ala Arg Gln Arg Ser Asp Tyr Trp Asp Phe Asp Val
            100                 105                 110

Trp Gly Ser Gly Thr Gln Val Thr Val Ser Ser
            115                 120

<210> SEQ ID NO 17
<211> LENGTH: 107
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Gln Ala Gly Gln Gly Ile Gly Ser Ser
            20                  25                  30

Leu Gln Trp Tyr Gln Gln Lys Pro Gly Lys Ala Pro Lys Leu Leu Val
        35                  40                  45

His Gly Ala Ser Asn Leu His Arg Gly Val Pro Ser Arg Phe Ser Gly
    50                  55                  60

Ser Gly Phe His Thr Thr Phe Ser Leu Thr Ile Ser Gly Leu Gln Arg
65                  70                  75                  80

Asp Asp Phe Ala Thr Tyr Phe Cys Ala Val Leu Glu Phe Phe Gly Pro
                85                  90                  95

Gly Thr Lys Val Glu Ile Lys Arg Thr Val Ala
            100                 105

<210> SEQ ID NO 18
<211> LENGTH: 122
<212> TYPE: PRT
<213> ORGANISM: Homo sapiens

<400> SEQUENCE: 18

Ser Gln His Leu Val Gln Ser Gly Thr Gln Val Lys Lys Pro Gly Ala
1               5                   10                  15

Ser Val Arg Ile Ser Cys Gln Ala Ser Gly Tyr Ser Phe Thr Asp Tyr
            20                  25                  30

Val Leu His Trp Trp Arg Gln Ala Pro Gly Gln Gly Leu Glu Trp Met
        35                  40                  45

Gly Trp Ile Lys Pro Val Tyr Gly Ala Arg Asn Tyr Ala Arg Arg Phe
    50                  55                  60

Gln Gly Arg Ile Asn Phe Asp Arg Asp Ile Tyr Arg Glu Ile Ala Phe
65                  70                  75                  80

Met Asp Leu Ser Gly Leu Arg Ser Asp Asp Thr Ala Leu Tyr Phe Cys
                85                  90                  95

Ala Arg Asp Gly Ser Gly Asp Thr Ser Trp His Leu Asp Pro Trp
            100                 105                 110

Gly Gln Gly Thr Leu Val Ile Val Ser Ala
        115                 120

<210> SEQ ID NO 19
<211> LENGTH: 102
<212> TYPE: PRT
<213> ORGANISM: Homo sapiens

<400> SEQUENCE: 19

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30

Trp Tyr Gln Lys Pro Gly Gln Pro Pro Lys Leu Leu Ile Phe Ala
        35                  40                  45

Thr Ser Lys Arg Ala Ser Gly Ile Pro Asp Arg Phe Ser Gly Ser Gln
50                  55                  60

Phe Gly Lys Gln Tyr Thr Leu Thr Ile Thr Arg Met Glu Pro Glu Asp
65                  70                  75                  80

Phe Ala Arg Tyr Tyr Cys Gln Gln Leu Glu Phe Phe Gly Gln Gly Thr
                85                  90                  95

Arg Leu Glu Ile Arg Arg
            100

<210> SEQ ID NO 20
<211> LENGTH: 125
<212> TYPE: PRT
<213> ORGANISM: Homo sapiens

<400> SEQUENCE: 20

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Pro
50                  55                  60

Asp Phe Arg Gln Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Tyr Thr Gly Gly Gln Gly Trp Tyr Phe
            100                 105                 110

Asp Leu Trp Gly Arg Gly Thr Leu Ile Val Val Ser Ser
        115                 120                 125

<210> SEQ ID NO 21
<211> LENGTH: 103
<212> TYPE: PRT
<213> ORGANISM: Homo sapiens

<400> SEQUENCE: 21

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp

```
                    20                  25                  30

Leu Asn Trp Tyr Gln Gln Lys Pro Gly Lys Ala Pro Lys Leu Leu Val
            35                  40                  45

Ser Asp Ala Ser Ile Leu Glu Gly Gly Val Pro Ser Arg Phe Ser Gly
        50                  55                  60

Ser Gly Phe His Gln Asn Phe Ser Leu Thr Ile Ser Ser Leu Gln Pro
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 22
<211> LENGTH: 131
<212> TYPE: PRT
<213> ORGANISM: Homo sapiens

<400> SEQUENCE: 22

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
            20                  25                  30

His Trp Val Asn Pro Ala Pro Glu His Tyr Ile His Phe Leu Arg Gln
            35                  40                  45

Ala Pro Gly Gln Gln Leu Glu Trp Leu Ala Trp Met Asn Pro Thr Asn
        50                  55                  60

Gly Ala Val Asn Tyr Ala Trp Gln Leu His Gly Arg Leu Thr Ala Thr
65                  70                  75                  80

Arg Asp Gly Ser Met Thr Thr Ala Phe Leu Glu Val Arg Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Leu
        115                 120                 125

Val Ser Ser
    130

<210> SEQ ID NO 23
<211> LENGTH: 103
<212> TYPE: PRT
<213> ORGANISM: Homo sapiens

<400> SEQUENCE: 23

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Ala Gly Lys Ala Pro Lys Leu Leu Val
            35                  40                  45

Ser Asp Ala Ser Thr Leu Glu Gly Gly Val Pro Ser Arg Phe Ser Gly
        50                  55                  60

Ser Gly Phe His Gln Asn Phe Ser Leu Thr Ile Ser Ser Leu Gln Ala
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
```

-continued

<210> SEQ ID NO 24
<211> LENGTH: 131
<212> TYPE: PRT
<213> ORGANISM: Homo sapiens

<400> SEQUENCE: 24

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
            20                  25                  30

Tyr Trp Val Asn Pro Ala Pro Glu His Phe Ile His Phe Leu Arg Gln
            35                  40                  45

Ala Pro Gly Gln Gln Leu Glu Trp Leu Ala Trp Met Asn Pro Thr Asn
        50                  55                  60

Gly Ala Val Asn Tyr Ala Trp Tyr Leu Asn Gly Arg Val Thr Ala Thr
65                  70                  75                  80

Arg Asp Arg Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Val Ser Ser
        130

<210> SEQ ID NO 25
<211> LENGTH: 103
<212> TYPE: PRT
<213> ORGANISM: Homo sapiens

<400> SEQUENCE: 25

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Pro Gly Arg Ala Pro Lys Leu Leu Val
            35                  40                  45

Ser Asp Ala Ser Ile Leu Glu Gly Gly Val Pro Thr Arg Phe Ser Gly
        50                  55                  60

Ser Gly Phe His Gln Asn Phe Ser Leu Thr Ile Ser Ser Leu Gln Ala
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 26
<211> LENGTH: 131
<212> TYPE: PRT
<213> ORGANISM: Homo sapiens

<400> SEQUENCE: 26

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Phe Ser Pro
            20                  25                  30

His Trp Val Asn Pro Ala Pro Glu His Tyr Ile His Phe Leu Arg Gln
        35                  40                  45

Ala Pro Gly Gln Gln Leu Glu Trp Leu Ala Trp Met Lys Pro Thr Asn
 50                  55                  60

Gly Ala Val Asn Tyr Ala Trp Gln Leu Gln Gly Arg Val Thr Val Thr
 65                  70                  75                  80

Arg Asp Arg Ser Gln Thr Thr Ala Phe Leu Glu Val Lys Asn Leu Arg
                 85                  90                  95

Ser Asp Asp Thr Ala Val Tyr Tyr Cys Ala Arg Ala Gln Lys Arg Gly
                100                 105                 110

Arg Ser Glu Trp Ala Tyr Ala His Trp Gly Gln Gly Thr Pro Val Val
            115                 120                 125

Ile Ser Ala
    130

<210> SEQ ID NO 27
<211> LENGTH: 103
<212> TYPE: PRT
<213> ORGANISM: Homo sapiens

<400> SEQUENCE: 27

Asp Ile Gln Met Thr Gln Ser Pro Ser Ser Leu Ser Ala Ser Leu Gly
 1               5                  10                  15

Asp Arg Val Thr Ile Thr Cys Gln Ala Ser Arg Gly Ile Gly Lys Asp
             20                  25                  30

Leu Asn Trp Tyr Gln Gln Lys Arg Gly Arg Ala Pro Arg Leu Leu Val
         35                  40                  45

Ser Asp Ala Ser Val Leu Glu Gly Gly Val Pro Ser Arg Phe Ser Gly
 50                  55                  60

Ser Gly Phe His Gln Asn Phe Ser Leu Thr Ile Ser Thr Leu Gln Pro
 65                  70                  75                  80

Glu Asp Val Ala Thr Tyr Phe Cys Gln Gln Tyr Glu Thr Phe Gly Gln
                 85                  90                  95

Gly Thr Lys Val Asp Ile Lys
            100

<210> SEQ ID NO 28
<211> LENGTH: 131
<212> TYPE: PRT
<213> ORGANISM: Homo sapiens

<400> SEQUENCE: 28

Gln Val Gln Leu Val Gln Ser Gly Ala Ala Val Arg Lys Pro Gly Ala
 1               5                  10                  15

Ser Ile Ser Val Ser Cys Lys Phe Ala Asp Ala Asp Asp Tyr Ser Pro
             20                  25                  30

His Trp Met Asn Pro Ala Pro Glu His Tyr Ile His Phe Leu Arg Gln
         35                  40                  45

Ala Pro Gly Gln Gln Leu Glu Trp Leu Ala Trp Met Asn Pro Thr Asn
 50                  55                  60

Gly Ala Val Asn Tyr Ala Trp Tyr Leu Asn Gly Arg Val Thr Ala Thr
 65                  70                  75                  80

Arg Asp Arg Ser Met Thr Thr Ala Phe Leu Glu Val Arg Ser Leu Arg
                 85                  90                  95

Ser Asp Asp Thr Ala Val Tyr Tyr Cys Ala Arg Ala Gln Lys Arg Ala
                100                 105                 110

Arg Ser Glu Trp Ala Tyr Ala His Trp Gly Gln Gly Thr Pro Val Val
            115                 120                 125

Val Ser Ser
    130

<210> SEQ ID NO 29
<211> LENGTH: 103
<212> TYPE: PRT
<213> ORGANISM: Homo sapiens

<400> SEQUENCE: 29

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Ala Gly Lys Ala Pro Lys Leu Leu Val
        35                  40                  45

Ser Asp Ala Ser Ile Leu Glu Gly Gly Val Pro Ser Arg Phe Ser Gly
    50                  55                  60

Ser Gly Phe His Gln Asn Phe Ser Leu Thr Ile Ser Ser Leu Gln Pro
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 30
<211> LENGTH: 131
<212> TYPE: PRT
<213> ORGANISM: Homo sapiens

<400> SEQUENCE: 30

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Asp Trp Ser Pro
            20                  25                  30

His Trp Val Asn Pro Ala Pro Glu His Tyr Ile His Phe Leu Arg Gln
        35                  40                  45

Ala Pro Gly Gln Gln Leu Glu Trp Leu Ala Trp Met Asn Pro Thr Asn
    50                  55                  60

Gly Ala Val Asn Tyr Ala Trp Gln Leu Asn Gly Arg Leu Thr Ala Thr
65                  70                  75                  80

Arg Asp Thr Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Val Ser Ser
    130

<210> SEQ ID NO 31
<211> LENGTH: 103
<212> TYPE: PRT
<213> ORGANISM: Homo sapiens

<400> SEQUENCE: 31

Glu Ile Val Leu Thr Gln Ser Pro Gly Ile Leu Ser Leu Ser Pro Gly
1               5                   10                  15

Glu Thr Ala Thr Leu Phe Cys Lys Ala Ser Gln Gly Gly Asn Ala Met
            20                  25                  30

Thr Trp Tyr Gln Lys Arg Arg Gly Gln Val Pro Arg Leu Leu Ile Tyr
        35                  40                  45

Asp Thr Ser Arg Arg Ala Ser Gly Val Pro Asp Arg Phe Val Gly Ser
    50                  55                  60

Gly Ser Gly Thr Asp Phe Phe Leu Thr Ile Asn Lys Leu Asp Arg Glu
65                  70                  75                  80

Asp Phe Ala Val Tyr Tyr Cys Gln Gln Phe Glu Phe Phe Gly Leu Gly
                85                  90                  95

Ser Glu Leu Glu Val His Arg
                100

<210> SEQ ID NO 32
<211> LENGTH: 130
<212> TYPE: PRT
<213> ORGANISM: Homo sapiens

<400> SEQUENCE: 32

Gln Val Gln Leu Val Gln Ser Gly Ala Val Ile Lys Thr Pro Gly Ser
1               5                   10                  15

Ser Val Lys Ile Ser Cys Arg Ala Ser Gly Tyr Asn Phe Arg Asp Tyr
            20                  25                  30

Ser Ile His Trp Val Arg Leu Ile Pro Asp Lys Gly Phe Glu Trp Ile
        35                  40                  45

Gly Trp Ile Lys Pro Leu Trp Gly Ala Val Ser Tyr Ala Arg Gln Leu
    50                  55                  60

Gln Gly Arg Val Ser Met Thr Arg Gln Leu Ser Gln Asp Pro Asp Asp
65                  70                  75                  80

Pro Asp Trp Gly Val Ala Tyr Met Glu Phe Ser Gly Leu Thr Pro Ala
                85                  90                  95

Asp Thr Ala Glu Tyr Phe Cys Val Arg Arg Gly Ser Cys Asp Tyr Cys
            100                 105                 110

Gly Asp Phe Pro Trp Gln Tyr Trp Gly Gln Gly Thr Val Val Val Val
        115                 120                 125

Ser Ser
    130

<210> SEQ ID NO 33
<211> LENGTH: 104
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Lys Val Thr Ile Thr Cys Gln Thr Ser Ala Gly Tyr Leu Asn Trp
            20                  25                  30

Tyr Gln Gln Arg Arg Gly Arg Ala Pro Lys Leu Leu Met Tyr Asp Gly
        35                  40                  45

Ser Arg Leu Val Thr Gly Val Pro Ser Arg Phe Ser Gly Arg Arg Trp
    50                  55                  60

Gly Thr Gln Tyr Asn Leu Thr Ile Gly Ser Leu Gln Pro Glu Asp Ile
65                  70                  75                  80

```
Ala Thr Tyr Tyr Cys Gln Val Tyr Glu Phe Phe Gly Pro Gly Thr Arg
                85                  90                  95

Leu Asp Leu Lys Ser Thr Val Ala
            100
```

<210> SEQ ID NO 34
<211> LENGTH: 119
<212> TYPE: PRT
<213> ORGANISM: Homo sapiens

<400> SEQUENCE: 34

```
Gln Val Gln Leu Val Gln Ser Gly Thr Ala Val Lys Arg Pro Gly Ala
1               5                   10                  15

Ser Val Arg Val Ser Cys Gln Ala Ser Gly Tyr Thr Phe Thr Asp Tyr
                20                  25                  30

Phe Ile Tyr Trp Trp Arg Gln Ala Pro Gly Gln Gly Leu Glu Trp Leu
            35                  40                  45

Gly Trp Ile Asn Pro Leu Thr Ser Gln Pro Ser Tyr Pro Ser Arg Phe
50                  55                  60

Gln Gly Arg Leu Thr Leu Thr Arg Asp Thr Phe Asp Glu Met Leu Tyr
65                  70                  75                  80

Met Asp Leu Arg Gly Leu Arg Ser Asp Thr Gly Ile Tyr Phe Cys
                85                  90                  95

Ala Arg Arg His Ser Asp Tyr Cys Asp Phe Asp Ile Trp Gly Ser Gly
            100                 105                 110

Thr Gln Ile Ile Val Ser Ser
        115
```

<210> SEQ ID NO 35
<211> LENGTH: 103
<212> TYPE: PRT
<213> ORGANISM: Homo sapiens

<400> SEQUENCE: 35

```
Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr
                20                  25                  30

Gln Gln Arg Arg Gly Lys Ala Pro Lys Leu Leu Ile Tyr Asp Gly Ser
            35                  40                  45

Lys Leu Glu Arg Gly Val Pro Ser Arg Phe Ser Gly Arg Arg Trp Gly
50                  55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Ala Val Pro Gly Thr Arg Leu
                85                  90                  95

Asp Leu Lys Arg Thr Val Ala
            100
```

<210> SEQ ID NO 36
<211> LENGTH: 123
<212> TYPE: PRT
<213> ORGANISM: Homo sapiens

<400> SEQUENCE: 36

```
Gln Val Gln Leu Leu Gln Ser Gly Ala Val Val Thr Lys Pro Gly Ala
1               5                   10                  15

Ser Val Arg Val Ser Cys Glu Ala Ser Gly Tyr Lys Ile Arg Asp Tyr
```

```
                        20                  25                  30
Phe Ile His Trp Trp Arg Gln Ala Pro Gly Gln Gly Leu Gln Trp Val
                35                  40                  45
Gly Trp Ile Asn Pro Gln Thr Gly Gln Pro Asn Ile Pro Arg Pro Phe
            50                  55                  60
Gln Gly Arg Val Thr Leu Thr Arg His Ala Ser Trp Asp Phe Asp Thr
65                  70                  75                  80
Phe Ser Phe Tyr Met Asp Leu Lys Ala Leu Arg Ser Asp Asp Thr Ala
                85                  90                  95
Ile Tyr Phe Cys Ala Arg Arg Ser Asp Tyr Cys Asp Phe Asp Val
            100                 105                 110
Trp Gly Ser Gly Thr His Val Thr Val Ser Ser
            115                 120

<210> SEQ ID NO 37
<211> LENGTH: 107
<212> TYPE: PRT
<213> ORGANISM: Homo sapiens

<400> SEQUENCE: 37

Asp Ile Gln Met Thr Gln Ser Pro Ser Ser Leu Ser Ala Ser Ile Gly
1               5                   10                  15
Asp Arg Val Asn Ile Thr Cys Gln Ala Ser Arg Asp Thr Gly Ser Ala
                20                  25                  30
Leu Asn Trp Tyr Gln Gln Lys Val Gly Arg Pro Pro Arg Leu Leu Ile
                35                  40                  45
Ser Ala Val Ser Asn Leu Gly Ala Gly Val Pro Ser Arg Phe Ser Gly
            50                  55                  60
Arg Arg Ser Gly Thr Gln Ser Thr Leu Thr Ile Asn Thr Leu Gln Pro
65                  70                  75                  80
Glu Asp Ile Ala Thr Tyr Phe Cys Gln His Tyr Glu Phe Phe Gly Pro
                85                  90                  95
Gly Thr Lys Val Asp Ile Lys Arg Thr Val Ala
            100                 105

<210> SEQ ID NO 38
<211> LENGTH: 125
<212> TYPE: PRT
<213> ORGANISM: Homo sapiens

<400> SEQUENCE: 38

Glu Val Gln Leu Val Gln Ser Gly Ser Asp Val Arg Lys Pro Gly Ala
1               5                   10                  15
Thr Val Thr Val Ser Cys Lys Ala Asp Glu Asp Glu Asp Phe Thr
                20                  25                  30
Ala Tyr Asn Tyr Phe Met His Trp Val Arg Gln Ala Pro Gly His Gly
                35                  40                  45
Leu Glu Trp Ile Gly Trp Ile Asn Pro Arg Thr Gly Gln Pro Asn His
            50                  55                  60
Ala Lys Gln Phe Gln Gly Arg Val Thr Leu Thr Arg Glu Arg Ser Thr
65                  70                  75                  80
Ser Thr Val Phe Met Lys Leu Thr Asn Leu Arg Leu Asp Asp Thr Ala
                85                  90                  95
Val Tyr Phe Cys Ala Arg Pro Leu Arg Gly Gly Asp Thr Trp His Tyr
            100                 105                 110
His Ser Trp Gly Arg Gly Thr Ser Leu Thr Val Ser Ser
```

```
<210> SEQ ID NO 39
<211> LENGTH: 104
<212> TYPE: PRT
<213> ORGANISM: Homo sapiens

<400> SEQUENCE: 39

Asp Ile Gln Met Thr Gln Ser Pro Ser Leu Ser Ala Ser Val Gly
1               5                   10                  15

Asp Lys Val Thr Ile Thr Cys Gln Thr Ser Ala Gly Tyr Leu Asn Trp
            20                  25                  30

Tyr Gln Gln Arg Arg Gly Arg Ala Pro Lys Leu Leu Met Tyr Asp Gly
            35                  40                  45

Ser Arg Leu Val Thr Gly Val Pro Ser Arg Phe Ser Gly Arg Arg Trp
50                  55                  60

Gly Thr Gln Tyr Asn Leu Thr Ile Gly Ser Leu Gln Pro Glu Asp Val
65                  70                  75                  80

Ala Thr Tyr Tyr Cys Gln Val Tyr Glu Phe Phe Gly Pro Gly Thr Arg
                85                  90                  95

Leu Asp Leu Lys Arg Thr Val Ala
            100

<210> SEQ ID NO 40
<211> LENGTH: 119
<212> TYPE: PRT
<213> ORGANISM: Homo sapiens

<400> SEQUENCE: 40

Gln Val Gln Leu Val Gln Ser Gly Thr Ala Val Lys Arg Pro Gly Ala
1               5                   10                  15

Ser Val Arg Val Ser Cys Gln Ala Ser Gly Tyr Thr Phe Ile Asp His
            20                  25                  30

Phe Ile Tyr Trp Trp Arg Gln Ala Pro Gly Gln Gly Leu Glu Trp Leu
            35                  40                  45

Gly Trp Ile Asn Pro Leu Thr Ser Gln Pro Ser Tyr Pro Ser Arg Phe
50                  55                  60

Gln Gly Arg Leu Thr Leu Thr Arg Asp Thr Phe Asp Glu Met Leu Tyr
65                  70                  75                  80

Met Asp Leu Arg Gly Leu Arg Ser Asp Thr Gly Ile Tyr Phe Cys
                85                  90                  95

Ala Arg Arg His Ser Asp Tyr Cys Asp Phe Asp Ile Trp Gly Ser Gly
            100                 105                 110

Thr Gln Ile Ile Val Ser Ser
        115

<210> SEQ ID NO 41
<211> LENGTH: 122
<212> TYPE: PRT
<213> ORGANISM: Homo sapiens

<400> SEQUENCE: 41

Asp Ile Gln Met Thr Gln Ser Pro Ser Ser Leu Ser Ala Ser Val Gly
1               5                   10                  15

Asp Arg Val Thr Ile Asn Cys Gln Ala Gly Gln Gly Ile Gly Ser Ser
            20                  25                  30

Leu Asn Trp Tyr Gln Lys Lys Pro Gly Arg Ala Pro Lys Leu Leu Val
            35                  40                  45
```

```
His Gly Ala Ser Asn Leu Gln Arg Gly Val Pro Ser Arg Phe Ser Gly
         50                  55                  60

Ser Gly Phe His Thr Thr Phe Thr Leu Thr Ile Ser Ser Leu Gln Pro
 65                  70                  75                  80

Asp Asp Val Ala Thr Tyr Phe Cys Ala Val Phe Gln Trp Phe Gly Pro
                 85                  90                  95

Gly Thr Lys Val Asp Ile Lys Arg Thr Val Ala Ala Pro Ser Val Phe
            100                 105                 110

Ile Phe Pro Pro Ser Asp Glu Gln Leu Lys
            115                 120
```

<210> SEQ ID NO 42
<211> LENGTH: 127
<212> TYPE: PRT
<213> ORGANISM: Homo sapiens

<400> SEQUENCE: 42

```
Ser Gln His Leu Val Gln Ser Gly Thr Gln Val Lys Lys Pro Gly Ala
 1               5                  10                  15

Ser Val Arg Val Ser Cys Gln Ala Ser Gly Tyr Thr Phe Thr Asn Tyr
                20                  25                  30

Ile Leu His Trp Trp Arg Gln Ala Pro Gly Gln Gly Leu Glu Trp Met
            35                  40                  45

Gly Leu Ile Lys Pro Val Phe Gly Ala Val Asn Tyr Ala Arg Gln Phe
         50                  55                  60

Gln Gly Arg Ile Gln Leu Thr Arg Asp Ile Tyr Arg Glu Ile Ala Phe
 65                  70                  75                  80

Leu Asp Leu Ser Gly Leu Arg Ser Asp Thr Ala Val Tyr Tyr Cys
                 85                  90                  95

Ala Arg Asp Glu Ser Gly Asp Asp Leu Lys Trp His Leu His Pro Trp
            100                 105                 110

Gly Gln Gly Thr Gln Val Ile Val Ser Pro Ala Ser Thr Lys Gly
            115                 120                 125
```

<210> SEQ ID NO 43
<211> LENGTH: 101
<212> TYPE: PRT
<213> ORGANISM: Homo sapiens

<400> SEQUENCE: 43

```
Glu Ile Val Leu Thr Gln Ser Pro Gly Thr Leu Ser Leu Ser Pro Gly
 1               5                  10                  15

Glu Thr Ala Ser Leu Ser Cys Thr Ala Ala Ser Tyr Gly His Met Thr
                20                  25                  30

Trp Tyr Gln Lys Lys Pro Gly Gln Pro Pro Lys Leu Leu Ile Phe Ala
            35                  40                  45

Thr Ser Lys Arg Ala Ser Gly Ile Pro Asp Arg Phe Ser Gly Ser Gln
         50                  55                  60

Phe Gly Lys Gln Tyr Thr Leu Thr Ile Thr Arg Met Glu Pro Glu Asp
 65                  70                  75                  80

Phe Ala Gly Tyr Tyr Cys Gln Gln Val Glu Phe Phe Gly Gln Gly Thr
                 85                  90                  95

Arg Leu Glu Ile Arg
            100
```

<210> SEQ ID NO 44

-continued

```
<211> LENGTH: 125
<212> TYPE: PRT
<213> ORGANISM: Homo sapiens

<400> SEQUENCE: 44

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Pro
50                  55                  60

Asn Phe Arg His Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Glu Arg Gly Gly Gln Gly Trp Tyr Phe
            100                 105                 110

Asp Leu Trp Gly Arg Gly Thr Leu Ile Val Val Ser Ser
        115                 120                 125

<210> SEQ ID NO 45
<211> LENGTH: 128
<212> TYPE: PRT
<213> ORGANISM: Homo sapiens

<400> SEQUENCE: 45

Gln Val Gln Leu Val Gln Ser Gly Gly Gly Val Lys Lys Pro Gly Thr
1               5                   10                  15

Ser Ala Ser Phe Ser Cys Arg Thr Ser Asp Asp Ile Tyr Asp Asn Glu
            20                  25                  30

Phe Phe Asp Ser Ala Phe Met His Trp Val Arg Leu Ile Pro Gly Gln
        35                  40                  45

Arg Pro Glu Trp Met Gly Trp Met Asn Pro Arg Ser Gly Ala Val Asn
50                  55                  60

Tyr Ala Arg Gln Leu Gln Pro Arg Val Ser Met Tyr Arg Asp Arg Asp
65                  70                  75                  80

Leu Ser Thr Ala Tyr Met Glu Phe Lys Ser Leu Thr Ser Ala Asp Thr
                85                  90                  95

Gly Thr Tyr Phe Cys Ala Arg Lys Lys Arg Gly Asp Gly Phe Asn Leu
            100                 105                 110

Tyr Phe Asp Leu Trp Gly Arg Gly Ser Gln Val Ile Val Ser Ser Ala
        115                 120                 125

<210> SEQ ID NO 46
<211> LENGTH: 126
<212> TYPE: PRT
<213> ORGANISM: Homo sapiens

<400> SEQUENCE: 46

Gln Val Gln Leu Val Gln Ser Gly Ser Ala Met Lys Lys Pro Gly Ala
1               5                   10                  15

Ser Val Arg Val Ser Cys Trp Thr Ser Glu Asp Ile Phe Asp Thr Thr
            20                  25                  30

Glu Leu Ile His Trp Val Arg Gln Ala Pro Gly Gln Gly Leu Glu Trp
        35                  40                  45
```

-continued

```
Ile Gly Trp Val Lys Ala Val Ser Gly Ala Val Asn Tyr Gly Ser Leu
    50                  55                  60

Asp Phe Arg His Arg Val Ser Leu Thr Arg Asp Arg Asp Leu Ser Thr
65                  70                  75                  80

Ala His Met Asp Ile Arg Gly Leu Thr Gln Asp Asp Thr Ala Thr Tyr
                85                  90                  95

Phe Cys Ala Arg Gln Lys Phe Ala Arg Gly Asp Gln Gly Trp Phe Phe
            100                 105                 110

Asp Leu Trp Gly Arg Gly Thr Leu Ile Val Val Ser Ser Ala
        115                 120                 125
```